United States Patent
Ko et al.

(10) Patent No.: US 9,574,240 B2
(45) Date of Patent: Feb. 21, 2017

(54) GENE AMPLIFICATION OF COACTIVATOR COAA AND USES THEREOF

(71) Applicant: Lan Ko, Augusta, GA (US)

(72) Inventors: Lan Ko, Augusta, GA (US); Yang Sui Brooks, Augusta, GA (US)

(73) Assignee: Lan Ko, Augusta, GA (US)

( * ) Notice: Subject to any disclaimer, the term of this patent is extended or adjusted under 35 U.S.C. 154(b) by 126 days.

(21) Appl. No.: 14/522,929

(22) Filed: Oct. 24, 2014

(65) Prior Publication Data

US 2015/0111209 A1  Apr. 23, 2015

Related U.S. Application Data

(63) Continuation of application No. 12/029,939, filed on Feb. 12, 2008, now abandoned.

(60) Provisional application No. 60/900,868, filed on Feb. 12, 2007.

(51) Int. Cl.
  *C12Q 1/68* (2006.01)
  *G01N 33/574* (2006.01)

(52) U.S. Cl.
  CPC ........ *C12Q 1/6886* (2013.01); *G01N 33/57484* (2013.01); *C12Q 2600/112* (2013.01); *C12Q 2600/118* (2013.01); *C12Q 2600/136* (2013.01); *C12Q 2600/156* (2013.01); *C12Q 2600/158* (2013.01); *G01N 2333/4706* (2013.01); *G01N 2800/52* (2013.01)

(58) Field of Classification Search
  USPC .................................. 435/6.1, 91.1, 325, 375
  See application file for complete search history.

(56) References Cited

U.S. PATENT DOCUMENTS

| | | |
|---|---|---|
| 5,124,246 A | 6/1992 | Urdea |
| 5,359,100 A | 10/1994 | Warner |
| 5,545,730 A | 8/1996 | Urdea |
| 5,571,670 A | 11/1996 | Urdea |
| 5,580,731 A | 12/1996 | Chang |
| 5,591,584 A | 1/1997 | Chang |
| 5,594,117 A | 1/1997 | Urdea |
| 5,594,118 A | 1/1997 | Urdea |
| 5,597,909 A | 1/1997 | Urdea |
| 5,624,802 A | 4/1997 | Urea |
| 5,635,352 A | 6/1997 | Urdea |
| 5,681,697 A | 10/1997 | Urdea |
| 5,681,702 A | 10/1997 | Collins |

(Continued)

OTHER PUBLICATIONS

Peterson et al. (Journal of American Chemical Society, 2002, vol. 124:14601-14607).

(Continued)

*Primary Examiner* — Terra C Gibbs

(57) ABSTRACT

It has been discovered that amplifications in the gene coactivator activator (CoAA) blocks stem cell differentiation and induces cancer stem cells. One embodiment provides compositions and methods for treating or alleviating one or more symptoms associated with cancer due to gene amplifications in CoAA. Another embodiment provides methods and compositions for detecting cancer due to gene amplifications in CoAA. Still another embodiment provides methods for identifying compounds, antibodies and nucleic acid molecules that are useful for treating cancer due to gene amplifications in CoAA. Preferably the disclosed compositions antagonize or interfere with the CoAA amplicons and the biological activity of CoAA and or splice variants thereof.

5 Claims, 14 Drawing Sheets

(56) References Cited

U.S. PATENT DOCUMENTS

| | | |
|---|---|---|
| 6,440,737 B1 | 8/2002 | Frier |
| 7,399,853 B2 | 7/2008 | Frier |

OTHER PUBLICATIONS

Zinszner, et al., "A novel effector domain from the RNA-binding protein TLS or EWS is required for oncogenic transformation by CHOP", Genes Dev., 8:2513 2526 (1994).

Zlokarnik, et al., "Quantitation of transcription and clonal selection of single living cells with beta lactamase as reporter", Science, 279:84-8 (1998).

Anderson, et al., "Directed proteomic analysis of the human nucleolus", Current Biology, 12:1M11 (2002).

Anzick, et al., "AIBI, a steroid receptor coactivator amplified in breast and ovarian cancer", Science, 277(5328):965-968 (1997).

Aranda and Pascual, "Nuclear hormone receptors and gene expression", Physiol. Rev., 81(3):1269 1304 (2001).

Auboeuf, et al., "CoAA, a nuclear receptor coactivator protein at the interface of transcriptiona coactivation and RNA splicing" Mol. Cell. Biol., 24:442-453 (2004).

Auboeuf, et al., "Coordinate regulation of transcription and splicing by steroid receptor coregulators", Science, 298(5592):416-419 (2002).

Bell and Van Zant, "Stem cells, aging, and cancer: inevitabilities and outcomes", Oncogene, 23(43):7290w7296 (2004).

Berns, et al., "Stem cells for lung cancer?", Cell, 121(6):81lw813 (2005).

Breit, "The SYT protein involved in the t(X;I8) synovial sarcoma translocation is a transcriptional activator localised in nuclear bodies", Hum. Mol. Genet., 6(9):1559-1564 (1997).

Butiel, et al., "Common fragile sites and cancer: targeted cloning by insertional mutagenesis", Ann. N }' Acad Sci., 1028:14w27 (2004).

Chen, et al., "Tra2betal regulates PI9 neuronal differentiation and the splicing of FGF-2R and GluRMB minigenes", Cell Bioi_ Int., 28(11):79lw799 (2004).

Chothia, et al., "Domain association in immunoglobulin molecules. The packing of variable domains.", J Mol. Bioi., 186;65lw63 (1985).

Conway-Campbell, et al., "The extracellular domain of the growth hormone receptor interacts with coactivator activator to promote cell proliferation", Mol. Endocrinol., 22(9):2190-202 (2008). Epub Jul. 11, 2008.

Coquelle, et al., "Expression of fragile sites triggers intrachromosomal mammalian gene amplification and sets boundaries to early amplicons", Cell, 89(2):215-225 (1997).

Coucouvanis and Martin, "BMP signaling plays a role in visceral endoderm differentiation and cavitation in the early mouse embryo", Development, 126(3):535-546 (1999).

David and Reisfeld, "Protein iodination with solid state lactoperoxidase", Biochemistry, 13(5):1014-21 (1974).

Ellington and Szostak, "In vitro selection of RNA molecules that bind specific ligands", Nature 346(6287):818 (1990).

Fox, et al., "Paraspeckles: a novel nuclear domain", Curr. Bioi., 12:13-25 (2002).

Gianakopoulos and Skerjanc, "Hedgehog signaling induces cardiomyogenesis in P19 cells", J. Biol. Chem., 280(22):21022-21028 (2005).

Greaves and Wiemels, "Origins of chromosome translocations in childhood leukaemia", Nat. Rev. Cancer, 3 (9):639-649 (2003).

Guan, et al., "Hybrid selection of transcribed sequences from microdissected DNA: isolation of genes within amplified region at 20q11-ql3.2 in breast cancer", Cancer Res., 56(15):3446-3450 (1996).

Hunter, et al., "Preparation of iodine-131 labelled human growth hormone of high specific activity", Nature, 194:495-6 (1962).

Iwasaki, et al., "Identification and characterization ofRRM-containing coactivator activator (CoAA) as TRBP-interacting protein, and its splice variant as a coactivator modulator (CoAM)", J. Biol. Chem., 276(36):33375-33383 (2001).

Jones-Villeneuve, et al., "Retinoic acid induces embryonal carcinoma cells to differentiate into neurons and glial cells", J. Cell Bioi., 94(2):253-262 (1982).

Kang, et al. "Dual roles for coactivator activator and its counterbalancing isoform coactivator modulator in human kidney cell tumongenesis", Cancer Res., 1;68(19):788796 (2008).

Ko and Chin, "Nuclear receptor coactivator thyroid hormone receptor-binding protein (TRBP) interacts with and stimulates its associated DNA dependent protein kinase", J. Bioi. Chern., 278:11471-11479 (2003).

Ko, et al., "Ser 884 adjacent to the LXXLL motif of coactivator TRBP defines selectivity for ERs and TRs", Mol. Endocrinol., 16:128 140 (2002).

Ko, et al., "Thyroid hormone receptor-binding protein, an LXXLL motif-containing protein, functions as a general coactivator", Proc. Natl. Acad. Sci. U.S.A., 97:6212-6217 (2000).

Koreth, et al., "Chromosomes, 11Q and cancer: a review", J. Pathol., 187(1):28-38 (1999).

Kornblihtt, "Promoter usage and alternative splicing", Curr. Opin. Cell Biol., 17:262-268 (2005).

Kuang, et al., "Deletion of the cancer-amplified coactivator AIB3 results in defective placentation and embryonic lethality", J. Biol. Chem., 277:45356-45360 (2002).

Lammie and Peters, "Chromosome 11q13 abnormalities in human cancer", Cancer Cells, 3(11):413-420 (1991).

Lockhart, et al., "Expression monitoring by hybridization to high-density oligonucleotide arrays", Nature Biotechnology, 14(13):1675-1680 (1996).

Lund, et al., "Human Fe gamma RI and Fe gamma Rli interact with distinct but overlapping sites on human IgG", J. Immun., 147(8): 2657 2662 (1991).

McKenna and O'Malley, "Combinatorial control of gene expression by nuclear receptors and coregulators", Cell, 108(4):465-474 (2002).

McKenna, et al., "Nuclear receptor coactivators: cellular and molecular biology", Endocr. Rev., 20:321.

Morgan, et al., "The N-terminal end of the CH2 domain of chimeric human IgG1 anti-ID.,A-DR is necessary for Clq, Fe gamma RI and Fe gamma RIII binding", Immunology, 86(2):319 324 (1995).

Novotny and Haber. "Structural invariants of antigen binding: comparison of immunoglobulin VLVH and VL-VL domain dirners", Proc. Nat/. Acad Sci. USA, 82(14): 4592 4596 (1985).

Nygren, et al., "Conjugation of horseradish peroxidase to Fab fragments with different hornobifunctional and heterobifunctional crosslinking reagents. A comparative study", J. Histochem. and Cytochem., 30(5):407 (1982).

Otto, et al., "Lung epithelial stern cells", J. Pathol., 197(4):527-535 (2002).

Pain, et al., "Preparation of protein A-peroxidase rnonoconjugate using a heterobifunctional reagent, and its use in enzyme irnrnunoassays", J. Immunol. Meth., 40(2):219 (1981).

Perani, et al., "The proto-oncoprotein SYT interacts with SYT interacting protein/co activator activator (SIP/CoAA), a human nuclear receptor co-activator with similarity to EWS and TLS/FUS family of proteins", J. Bioi. Chern., 280 (52):42863-76 (2005). Epub Oct. 14, 2005.

Russell, et al., "Alpha 6 beta 4 integrin regulates keratinocyte chemotaxis through differential GTPase activation and antagonism of alpha 3 beta 1 integrin", J. Cell Sci., ll6(Pt 17):3543-3556 (2003).

Schratt, et al., "SRF regulates Bcl-2 expression and promotes cell survival during murine embryonic development", Embo. J., 23(8):1834-1844 (2004).

Sui, et al., "Gene amplification and associated loss of5' regulatory sequences ofCoAA in human cancers", Oncogene, 26(6):822-835 (2007). Epub Jul. 31, 2006.

Torres Arzayus, et al., "High tumor incidence and activation of the PI3K/AKT pathway in transgenic mice define Affil as an oncogene", Cancer Cel/6(3):263-274 (2004).

Tuerk and Gold, "Systematic evolution of ligands by exponential enrichment: RNA ligands to bacteriophage T4 DNA polymerase", Science, 249(4968):505 10 (1990).

(56) References Cited

OTHER PUBLICATIONS

Vander Heyden and Defize, "Twenty one years of P19 cells: what an embryonal carcinoma cell line taught us about cardiomyocyte differentiation", Cardiovasc. Res, 58(2):292 302 (2003).

Yang, et al., "Switched alternative splicing of oncogene CoAA during embryonal carcinoma stem cell differentiation", Nucleic Acids Res? 35:19191932 (2007). Epub Mar. 1, 2007.

Yang, et al. "The diverse superfamily of lysine acetyltransferases and their roles in leukemia and other diseases", Nucleic Acids Res., 32(3):959-976 (2004).

Zainabadi, et al., "A 700-kb physical and transcription map of the cervical cancer tumor suppressor gene locus on chromosome 11q13", Genomics 85(6):704 714 (2005).

● CoAA
□ CoAM

US 9,574,240 B2

GENE AMPLIFICATION OF COACTIVATOR COAA AND USES THEREOF

CROSS REFERENCES TO RELATED APPLICATIONS

This application is a continuation of U.S. application Ser. No. 12/029,939 filed on Feb. 12, 2008, which claims priority to and benefit of U.S. Provisional Patent Application No. 60/900,868 filed on Feb. 12, 2007, and is incorporated herein by reference in its entirety.

FIELD OF THE INVENTION

Aspects of the invention are generally related to the field of molecular biology, gene diagnostics, and gene therapy.

BACKGROUND OF THE INVENTION

Cancer is an often fatal disease that affects a significant portion of the population. From 2000 to 2004 the National Cancer Institute estimated that the age-adjusted death rate due to cancer in the U.S. was 192.7 per 100,000 men and women per year. In January of 2003 approximately 10.5 million Americans had a history of cancer.

Cancer is a group of diseases characterized by uncontrolled growth and spread of abnormal cells. If the spread is not controlled, it can result in death. Cancer is caused by both external factors (tobacco, chemicals, radiation, and infectious organisms) and internal factors (inherited mutations, hormones, immune conditions, and mutations that occur from metabolism). The regulation of gene expression involved in cancer development has been heavily investigated, but therapeutics and methods for detecting cancer are still needed.

Cancer is considered a stem cell disease (Berns, A., *Cell*, 121:811-813 (2005)). Stem cells are characterized by self-renewal and further differentiation into multiple lineages (Bell, D. R., and Van Zant, G., *Oncogene*, 23:7290-7296 (2004)). Evidence suggests that the clonal nature of a tumor is derived from replenishment by a rare population of cancer-initiating cells, which acquire stem cell properties. Evidence also supports that the stromal region adjacent to a tumor mass may contain genetic changes within potential cancer stem cells. In contrast, the tumor mass may have DNA changes that are responsible for cancer progression but not for initiation. In addition, due to the circulating nature of blood, it is possible that chronic inflammation serves as a niche for circulating bone marrow stem or progenitor cells to mutate and develop. Thus, tumors from multiple tissues could be initiated from a similar stem cell origin, but differ only when they progress in a different environment at a later stage. Skin, lung and gastrointestinal tract are the three largest defensive surfaces of body (Berns, A., *Cell*, 121:811-813 (2005); Otto, W. R., *J Pathol*, 197:527-535 (2002)), and are underlined with enriched lymphatic tissues, which might contain stem cells derived from the circulation.

Transcriptional coactivator proteins coordinate gene expression in a large number of biological processes, including cancer development (McKenna N J, O'Malley B W, *Cell*, 108:465-474 (2002); Aranda A, Pascual A., *Physiol Rev*, 81:1269-1304 (2001)). Dysregulated coactivator functions, resulting from chromosomal aberrations in particular, have been suggested to promote oncogenesis (Yang, X. J., *Nucleic Acids Res*, 32:959-976 (2004); Greaves, M. F., Wiemels, J., *Nat Rev Cancer*, 3:639-649 (2003); Anzick, S. L., et al., *Science* 277:965-968 (1997)). Examples include coactivators CBP/p300 and TIF2, which are associated with chromosomal translocations in leukemia as fusion proteins (Yang, X. J., *Nucleic Acids Res*, 32:959-976 (2004)), and coactivators AIB1/SRC-3 and AIB3/TRBP, whose genes are amplified in breast cancers (Guan, X. Y., et al., *Cancer Res*, 56:3446-3450 (1996); Torres-Arzayus, M. I. et al., *Cancer Cell* 6:263-274 (2004)). Some oncoproteins have also been shown to have overlapping functions with coactivators (Brett, D., et al., *Hum Mol Genet*, 6:1559-1564 (1997)), implicating the involvement of transcriptional coactivator actions in cancer development.

Existing methods for detecting cancer and treating cancer typically lack specificity and are associated with adverse side effects.

Thus, it is an object of the invention to provide compositions and methods for the treatment of one or more symptoms associated with cancer.

It is another object of the invention to provide methods and compositions for the detection or diagnosis of cancer.

It is still another object to provide methods for screening for compounds that inhibit or alleviate one or more symptoms associated with pathologies due to cells having amplicons in CoAA.

SUMMARY OF THE INVENTION

It has been discovered that amplifications in the gene coactivator activator (CoAA) blocks stem cell differentiation and induce cancer stem cells. One embodiment provides compositions and methods for treating or alleviating one or more symptoms associated with a pathology such as cancer due to gene amplifications in CoAA or cells containing gene amplifications in CoAA. Representative compositions that can be used to treat one or more symptoms of a pathology due to amplifications in CoAA include, but are not limited to inhibitory nucleic acids that specifically hybridize to genomic DNA corresponding to the CoAA gene or to nucleic acids encoding CoAA or splice variants thereof, including but not limited to CoAM and CoAR, or a combination thereof. A preferred embodiment provides peptide nucleic acids that hybridized to the CoAA amplicon or to the 5' region of a CoAA amplicon.

Another embodiment provides methods and compositions for detecting cancer due to gene amplifications in CoAA or cells containing amplifications in CoAA. CoAA amplicons can be detected using a probe that hybridizes to the CoAA amplicon, for example a nucleic acid probe that hybridizes to a coding region of CoAA. An exemplary method for detecting CoAA amplicons includes, but is not limited to fluorescent in situ hybridization (FISH) analysis. The detection of one or more CoAA amplicons is indicative of cancer.

Still another embodiment provides methods for identifying compounds and biological molecules that are useful for treating cancer due to gene amplifications in CoAA. Preferably the disclosed compositions antagonize or interfere with biological activity of CoAA and/or its alternative splicing variants including, but not limited to CoAM and CoAR. One embodiment provides a method for screening for compounds that inhibit the activity of CoAA or an alternatively spliced variant thereof by treating one or more cells containing one or more CoAA amplicons with a test compound, determining the expression levels of CoAA and its alternative splicing variants including, but not limited to CoAM in the cells treated with the test compound, and selecting the test compound that inhibits the expression of CoAA or its alternative splicing variants including, but not limited to CoAM below predetermined baseline levels.

DETAILED DESCRIPTION OF THE INVENTION

Figure 1A:
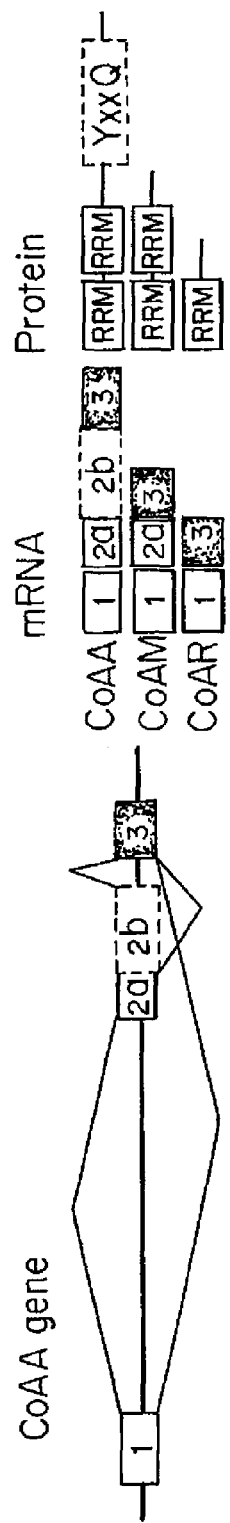
FIG. 1A is schematic representation of the CoAA gene structure. Introns are shown as lines and the three exons as numbered boxes with alternative splicing events depicted.

I. Compositions for the Treatment of Cancer

It has been discovered that amplifications in the gene coactivator activator (CoAA) blocks stem cell differentiation and induces cancer stem cells. One embodiment provides compositions and methods for treating or alleviating one or more symptoms associated with cancer due to gene amplifications in CoAA. Representative compositions for treating or alleviating one or more symptoms associated with cancer include, but are not limited to compounds that antagonize or interfere with the biological activity of CoAA or an alternatively spliced variant thereof. Preferred compositions include inhibitory nucleic acids that block expression of the CoAA amplicon or inhibitory nucleic acids that prevent expression of mRNA encoding CoAA or alternative splice variants thereof, including but not limited to CoAM and CoAR, or a combination thereof. Another embodiment provides methods and compositions for detecting cancer due to gene amplifications in CoAA. Still another embodiment provides methods for identifying compounds that are useful for treating cancer due to gene amplifications in CoAA. Preferably the disclosed compositions antagonize or interfere with the CoAA amplicons and with the biological activity of CoAA and its alternative splicing variants including, but not limited to CoAM and CoAR.

The human CoAA gene (gene symbol RBM14) is located at chromosome 11q13, a locus that has been shown to be rearranged and amplified in multiple cancers (Koreth, J. et al. *J Pathol*, 187:28-38 (1999)). Using fluorescence in situ hybridization (FISH) and qPCR analyses, it has been discovered that the CoAA gene is found to be amplified in approximately 70% of human lung cancers and a large numbers of inflammation-related cancers. Consequently, CoAA protein is overexpressed in CoAA gene-amplified tumors detected by immunohistochemistry. CoAA gene amplification is also present in chronic inflammatory lungs adjacent to the tumor mass. However, CoAA gene amplification is absent in normal lung tissues. Notably, CoAA-amplified lung cancer cells are very small, with undifferentiated morphology, and are located in stromal regions. Although the identity of these CoAA-amplified cells has not been characterized in detail, their morphology is clearly distinguished from epithelium-derived tumor cells. Thus, CoAA-amplified cancer cells are a subpopulation of undifferentiated tumor progenitors. It is believed that gene amplification is due to the redistribution of the amplified gene through asymmetric cell division (Coquelle, A. et al., *Cell*, 89:215-225 (1997)), and is a consequence of selection during tumor progression. When a number of CoAA amplicons in primary tumors are mapped, CoAA gene is found to be located at the 5' boundaries of the amplicons. The CoAA gene coding region is amplified, its 5' regulatory sequences are deleted. This is a recurrent event found in all mapped CoAA amplicons. Detailed characterization of the CoAA enhancer/promoter region suggests that loss of the 5' sequences results in altered CoAA alternative splicing, leading to high-level expression of CoAM (Yang et al., 2007).

The human CoAA gene contains three exons spanning approximately 11 Kb. The CoAA gene is alternatively spliced and produces CoAA and CoAM transcripts through competitive 5' alternative splicing events between the second and third exons (FIG. 1A) (Iwasaki, T., et al., *J Biol Chem*, 276:33375-33383 (2001); Sui, Y. et al., *Oncogene*, 26:822-835 (2007)). The resulting CoAA and CoAM proteins share two N-terminal RRM domains, but only CoAA possesses the C-terminal activation domain containing repeated YxxQ motifs (id). Consequently, CoAA is a potent transcriptional coactivator, whereas CoAM competes with CoAA via shared RRM domains and represses CoAA activities in both transcription and splicing (Iwasaki, T., et al., *J Biol Chem*, 276:33375-33383 (2001); Auboeuf, D., et al., *Science*, 298:416-419 (2002)).

Figure 1B:
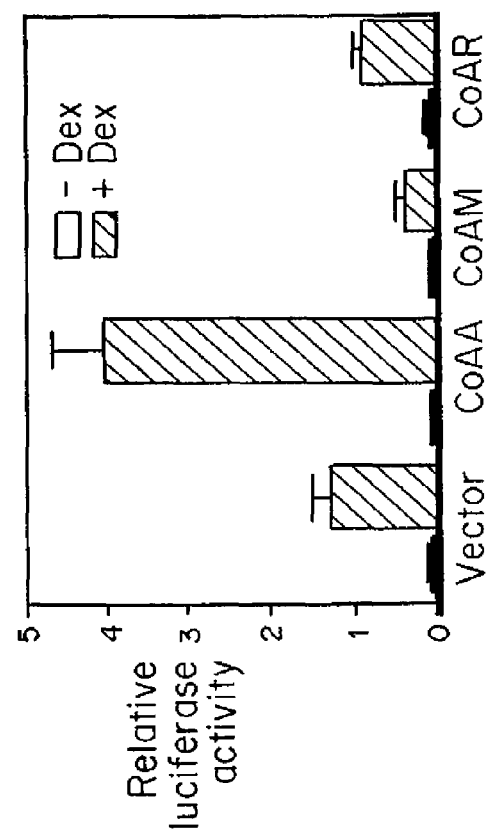
FIG. 1B is a bar graph of relative luciferase activity indicative of transcriptional activities of CoAA splicing variants analyzed in CV-1 cells, in the presence or absence of dexamethasone.

The CoAA mRNA transcript is expressed in all tissues and cells examined as shown by RT-PCR (FIG. 1B), a result consistent with previous Northern blot analysis (Iwasaki, T., et al., *J Biol Chem*, 276:33375-33383 (2001)). Sequence analyses confirmed that the observed three PCR products are the three CoAA splice variants. The CoAA transcript is relatively abundant in both normal tissues and cancer cell lines (FIG. 1B). However, the relative levels of CoAA, CoAM, and CoAR mRNAs vary between samples. In some human fetal tissues and cancer cell lines, CoAM or CoAR expression is below the limits of detection. The variation in the expression ratios of CoAA isoforms, which could partially due to the alternative splicing regulations, represents a possible cell-specific control of CoAA activity through its inhibitory splice variants.

Suitable compounds that can be used to antagonize CoAA activity or its splice variants include but are not limited to antisense nucleic acids, siRNA, microRNA, peptide nucleic acids, aptamers, and antibodies.

A. Inhibitory Nucleic Acids for the CoAA amplicon

1. Peptide Nucleic Acids

One preferred embodiment provides inhibitory nucleic acids specific to nucleic acids within or adjacent to the CoAA amplicon, preferably PNA. Peptide nucleic acids (PNAs) are compounds that in some respects are analogous to oligonucleotides, but which differ in structure. In peptide nucleic acids, the deoxyribose backbone of oligonucleotides has been replaced with a backbone having peptide linkages. Each subunit has attached a naturally occurring or non-naturally occurring base. One such backbone is constructed of repeating units of N-(2-aminoethyl)glycine linked through amide bonds.

Targeting cancer stem cells with CoAA gene amplification will reduce the chance of cancer relapse when compared to the existing treatment approaches. Radiation and chemotherapies may leave resistant cancer stem/progenitor cells behind. Surgical resection may leave cancer stem cells in the lymph node. CoAA amplification in a significant percentage of lymph nodes is also detected. Thus, CoAA amplification is a marker for cancer stem cells. Since CoAA gene amplification is present in cancer stem cells with a significant increase in copy number of the CoAA gene, PNA targeting to the CoAA gene amplicon will preferentially bind to the cancer stem cells with CoAA gene amplification but not to the normal cells.

In one embodiment the PNA hybridizes to the foreign sequence 5' to the amplicon, which is close to the CoAA promoter (FIG. 13A). This will block replication and transcription of the amplified CoAA gene but not the normal CoAA gene. However, in the event that this foreign juxtaposed sequence is not very recurrent, another strategy is to design a PNA against gap (interstitial) deletions or insertions within the amplicon to prevent amplicon DNA replication. Due to the high copy number increase of CoAA amplicon, PNA within the amplicon may have better affinity to CoAA-amplified cells. Certain potential gap deletions outside the CoAA coding region have been detected but within the amplicons (unpublished observation). These gap deletions are surprisingly recurrent in all three mapped amplicons. Gene amplification is known to be mechanistically linked to gap insertions and deletions (Coquelle, A., et al., *Cell* 89:215-225 (1997)). Therefore, these gap deletions are believed to be suitable PNA targets.

In another embodiment, the PNA compositions are designed to hybridize to the following sequence or a complement thereof:

```
                                       (SEQ ID NO: 1)
cgcggcaaccccaggcgcgggtttggacagggcttccagaatgggagg agccctgacttccaattgtacaaagttttcctgggagcccgccggtccc agcccaccgggccagagaccgccttacagactaggcctctctgccgc cggcgccgctcgcgcgcgttctcctctcttcagccctccctcttcttcc caacccctctcccgccacgggctgtggcggttggtcgtcccttcccca
```

-continued

```
cccccctcagctaacgagcgggctctaggccctctgggattggctgtgcc
tgagcacatcttccctcagcgtttctgattggtcgctggacgcgcggga
tgcgagtccccattggctaggccagggcgcctgcgcggcggggttctcg
gtcgccagccattcctgaggaggactgccggtcgttcggacgtcttgcc
tgtcgctggaggagaggtccgggctctccaggaaggtggctgcggcgac
aaaatgaagatattcgtgggcaacgtcgacggggcggatacgactccgg
ggagctggcagccctctttgcgccctacggcacggtcatgagctgcgcc
gtcatgaaacaagttcgccttcgtgcacatgcgcgagaacgcgggcgcg
ctgcgcgccatcgaagccctgcacggccacgagctgcggccggggcgcg
cgctcgtggtggagatgtcgcgcccaaggcctcttaatacttggaagat
tttcgtgggcaatgtgtcggctgcatgcacgagccaggaactgcgcagc
ctcttcgagcgccgcggacgcgtcatcgagtgtgacgtggtgaaaggta
acgcggaggcgcgctcggggcggggcgcgctcggggcactctgcctg
ttagccacgccccttacccggggtcggtcactgcgcggttgggagggg
tggggaagtgcgcgggagcaggtcggaggtgttggggcgcgttgggta
gagccaccctcctccctgcggtccaggaaccgtccaccaagtaggagg
aagcggctctgggtgggtcggcggccactgcgagccaagctacgggc
cggggacgcgcctgagagccttgcgagtgttccggggcgcgccttctc
ctggtctcctgggcctggcacccagccggaaattgggaagtgacgggcac
aagccggatcatgaagcggggaagatttctccacttccccacttcctct
ccagacgtcggtcagagcaaggagagagggaaaaggtgggggctgacgc
cccaaggccgccctcctgttccctcccgatgaatgtgctcaagcggaag
gtaacgggcccttggacgtttctcggctgggtcttttagtcttgtc
tggcatgggtctactcatgggcacagttacacgtgggtacgagaggggc
cccttccgaatcactttggcctttcaatattaggtaggttaggcgtggc
agctctgtgcttttctcctccctcaaacttggggtttttctttgggctc
gattttacatctgtcaactggaaaccccagccttttgcatgtgcaagaa
agcttgttttatgaagtccccttctgcgtagtctttacatgccaagcca
gtgccctagggcagtgtcattctttataagcttggtgactttgcaggg
gggcatactctggctgaggggtcctggggaggggtctgtgagagctct
tcattaaacagtggctaaacacggtttactgaatcagtagtagtcattg
cttgagtagtctgattctcagggcagatcccggtgccttttcttcgaga
aaaatgtgtcaccataatttaagcctgactagggacccagttgactttt
tcatagcttgagttttatcccttaagctctttatcttttacattggca
agatttggtgggacagccgttgtgtatgtggccagtctctgctccactt
gggaacagatcagagttaactttgccctgtcattttggaagatgcagcc
tgggagtatctgatgccctactcctggtgggttcatacctgctcatacc
ctgtgtgagaagtttcaggataggaaataaatgtgggtgcaagtgctt
atttatcccaccaagatatttcatttgctgtcctggaaaggcacatgtt
tggggccattcctagtcctttaagtggggaaatataaagggtcatagt
gtccactactaggaacaagtccttgttctgcattaatactgcattctat
```

```
tttcctcaactcaggttatacaagtccacgactatccggaatcgggctt
tcctgctgggtgctctgaggcaggctgtatggtgcatggattttttgctt
ttgtttagagtaaaagagtggtgggggagggtctcagattgggtacttg
tccagcaaaagggtggggtatatgagtctcatttgtgagagttttgtgt
taattgacttaccaagtttcttttgtggttgttaggtagagtggctac
taggttgagagtctagagtcaaacatctgaagggacagtctccctggaa
ctcaggcttcttgctggctttcaggtggtagagaaagtcaaaaatttgc
ctgaaatttgcttgggacccaacaccaagtgacgatgcgggtgaagtgc
ataactgcacatgaattttttagaactcctggctgactccttgtgagagt
tagacgagttttgtgcatcttgttcctttgtaaacatttgattagcaa
aaatgcattgacttactccgggagtggtggtcaactatttgcagttaca
ttgttgtgtaacagagctcctgacatacttcgatgtaagagactgggaa
agatttgaacatcatatcctccactgatgtctttttatctgtttgtgat
gacggaaagtgaggggttgaaagttgggagtgtagtagaagcgactggct
ctctaaagagcgtactcatttcttatgctgggaatggtcatttgattga
gtctccttgtgttggctgacagggctttgaaaagcacagaagcttggtg
ttgcaccagacaaccagctctgttttatttcacaggaaaaaaaaacaac
atagttgcttggttactccaggagcttagataggatttgtagaacagaa
atctcaatagcaacagtggattgtaaccactccacagcttcctcctatt
gggtgttcaaagatgaacagcttccggaaacatgtacagacttgtgggg
agatctgaaagacaaaagaggaaaatatcttctcttcatttttgtgagt
gactgtttcttcttcctatacagagctctgtagtttcaagtttaagatt
ttttcttttctttttttttttttttagacggagtctggctctgtcgcc
caggctggagtgcactggcgccatctcggctcactgcaagctccgcctc
ctgggttcacgccattctcctgcctcagcctcccgagtagctgggacta
caggcgcccgccaccacacccagctaatttttttgtatttttagtagaga
cggggtttcactgtgttagccaggatggtctcgatctcctgaccttgtg
atccgcctgcctcagcctcccaaagtgctgggattacaggcgcaagcca
ccgcgcctagccctcaagtttaagattttttagtcttaagataggagaac
ttgttttttctggattcacttaactttgttactggaggacttgtgatgcc
accagaccatttggagatctctgtaaaacattacttgatagtcccaatg
cagtgatttccttcagagtttccttgaattagatctgtgggcaagaagg
ttcctggaattttttcagatctctggttttaatggtcttaggagtacttg
ggtgttagggcatctttaatctagctaggtctgtgctttgcacttactg
tgatggggcttatcactacaggatgcagttgagttagctgggcaaccta
ttcacacttttcccctccagtgtcaggcttagaaacttcctgatacaat
ttggttataattgtatcagatggattttttaaattttgtatttattttta
tgttatttatatatttattatttttttttatgagacagagtctcattct
gttgcccaggctggagtgcagtggtgagatcttggctcactgcaacctc
cgtctcctgggttcaagcaattctcctgcctcagcctctcaagtagctg
```

-continued

```
ggtctacaggccaccacacctggctaattttttgaattttttagtagagac
agggtttcactatgttggccaggctggtcttgaactcctgacctcaggt
gatcttcctgcctcggcctcccaaagtgttgggattacaggtgtgagcc
accatgcccggcttggattttttaaattttttgatcagttataaaactca
tttgggtagtcatttgaatcatacatgtgaaatctcaattttcagattt
caccacttggtctgaataaaactcactaaggagggaaacagacagtggg
atgtccaaatgctcttgtaagcccatggaagttttttgtctcattctagt
gtcaggaagttgtggatagaataatcaggactgttagaattgttcctta
atattccctcagaatgtctggaggcccctccctgcaacaagtgcctatg
agctccagcaactctgcttcccccttcactttgggcctttctgcttgcca
tctccaggtggttttgctattcccgaggattacctcagcctctggtttt
atttttattttttattttaaagatttttttaaaatatttattcattcttta
gggtctcgctttgttgctcaggccagagtgcagtggcgtgattgtggct
cactgtagtcttgacctcctgagctcaagccatccttccacctcagtct
cccaaagtattaggattacaggaggagccaccattcctggcccagcct
ctgcttttaaagggctcttaggccacatgctggttttttgtgttttttt
tttaagcttactctattcaaagtggagatgaaggatcacaggacaactt
tagtgccttatgcctaggccaaaggaaacacgtagcttttcacaggtgg
tagataaggctctggccatgggagtgttgaggacagagttgtgataatt
cattttgttctttttttttttgagagggagtttcatccttttgccca
ggctggagtacagtggcacgatcttggctcactgcaacctccgcctccc
gggttaaagtgattctcctgcctcggcttcttgagtagctgggattaca
ggcacatgccaccacgcccggctaatttaatattttagtaaagacggc
gtttcaccttgttggtcaggctggtcttgaactcctgacctcaggtggt
ccgcctgcctcggcctcccaaagtgctgggattatggtgtgagtcatt
gcgcctggtctcattgtgttcttttatcgtctgtgccagcttctaagtt
tgcatggcattgtgttttgcttgagatgaaagataatattctatagga
aataaatctctggttatttctaggtttgaataatcataattccttattc
tgtagctgttcatatcttacaaggcacttttgtctttctcttgaacct
cttaactttgaggtaggtaggatagatgtgtcggaggaaatacatggta
agtttctttttatttttttgagacggagttttgcgcttgtcacccagg
ctggagtgcagtgatcttggctcactgcagcctccttcttttttcttccg
ggttcaagtgattctcctccctcagcctctggagtagctgggattacag
gtgccagccaccacgccctggtaattttgtattttagtagagacgtg
gtttcaccatgttggccaggctggtctggaattcctgacctcaggtgat
ccacccacctgggcttcctaaagtgttgggattacatgcgtgagccacc
gtgcttggctagttctttttctttttttttcttttttttttttttgaaat
ggagtcttgctgtgtcacccagactggagtacggtggtgccatttcggc
tcactgcaacttccacctcccaggttcaagtgattctcctgccccagag
cctcctgagtagctggaattataggtgtgcaccaccacacctagctaat
ttttgtattttagtagagacagggtttcaccatgttggtcaggctgat
```

```
cttgaactcctgatctcaggtgatctgcctgccttggcctcccaaagcc
ctggcatgagcccctgtacctgcctaaatggtaagtttcctaagatctt
ataacaagtcagtgatacctgggtctggaactgagaccattgaatttct
aattaaggatccctttgtgctatgccacacttctgacttctacttatt
gattgcattttttccccattatccttagtcttgtgtcattgtcttcaaa
tccaggaaatgacttgttctgtaggagcagctagataaggcatcccag
tacgaaagtttctaaaaatgaggaccccttgtttggaggttattaagaat
gtttcttatcttagtattgtcatctgggtagctctttgtttcttaagct
gatgtgacagatagcatcctggtacttggatgctatctaagagtagcca
caggtcgagaatggagctaagcttagagccttatttcctaggggcagga
ttctctccttcagattctgcctgtgctttgtgagtgtggacatgagaat
ttctttccattccttcattccctgaagttttctccttctgtgtagtaga
taagtatagctttgagaccggcatcctgtcttctcctaccacagcttat
tcaggtcataatgagagctgcaggggtaacctggttagcagagcctgtt
agctgcagtaattgcagcttcatacccttataggtgagaaaccagatctt
tctggtaagcagtctgctctgtgaacagaagcccaaggtgtaaggtata
cctctgtcccttaaagaggaaacagtggaggatgcagtgtggtctggga
caggggggattgggcatgaactcagccagtgggcttagtttctattccca
tacctcattggcttacacagggtccatcttctctgcttctaagcctaaa
ttttagtcatattacacagtcctgccttatacctttgacttctcaggga
tagattatgtagcaaagggcattggaagagctgtgattctggtcctga
ctcaacacactttgagtggggcaagccatataaaaactcttgagcatg
tatgtccacctgttaaatggaggtaatgattcttgccctgcctacctc
acaggattgtgaggcccaaatgaggtcctcctgtacctaagagtgctttt
gaaaacttgggaagtactgtgaaaaagcggagagatcatattggaatgt
tgtgaactgcttgcttgttgcagtctatctctcttgccttaattggaca
tgggctgagagatgggtcataccaaaacgtgagtggtcatttccagtgt
ttgagagttaggcctcaaaagtgagctaggcctcaaaggtgtttggtga
gtttgggttgagaacactgaagaactgagtgatctaggaacgctttctg
cattttgttctgctggtttgtacttacaggagatgtgaagatttttatc
ctgtgttgcagttcatctttgctccttcttctctcaccaggaagttggg
tgagatggcagggtttgtaaaggggagaatgggaagaaggctgtaggca
aagatgactgcttgggacagtcagaagctttgttatatgggagctacat
tttatgacatactcctggagaggagggtttggaggccttggaggtagct
ggcaacagctgggtgctgttgtgtgtccaatttgggacccatcaggtag
catgccctgcccccctaattgctaaccctctgtctgctgctttatcaga
ctacgcgtttgttcacatggagaaggaagcagatgccaaagccgcaatc
gcgcagctcaacggcaaagaagtgaagggcaagcgcatcaacgtggaac
tctccaccaagggtcagaagaaggggcctggcctggctgtccagtctgg
ggacaagaccaagaaaccaggggctggggatacggccttccctggaact
```

-continued ggtggcttctctgccaccttcgactaccagcaggcttttggcaacagca
ctggtggctttgatgggcaagcccgtcagcccacaccacccttctttgg
tcgcgaccgcagccctctgcgccgttcacctccccgagcctcttatgtg
gctcctctgacgggcccagccagctacctaccgggcccagccgtcgtgt
cactgggagctgcctacagggcccagccttctgcctcttgggtgttgg
ctatcggactcagcccatgacagcccaggcagcctcttaccgcgctcag
ccctctgtctcccttggggcaccatacaggggccagctggctagtccta
gctcccagtctgctgcagcttcttcactcggcccatatggtggagccca
gccctcagcctcggcccttcctcctatgggggtcaggcagctgcagct
tcttcgctcaactcctatgggctcagggttcctcccttgcctcctatg
gtaaccagccatcctcttacgcgcccaggctgcctcttcctatgggt
tcgtgcagctgcttcttcctacaacacccagggagcagcttcctcctta
ggctcctacggggctcaggcagcctcctatggggcccagtctgcagcct
cctcactagcttatggagcccaggcagcttcatataatgcccagccctc
ggcctcttacaatgcccagtctgccccatatgctgcacagcaggctgct
tcctactcttcccaacctgctgcctatgtggcacagccagccacagctg
ctgcctatgccagccagccagcagcctacgccgcacaagccactacccc
aatggctggctcctatggggcccagccggttgtgcagacccagctgaat
agttacggggcccaagcatcaatgggcctttcaggctcctatgggctc
agtcggctgctgcggccactggctcctatggtgccgcagcagcctacgg
ggcccaaccttctgccaccctggcagctcttaccgcactcagtcatca
gcctcattggctgcttcctatgctgcccagcagcatccccaggctgctg
cctcctaccgcggccagccaggcaatgcctacgatggggcaggtcagcc
gtctgcagcctacctgtccatgtcccaggggggccgttgccaacgccaac
agcacccccgccgccctatgagcgtacccgcctctccccaccccgggcca
gctacgacgatccctacaaaaaggctgtcgccatgtcgaaaaggtactg
tatgcccccccgcctctgccccagctggggcttagggcaaggggctga
ggttggcatgggagggaaactggaggcatcggcccctccctcggtcttc
tcttctctattttgtgggatgtccagaggccgagggagcagtgtcta
tgaactttcctggtcaccagggttcaggtggagcatagtgctcagcctg
gggtggtacctgctagtcaggccaggcacagtgtcacctgtctaggcta
gcccaagtgtcattggagctactgcctgcaggactgtggcccatatcct
ttcccactgtctcaaggatccttaagcctattacgtggttgtcctggct
ttggcagggatgtgggttaaagagtagtccctttggcattcactggcta
aaggcaagtttacgaggtgcgtccactctgggaagttggggacctcgct
ttcatccgccgttctgttgataaacaaccaaggtcttctctgcaggc
ccaggggcggagatagtttgctgtggtgtgggaatgtagaccaaaatcc
accttggctagttcagaggggaggacttcagtggagggtttgatttccc
actgagttgaagccaggcttgattttttttggcctggatagggtgatgag
ccttctgacaaaaggagaccaatctcttggagaccactgtgatcacacc
ctccctgtccccattggcatctccccaatgcccacctggagtcctcccc -continued tcaattgtctcattcaccaactgtcttcttctctcgactaggtatggtt
ccgaccggcgtttagccgagctctctgattaccgccgtttatcagagtc
gcagctttcgttccgccgctcgccgacaaagtcctcgctggattaccgt
cgcctgcccgatgcccattccgattacgcacgctattcgggctcctata
atgattacctgcgggcggctcagatgcactctggctaccagcgccgcat
gtagggccatcctgggatggggcaccacagggagggagggagaaaagag
gtgggtagggttacagatccaggttataactactctggcccatacctttt
cctggttgtggttttttcatgccctctaccatgtgggccttccccaggag
atgatcctgttaagtgttcggcagtaacctactttgttccttcgcctca
gcagcaaatcttgctactggctctagatctgcggtttcccctctaccct
gcctcccgtctccccagaatgggaatttcttttatgttttattttttt
cctggctccctttatttttgtgcgcgatatttaaggtcgtctggatgg
ggaagcaacctgcagctgaggtcgccggcgcctttttctttttagatgg
gaaggaggccaggaaagggtcagcttaaccatttcctatgtgccaagct
gtgccagcagtccagggtaccctgactgtccctctgtagactgttgaga
ctgagttcctgttgggacagtcagttggtatgtatccaagtccctgctg
accactaatgttctagctgatggtgagcggcacagtcccacttccccat
ctccccaagtaggtggtgttagaaaaccttaatttttttttccctttgt
atggactacaaataaaacttggggcaatttgcagtttggaaacctggtt
gtcattgtcttgattgcattcagtgtcaaaggagccaatttgacatcca
ggaagacatgatagctaaaggaaggcagtcagagaacccaggactggt
gaggaaaggggtttgaatgtcggaattagaaggattgccctgtggccca
gaaggatttagctcatcgtcgtcctgctagcctgccatctttcagactt
tccagggcaggtggcctggtcctcagcccctcaacttgagttagtcacac
caaaatgcagtaaatgatgcccatttttcctctgcctgtgcttgaccatt
ttcactgacttttctccagttcaggaataacctgtgttccaatgggatg
gttctggggtttggcctcttaggaagtggggaatgggctgctgtggtat
ttacaggctagtagatcctttaggcagtaggctggaatgagtgctgggg
ctgggacccagaaaggaaccagtagtggagtgggggtaatggcgttgcc
tgatactgccctatggttggaataaggaagggcagagaaaacttgaagc
aggtatggggcattctggccatagagctcgtatttgcctgttgagctg
taccatggagcatcctcctgtgtcctgccaacccctgccattatagtca
ccggagactcctttacctatccctatctgttagggttttcagatgtcct
ctcgctgggtttatatttgaaggtatagaatctgggaaagggtggggtg
caagctaaccaaataggatgctagggttgggtggggaattgaggactc
ttctgtgcttttattgtagggctggggatcgaggatctgggcaaaaaat
atgacatttccaaccagggacaaaatggaggcttgggcttagtgatggg
taaatggaagactggttgagtgggatgataatgggagaacttactgatg
ctcttttgggaaaaggtgcttaaagactcgatttgggagcctactggg
gcaaggcgactggggaggtgtacgtgttagtcaagtggaggtcaggtgg

```
gttatcttctgcctccttcactggcttcatgtgaacttgcctgtgacag aatatcttgccctagatgtcctcttccctcttgccatcgtgcaaaagca ttcgatcttatgaccgtgagttcttatttgtggatgctaactggggtaa tctcagggagtactggggccatggctctttcccttgctctctttctgc tcactgctttgctttcaggtgcttagctgctcctttttatttctttgca ggactgggaaagcatgggaggaggattttgataagtttcttgttctctg cgtggtgatgggtggtctgagggccaagttaataagcctacctttggt tattaccctggaaaattgagggttgatggtagggttatgattgtggcct gtgtatttgcaattttctttgtcagtgtggctttctgtcatcttcctt tttctccagtgagggttctgccactgtctcaatcccttggttcctgcaa aaaacagctaaatgtgctctcagggccagtggtgatgttctgtgttgca gccccagctcttgaaagtgacctggcccagatgagctctgcctgcttgt catctttaggtcctgctgccctgctgcctcagccctcaggctcctaac tgctcaagccagaaggagctacaaagccaaatcatttgtcattttctc tggcagattgttttaaaatctccctccctcttttattttaattatgcc acctgtgttaatc
```

Another embodiment provides a PNA conjugate containing a targeting moiety and optionally a cell penetrating peptide. For example: NH$_2$-RRRRRRRQIKIWFQNRRM-KWKKGGC-s-s-K-GCC CAC GAA TAT CTT CAT-KKK-CONH$_2$ (SEQ ID NO:2). The targeting moiety targets the PNA to a cancer cell, preferably a cancer cell having one or more CoAA amplicons. The targeting moiety can be a binding moiety that binds to a tumor specific antigen. Alternatively, the binding moiety can be folate. The targeting moiety and/or the cell penetrating peptide can be linked to the PNA via a spacer.

2. Aptamers

One embodiment provides an aptamer that specifically binds to a nucleic acid within or adjacent to the CoAA amplicon. In one embodiment the aptamer binds to a CoAA amplicon. An "aptamer" refers to a nucleic acid molecule that is capable of binding to a particular molecule of interest with high affinity and specificity (Tuerk and Gold, *Science* 249:505 (1990); Ellington and Szostak, *Nature* 346:818 (1990)). The binding of an aptamer to amplified CoAA gene will block the gene activity in cancer stem cells with CoAA gene amplification. This will eliminate the cancer stem cells in the tumor tissue, and achieve the goal of the treatment of cancer.

B. Inhibitory Nucleic Acids for CoAA and Splice Variants Thereof

The inhibitory nucleic acid is preferably an antisense nucleic acid that hybridizes to a nucleic acid encoding CoAA or splice variants thereof including, but not limited to CoAM and CoAR or a combination thereof. The hybridization preferably occurs intracellularly and is sufficient to inhibit expression of the nucleic acid encoding CoAA or a splice variant thereof.

1. Antisense Nucleic Acids

The disclosed antisense nucleic acids hybridize to mRNA encoding CoAA or a splice variant thereof including, but not limited to CoAM and CoAR. Antisense nucleic acids include but are not limited to peptide nucleic acids, aptamers, and siRNA. In one embodiment the antisense nucleic acids hybridize to the following sequence or a complement thereof:

```
                                              (SEQ ID NO: 3)
agccattcctgaggaggactgccggtcgttcggacgtcttgcctgtcgc tggaggagaggtccgggctctccaggaaggtggctgcggcgacaaaatg aagatattcgtgggcaacgtcgacggggcggatacgactccggaggagc tggcagccctctttgcgccctacggcacggtcatgagctgcgccgtcat gaaacagttcgccttcgtgcacatgcgcgagaacgcgggcgcgctgcgc gccatcgaagccctgcacggccacgagctgcggccggggcgcgcgctcg tggtggagatgtcgcgcccaaggcctcttaatacttggaagattttcgt gggcaatgtgtcggctgcatgcacgagccaggaactgcgcagcctcttc gagcgccgcggacgcgtcatcgagtgtgacgtggtgaaagactacgcgt ttgttcacatggagaaggaagcagatgccaaagccgcaatcgcgcagct caacggcaaagaagtgaagggcaagcgcatcaacgtggaactctccacc aagggtcagaagaaggggcctggcctggctgtccagtctggggacaaga ccaagaaaccaggggctggggatacggccttccctggaactggtggctt ctctgccaccttcgactaccagcaggcttttggcaacagcactggtggc tttgatgggcaagcccgtcagcccacaccaccttctttggtcgcgacc gcagccctctgcgccgttcacctccccgagcctcttatgtggctcctct gacggcccagccagctacctacgggcccagccgtccgtgtcactggga gctgcctacagggccagccttctgcctctttgggtgttggctatcgga ctcagcccatgacagcccaggcagcctcttaccgcgctcagccctctgt ctccctggggcaccatacaggggccagctggctagtcctagctcccag tctgctgcagcttcttcactcggcccatatggtggagcccagccctcag cctcggcctttcctcctatgggggtcaggcagctgcagcttcttcgct caactcctatgggctcagggttcctcccttgcctcctatggtaaccag ccatcctcttacggcgcccaggctgcctcttcctatggggttcgtgcag ctgcttcttcctacaacacccagggagcagcttcctccttaggctccta cggggctcaggcagcctcctatggggcccagtctgcagcctcctcacta gcttatggagcccaggcagcttcatataatgcccagccctcggcctctt acaatgcccagtctgccccatatgctgcacagcaggctgcttcctactc ttcccaacctgctgcctatgtggcacagccagccacagctgctgcctat gccagccagccagcagcctacgccgcacaagccactacccaatggctg gctcctatggggcccagccggttgtgcagacccagctgaatagttacgg ggcccaagcatcaatgggcctttcaggctcctatggggctcagtcggct gctgcggccactggctcctatggtgccgcagcagcctacggggcccaac cttctgccaccctggcagctccttaccgcactcagtcatcagcctcatt ggctgcttcctatgctgcccagcagcatcccaggctgctgcctcctac cgcggccagccaggcaatgcctacgatggggcaggtcagccgtctgcag cctacctgaccatgtcccagggggccgttgccaacgccaacagcacccc gccgccctatgagcgtacccgcctctccccacccggggccagctacgac gatccctacaaaaaggctgtcgccatgtcgaaaaggtatggttccgacc ggcgtttagccgagctctctgattaccgccgtttatcagagtcgcagct
```

-continued
```
ttcgttccgccgctcgccgacaaagtcctcgctggattaccgtcgcctg cccgatgcccattccgattacgcacgctattcgggctcctataatgatt acctgcgggcggctcagatgcactctggctaccagcgccgcatgtaggg ccatcctgggatggggcaccacagggagggagggagaaaagaggtgggt agggttacagatccaggttataactactctggcccatacctttcctggt tgtggtttttcatgccctctaccatgtgggccttccccaggagatgatc ctgttaagtgttcggcagtaacctactttgttccttcgcctcagcagca aatcttgctactggctctagatctgcggtttccctctaccctgcctcc cgtctcccagaatgggaatttcttttatgttttttattttttcctggc tccttttattttgtgcgcgatatttaaggtcgtctggatggggaagc aacctgcagctgaggtcgccggcgcctttttcttttagatgggaagga ggccaggaaagggtcagcttaaccatttcctatgtgccaagctgtgcca gcagtccagggtaccctgactgtccctctgtagactgttgagactgagt tcctgttgggacagtcagttggtatgtatccaagtccctgctgaccact aatgttctagctgatggtgagcggcacagtcccacttccccatctcccc aagtaggtggtgttagaaaaccttaatttttttccctttgtatggac tacaaataaaacttggggcaatttgcagtttggaaaa
``` a. Peptide Nucleic Acids

One embodiment provides peptide nucleic acids specific to nucleic acids that encode CoAA or a splice variant thereof. CoAM, CoAR, or a combination thereof, preferably hybridizing to mRNA. Peptide nucleic acids are described above. Exemplary anti-sense PNA sequences targeted to CoAM, CoAA, or both of them are shown in FIG. 13B. The PNAs specific to CoAA, CoAM, or CoAR mRNA can be conjugated to an optional targeting moiety and/or an optional a cell penetrating peptide. An exemplary cell penetrating peptide includes, but is not limited to NH$_2$-RRRRRRQIKIWFQNRRMKWKKGGC-s-s-K-CGC CGG TCG GAA CCA TAC-KKK-CONH$_2$ (SEQ ID NO:4). The targeting moiety targets the PNA to a cancer cell, preferably a cancer cell having one or more CoAA amplicons. The targeting moiety can be a binding moiety that binds to a tumor specific antigen. Alternatively, the binding moiety can be folate.

b. Aptamers

One embodiment provides an aptamer that specifically binds to a nucleic acid encoding CoAM. An "aptamer" refers to a nucleic acid molecule that is capable of binding to a particular molecule of interest with high affinity and specificity (Tuerk and Gold, *Science* 249:505 (1990); Ellington and Szostak, *Nature* 346:818 (1990)). The binding of a ligand to an aptamer, which is typically RNA, changes the conformation of the aptamer and the nucleic acid within which the aptamer is located. The conformation change inhibits translation of an mRNA in which the aptamer is located, for example, or otherwise interferes with the normal activity of the nucleic acid. Aptamers may also be composed of DNA or may comprise non-natural nucleotides and nucleotide analogs. An aptamer will most typically have been obtained by in vitro selection for binding of a target molecule. However, in vivo selection of an aptamer is also possible.

Aptamers have specific binding regions which are capable of forming complexes with an intended target molecule in an environment wherein other substances in the same environment are not complexed to the nucleic acid. The specificity of the binding is defined in terms of the comparative dissociation constants (Kd) of the aptamer for its ligand as compared to the dissociation constant of the aptamer for other materials in the environment or unrelated molecules in general. Typically, the Kd for the aptamer with respect to its ligand will be at least about 10-fold less than the Kd for the aptamer with unrelated material or accompanying material in the environment. Even more preferably, the Kd will be at least about 50-fold less, more preferably at least about 100-fold less, and most preferably at least about 200-fold less.

An aptamer will typically be between about 10 and about 300 nucleotides in length. More commonly, an aptamer will be between about 30 and about 100 nucleotides in length.

c. siRNA to CoAA or Alternative Splice Variants Thereof

Inhibitory nucleic acids specific to CoAA or splice variants thereof can be siRNA or microRNA that hybridize to mRNA encoding CoAA or splice variants thereof and inhibit the expression of the mRNA. In one embodiment, siRNA are designed to hybridize to cDNA corresponding to SEQ ID NO:3 or a complement thereof. Small RNA molecules are single stranded or double stranded RNA molecules generally less than 200 nucleotides in length. Such molecules are generally less than 100 nucleotides and usually vary from 10 to 100 nucleotides in length. In a preferred format, small RNA molecules have 11, 12, 13, 14, 15, 16, 17, 18, 19, 20, 21, 22, 23, 24, 25, 26, 27, 28, 29 or 30 nucleotides. Small RNAs include microRNAs (miRNA) and small interfering RNAs (siRNAs). MiRNAs are produced by the cleavage of short stem-loop precursors by Dicer-like enzymes; whereas, siRNAs are produced by the cleavage of long double-stranded RNA molecules. MiRNAs are single-stranded, whereas siRNAs are double-stranded.

The term "siRNA" means a small interfering RNA that is a short-length double-stranded RNA that is not toxic. Generally, there is no particular limitation in the length of siRNA as long as it does not show toxicity. "siRNAs" can be, for example, 15 to 49 bp, preferably 15 to 35 bp, and more preferably 21 to 30 bp long. Alternatively, the double-stranded RNA portion of a final transcription product of siRNA to be expressed can be, for example, 15 to 49 bp, preferably 15 to 35 bp, and more preferably 21 to 30 bp long. The double-stranded RNA portions of siRNAs in which two RNA strands pair up are not limited to the completely paired ones, and may contain nonpairing portions due to mismatch (the corresponding nucleotides are not complementary), bulge (lacking in the corresponding complementary nucleotide on one strand), and the like. Nonpairing portions can be contained to the extent that they do not interfere with siRNA formation. The "bulge" used herein preferably comprise 1 to 2 nonpairing nucleotides, and the double-stranded RNA region of siRNAs in which two RNA strands pair up contains preferably 1 to 7, more preferably 1 to 5 bulges. In addition, the "mismatch" used herein is contained in the double-stranded RNA region of siRNAs in which two RNA strands pair up, preferably 1 to 7, more preferably 1 to 5, in number. In a preferable mismatch, one of the nucleotides is guanine, and the other is uracil. Such a mismatch is due to a mutation from C to T, G to A, or mixtures thereof in DNA coding for sense RNA, but not particularly limited to them. Furthermore, in the present invention, the double-stranded RNA region of siRNAs in which two RNA strands pair up may contain both bulge and mismatched, which sum up to, preferably 1 to 7, more preferably 1 to 5 in number.

The terminal structure of siRNA may be either blunt or cohesive (overhanging) as long as siRNA can silence, reduce, or inhibit the target gene expression due to its RNAi effect. The cohesive (overhanging) end structure is not limited only to the 3' overhang, and the 5' overhanging structure may be included as long as it is capable of inducing the RNAi effect. In addition, the number of overhanging nucleotide is not limited to the already reported 2 or 3, but can be any numbers as long as the overhang is capable of inducing the RNAi effect. For example, the overhang consists of 1 to 8, preferably 2 to 4 nucleotides. Herein, the total length of siRNA having cohesive end structure is expressed as the sum of the length of the paired double-stranded portion and that of a pair comprising overhanging single-strands at both ends. For example, in the case of 19 bp double-stranded RNA portion with 4 nucleotide overhangs at both ends, the total length is expressed as 23 bp. Furthermore, since this overhanging sequence has low specificity to a target gene, it is not necessarily complementary (antisense) or identical (sense) to the target gene sequence. Furthermore, as long as siRNA is able to maintain its gene silencing effect on the target gene, siRNA may contain a low molecular weight RNA (which may be a natural RNA molecule such as tRNA, rRNA or viral RNA, or an artificial RNA molecule), for example, in the overhanging portion at its one end.

In addition, the terminal structure of the "siRNA" is not necessarily the cut off structure at both ends as described above, and may have a stem-loop structure in which ends of one side of double-stranded RNA are connected by a linker RNA. The length of the double-stranded RNA region (stem-loop portion) can be, for example, 15 to 49 bp, preferably 15 to 35 bp, and more preferably 21 to 30 bp long. Alternatively, the length of the double-stranded RNA region that is a final transcription product of siRNAs to be expressed is, for example, 15 to 49 bp, preferably 15 to 35 bp, and more preferably 21 to 30 bp long. Furthermore, there is no particular limitation in the length of the linker as long as it has a length so as not to hinder the pairing of the stem portion. For example, for stable pairing of the stem portion and suppression of the recombination between DNAs coding for the portion, the linker portion may have a clover-leaf tRNA structure. Even though the linker has a length that hinders pairing of the stem portion, it is possible, for example, to construct the linker portion to include introns so that the introns are excised during processing of precursor RNA into mature RNA, thereby allowing pairing of the stem portion. In the case of a stem-loop siRNA, either end (head or tail) of RNA with no loop structure may have a low molecular weight RNA. As described above, this low molecular weight RNA may be a natural RNA molecule such as tRNA, rRNA or viral RNA, or an artificial RNA molecule.

Methods for designing siRNA are known in the art. For example, web sites offer free software for designing siRNA using a known target sequence, for example SEQ ID NO:3.

2. Antibodies Specific for CoAM

Antibodies may be raised against any portion of the CoAM protein which provides an antigenic epitope that is unique to the CoAM protein. In one embodiment, the presently disclosed antibodies specifically bind to an epitope unique to CoAM. In one embodiment the antibody binds an epitope form by the amino acid sequence MVPTGV (SEQ ID NO:5).

Intact antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains (Clothia et al., *J. Mol. Biol.*, 186: 651 663 (1985); Novotny and Haber, *Proc. Natl. Acad. Sci. USA*, 82: 4592 4596 (1985)).

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgA1 and IgA2 for IgA; IgG1, IgG2, IgG3, IgG4 for IgG in humans, and IgG1, IgG2a, IgG2b, and IgG3 for IgG in mouse. The heavy-chain constant domains that correspond to the major classes of immunoglobulins are called α, δ, ε, γ, and μ, respectively. The subunit structures and three-dimensional configurations of different classes of immunoglobulins are well known in the art.

For a review of the antibody structure, see Antibodies: A Laboratory Manual, Cold Spring Harbor Laboratory, eds. Harlow et al., 1988. Briefly, each light chain is composed of an N-terminal variable (V) domain ($V_L$) and a constant (C) domain ($C_L$). Each heavy chain is composed of an N-terminal V domain, three or four C domains, and a hinge region. The $C_H$ domain most proximal to $V_H$ is designated as $C_{H1}$. The $V_H$ and $V_L$ domain consist of four regions of relatively conserved sequence called framework regions (FR1, FR2, FR3, and FR4), which form a scaffold for three regions of hypervariable sequence (complementarity determining regions, CDRs). The CDRs contain most of the residues responsible for specific interactions with the antigen. CDRs are referred to as CDR1, CDR2, and CDR3. Accordingly, CDR constituents on the on the heavy chain are referred to as H1, H2, and H3, while CDR constituents on the light chain are referred to as L1, L2, and L3. CDR3 is the greatest source of molecular diversity within the antibody-binding site. H3, for example, can be as short as two amino acid residues or greater than 26. The locations of immunoglobulin variable domains in a given antibody may be determined as described, for example, in Sequences of Proteins of Immunological Interest, US Department of Health and Human Services, eds. Kabat et al., 1991.

Antibody diversity is created by the use of multiple germline genes encoding variable regions and a variety of somatic events. The somatic events include recombination of variable gene segments with diversity (D) and joining (J) gene segments to make a complete $V_H$ region and the recombination of variable and joining gene segments to make a complete $V_L$ region. The recombination process itself is imprecise, resulting in the loss or addition of amino acids at the V(D)J junctions. These mechanisms of diversity occur in the developing B cell prior to antigen exposure. After antigenic stimulation, the expressed antibody genes in B cells undergo somatic mutation. Based on the estimated number of germline gene segments, the random recombination of these segments, and random $V_H$ $V_L$ pairing, up to $1.6 \times 10^7$ different antibodies could be produced (Fundamental Immunology, 3rd ed., ed. Paul, Raven Press, New York, N.Y., 1993). When other processes which contribute to antibody diversity (such as somatic mutation) are taken into account, it is thought that upwards of $1 \times 10^{10}$ different antibodies could be generated (Immunoglobulin Genes, 2nd ed., eds. Jonio et al., Academic Press, San Diego, Calif., 1995). Because of the many processes involved in generating antibody diversity, it is unlikely that independently derived monoclonal antibodies with the same antigen specificity will have identical amino acid sequences.

One of skill in the art will recognize that the disclosed antibodies may contain any number of conservative or non-conservative changes to their respective amino acid sequences without altering their biological properties. Changes can be made in either the framework (FR) or in the CDR regions. While changes in the framework regions are usually designed to improve stability and immunogenicity of the antibody, changes in the CDRs are usually designed to increase affinity of the antibody for its target. Such affinity-increasing changes are typically determined empirically by altering the CDR region and testing the antibody. Such alterations can be made according to the methods described in Antibody Engineering, 2nd. ed., Oxford University Press, ed. Borrebaeck, 1995. Conservative amino acid modifications are based on the relative similarity of the amino acid side-chain substituents, for example, their hydrophobicity, hydrophilicity, charge, size, and the like. Exemplary conservative substitutions which take some of the foregoing characteristics into consideration are well known to those of skill in the art and include: arginine and lysine; glutamate and aspartate; serine and threonine; glutamine and asparagine; and valine, leucine, and isoleucine. Further details on such changes are described in the following sections. Unlike in CDRs, more substantial non-conservative changes in structure framework regions (FRs) can be made without adversely affecting the binding properties of an antibody. Changes to FRs include, but are not limited to, humanizing a non-human derived framework or engineering certain framework residues that are important for antigen contact or for stabilizing the binding site, e.g., changing the class or subclass of the constant region, changing specific amino acid residues which might alter an effector function such as Fc receptor binding (Lund et al. (1991) J. Immun. 147: 2657 2662 and Morgan et al. (1995) Immunology 86: 319 324), or changing the species from which the constant region is derived.

The disclosed antibodies include polyclonal antibodies, monoclonal antibodies, antibody compositions, antibodies having mono- or poly-specificity, humanized antibodies, single-chain antibodies, CDR-grafted antibodies, antibody fragments such as Fab, F(ab')$_2$, Fv, and other antibody fragments which retain the antigen binding function of the parent antibody. The disclosed antibodies may also be modified to chimeric antibodies. For instance, a human Fc region can be fused to a CoAM binding region from a murine antibody to generate a chimeric antibody. By replacing other portions of the murine antibody (outside of the antigen binding region) with corresponding human antibody fragments, a humanized antibody may be produced. Such chimeric or humanized antibodies may display enhanced biological specificity or in vivo stability. They are particularly useful in designing antibodies for human therapies. It is understood that practitioners are familiar with the standard resource materials which describe specific conditions and procedures for the construction, manipulation, production, and isolation of antibodies (see, for example, Harlow and Lane (1988) Antibodies: A Laboratory Manual, Cold Spring Harbor Press, Cold Spring Harbor, N.Y.).

Another embodiment provides cells, such as hybridomas, that produce any of the presently disclosed antibodies. One of skill in the art is familiar with the many cells that are suitable for producing antibodies. Any cell may be used to produce the presently disclosed antibodies. In an embodiment, the presently disclosed antibodies are produced by a hybridoma cell.

In one embodiment the anti-CoAM antibody is operably linked to cell penetrating peptide also referred to as a protein transduction domain. Operably linked means that the peptide is joined to the antibody such that both the antibody and the cell penetrating peptide retain their biological functions. For example the cell penetrating peptide will function to deliver the antibody to the interior of a cell. The antibody will retain its ability to bind to CoAM.

II. Diagnostics for and Methods of Diagnosing Cancer

The disclosed compositions can be used in diagnostic assays, screening assays, and in therapeutic applications. In some embodiments, the compositions are used as diagnostic markers for the detection of cancer due to gene amplification of CoAA. Representative cancers include, but are not limited to those listed in Table 1. Detection of CoAA gene amplification or elevated expression of CoAM in tissue or subjects allows for a determination or diagnosis of cancer. To detect or diagnose cancer, baseline values for the expression or activity of CoAM are established in order to provide a basis for the diagnosis and/or prognosis of cancer in a patient. In some embodiments, this is accomplished by combining body fluids, tissue biopsies, or cell extracts taken from normal subjects (cancer-free subjects) with one or more antibody(ies) to a CoAM under conditions suitable for complex formation. Such conditions are well known in the art. The amount of standard complex formation may be quantified by comparing levels of antibody-target complex in the normal sample with a dilution series of positive controls, in which a known amount of antibody is combined with known concentrations of purified CoAM. Standard values obtained from normal samples may be compared with values obtained from samples from subjects suspected of having cancer. Deviation between standard and subject values establishes the presence of or predisposition to the disease state.

In other embodiments, the expression levels of CoAA splice variants are determined for different cellular states in the cancer phenotype; that is, the expression levels of genes in cancer-free tissue and in cancer tissue are evaluated to provide expression profiles. An expression profile of a particular cell state or point of development is essentially a "fingerprint" of the state; while two states may have any particular gene similarly expressed, the evaluation of a number of genes simultaneously allows the generation of a gene expression profile that is unique to the state of the cell. By comparing expression profiles of cells in different states, information regarding which genes are important (including both up- and down-regulation of genes) in each of these states is obtained. Then, diagnosis may be done or confirmed by determining whether or not the tissue from a particular patient has the gene expression profile of normal or cancerous tissue.

"Differential expression," or grammatical equivalents as used herein, refers to both qualitative as well as quantitative differences in the genes' temporal and/or cellular expression patterns within and among the cells. Thus, a differentially expressed gene can qualitatively have its expression altered, including an activation or inactivation, in, for example, normal versus lymphoma tissue. That is, genes may be turned on or turned off in a particular state, relative to another state. As is apparent to the skilled artisan, any comparison of two or more states can be made. Such a qualitatively regulated gene will exhibit an expression pattern within a state or cell type which is detectable by standard techniques in one such state or cell type, but is not detectable in both. Alternatively, the determination is quantitative in that expression is increased or decreased; that is, the expression of the gene is either upregulated, resulting in an increased amount of transcript, or downregulated, resulting in a decreased amount of transcript. The degree to which expression differs need only be large enough to quantify via standard characterization techniques as outlined below, such as by use of Affymetrix GeneChip™. expression arrays, Lockhart, *Nature Biotechnology,* 14:1675-1680 (1996). Other techniques include, but are not limited to, quantitative reverse transcriptase PCR, Northern analysis and RNase protection. As outlined above, preferably the change in expression (i.e. upregulation or downregulation) is at least about 50%, more preferably at least about 100%, more preferably at least about 150%, more preferably, at least about 200%, with from 300 to at least 1000% being especially preferred.

As will be appreciated by those in the art, this may be done by evaluation at either the gene transcript, or the protein level; that is, the amount of gene expression may be monitored using nucleic acid probes to the DNA or RNA equivalent of the gene transcript, and the quantification of gene expression levels, or, alternatively, the final gene product itself (protein) can be monitored, for example through the use of antibodies to the CoAM protein and standard immunoassays (ELISAs, etc.) or other techniques, including mass spectroscopy assays, 2D gel electrophoresis assays, etc. Thus, the proteins corresponding to the CoAA genes, i.e. those identified as being important in a cancer phenotype, can be evaluated in a cancer diagnostic test.

In some embodiments, antibodies to the CoAM can be used in in situ imaging techniques. In this method cells are contacted with from one to many antibodies to CoAM. Following washing to remove non-specific antibody binding, the presence of the antibody or antibodies is detected. In one embodiment the antibody is detected by incubating with a secondary antibody that contains a detectable label. In another method the primary antibody to the CoAM contains a detectable label. In another preferred embodiment each one of multiple primary antibodies contains a distinct and detectable label. This method finds particular use in simultaneous screening for a plurality of cancer markers. As will be appreciated by one of ordinary skill in the art, numerous other histological imaging techniques can be used.

In some embodiments the label is detected in a fluorometer which has the ability to detect and distinguish emissions of different wavelengths. In addition, a fluorescence activated cell sorter (FACS) can be used in the method.

In some embodiments, in situ hybridization of labeled CoAA or CoAM nucleic acid probes to tissue arrays is done. For example, arrays of tissue samples, including cancer tissue and/or normal (cancer-free tissue), are made. In situ hybridization as is known in the art can then be done. Cells having one or more gene amplifications in CoAA are indicative of cancer.

It is understood that when comparing the expression fingerprints between an individual and a standard, the skilled artisan can make a diagnosis as well as a prognosis. It is further understood that the genes which indicate the diagnosis may differ from those which indicate the prognosis. The data from the disclosed assays can be used to assist in the diagnosis of cancer.

In a preferred embodiment, the CoAA or CoAM proteins, antibodies, nucleic acids, and cells containing amplicons in CoAA are used in prognosis assays. In some embodiments, gene expression profiles can be generated that correlate to cancer severity, in terms of long term prognosis. Again, this may be done on either a protein or gene level, with the use of genes being preferred. In some embodiments, CoAA or CoAM probes are attached to solid supports for the detection and quantification of CoAA sequences in a tissue or patient. The assays proceed as outlined for diagnosis.

The efficacy of therapeutic agents, such as antibodies and/or other candidate drugs also can be determined using the diagnostic assays described above. As will be appreciated by a person of skill in the art, assays to determine the efficacy of a therapeutic agent require the establishment of baseline values. In some embodiments, this is accomplished by combining body fluids, tissue biopsies, or cell extracts taken from a patient with cancer prior to treatment with the candidate drug with one or more antibody(ies) to a CoAM under conditions suitable for complex formation. Such conditions are well known in the art. The amount of standard complex formation may be quantified by comparing levels of antibody-target complex in the normal sample with a dilution series of positive controls, in which a known amount of antibody is combined with known concentrations of purified CoAM. Standard values obtained from a patient before treatment may be compared with values obtained from a patient after treatment. Deviation between standard and subject values establishes the efficacy of the drug.

III. Screening Assays

In some embodiments, the CoAA or splice variants thereof, such as CoAM, proteins, antibodies, nucleic acids, and cells containing the CoAA or splice variant proteins or nucleic acids are used in screening assays. For example, screens for agents that modulate the cancer phenotype can be run. This can be done by screening for modulators of gene expression or for modulators of protein activity at the individual gene or protein level or by evaluating the effect of drug candidates on a "gene expression profile". In some embodiments, the expression profiles are used in conjunction with high throughput screening techniques to allow monitoring for expression profile genes after treatment with a candidate agent (see Zlokarnik, et al., *Science,* 279:84-8 (1998)).

"Modulation" includes both an increase and a decrease in gene expression or activity. The preferred amount of modulation will depend on the original change of the gene expression in normal versus tumor tissue, with changes of at least 10%, preferably 50%, more preferably 100-300%, and in some embodiments 300-1000% or greater. If a gene exhibits a 4 fold increase in tumor compared to normal tissue, a decrease of about four fold is desired; a 10 fold decrease in tumor compared to normal tissue gives a 10 fold increase in expression for a candidate agent is desired, etc.

As will be appreciated by those in the art, this may be done by evaluation at either the gene or the protein level; that is, the amount of gene expression may be monitored using nucleic acid probes and the quantification of gene expression levels, or, alternatively, the level of the gene product itself can be monitored, for example through the use of antibodies to the CoAA or CoAM and standard immunoassays. Alternatively, binding and bioactivity assays with the protein may be done as outlined below.

In some embodiments, gene expression monitoring is done and a number of genes in addition to CoAA, i.e. an expression profile, are monitored simultaneously. If desired, multiple protein expression monitoring can be done as well. In embodiments monitoring multiple genes or proteins, the corresponding CoAA or splice variant probes are immobilized to solid supports. It is understood that immobilization can occur by any means, including for example; by covalent attachment, by electrostatic immobilization, by attachment through a ligand/ligand interaction, by contact or by depositing on the surface. "Solid support" or "solid substrate" refers to any solid phase material upon which a CoAA sequence, or antibody is synthesized, attached, ligated or otherwise immobilized. A solid support may be composed of organic polymers such as polystyrene, polyethylene, polypropylene, polyfluoroethylene, polyethyleneoxy, and polyacrylamide, as well as co-polymers and grafts thereof. A solid support may also be inorganic, such as glass, silica, controlled-pore-glass (CPG), or reverse-phase silica. The configuration of a solid support may be in the form of beads, spheres, particles, granules, a gel, or a surface. Surfaces may be planar, substantially planar, or non-planar. Solid supports may be porous or non-porous, and may have swelling or non-swelling characteristics. A solid support may be configured in the form of a well, depression or other container, vessel, feature or location. A plurality of solid supports may be configured in an array at various locations, addressable for robotic delivery of reagents, or by detection means including scanning by laser illumination and confocal or deflective light gathering.

Generally, a candidate bioactive agent is added prior to analysis. The term "candidate bioactive agent" or "drug candidate" or grammatical equivalents as used herein describes any molecule, e.g., protein, oligopeptide, small organic or inorganic molecule, polysaccharide, polynucleotide, etc., to be tested for bioactive agents that are capable of directly or indirectly altering either the cancer phenotype, binding to and/or modulating the bioactivity of an CoAA or splice variant thereof, or the expression of a CoAA or splice variant sequence. In a particularly preferred embodiment, the candidate agent suppresses the cancer phenotype, for example to a normal tissue fingerprint. Generally a plurality of assay mixtures are run in parallel with different agent concentrations to obtain a differential response to the various concentrations. Typically, one of these concentrations serves as a negative control, i.e., at zero concentration or below the level of detection. In a preferred embodiment, the expression of CoAM is inhibited.

In one aspect, a candidate agent will neutralize the effect of CoAA or a splice variant thereof such as CoAM. By "neutralize" is meant that activity of a protein is either inhibited or counter acted against so as to have substantially no effect on a cell.

Candidate agents encompass numerous chemical classes, though typically they are organic or inorganic molecules, preferably small organic compounds having a molecular weight of more than 100 and less than about 2,500 daltons. Preferred small molecules are less than 2000, or less than 1500 or less than 1000 or less than 500 D. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, proteins, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In assays for altering the expression profile of one or more CoAA or splice variant sequences, after the candidate agent has been added and the cells allowed to incubate for some period of time, the sample containing the CoAA or splice variant sequences to be analyzed is added to a solid support. If required, the CoAA or splice variant sequence is prepared using known techniques. For example, the sample may be treated to lyse the cells, using known lysis buffers, electroporation, etc., with purification and/or amplification such as PCR occurring as needed, as will be appreciated by those in the art.

Generally, one of the assay components is labeled to provide a means of detecting the binding complex of interest. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the CoAA or CoAM nucleic acids, proteins and antibodies at any position. For example, the label should be capable of producing, either directly or indirectly, a detectable signal. The detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the label may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982)). The label also can be an enzyme, such as, alkaline phosphatase or horseradish peroxidase, which when provided with an appropriate substrate produces a product that can be detected. Alternatively, the label can be a labeled compound or small molecule, such as an enzyme inhibitor, that binds but is not catalyzed or altered by the enzyme. The label also can be a moiety or compound, such as, an epitope tag or biotin which specifically binds to streptavidin. For the example of biotin, the streptavidin is labeled as described above, thereby, providing a detectable signal for the bound target sequence. As known in the art, unbound labeled streptavidin is removed prior to analysis.

As will be appreciated by those in the art, these assays can be direct hybridization assays or can comprise "sandwich assays", which include the use of multiple probes, as is generally outlined in U.S. Pat. Nos. 5,681,702, 5,597,909, 5,545,730, 5,594,117, 5,591,584, 5,571,670, 5,580,731, 5,571,670, 5,591,584, 5,624,802, 5,635,352, 5,594,118, 5,359,100, 5,124,246 and 5,681,697, all of which are hereby incorporated by reference.

A variety of hybridization conditions may be used in the present invention, including high, moderate and low stringency conditions as outlined above. The assays are generally run under stringency conditions which allows formation of the label probe hybridization complex only in the presence of target. Stringency can be controlled by altering a step parameter that is a thermodynamic variable, including, but not limited to, temperature, formamide concentration, salt concentration, chaotropic salt concentration pH, organic solvent concentration, etc.

These parameters may also be used to control non-specific binding, as is generally outlined in U.S. Pat. No. 5,681,697. Thus it may be desirable to perform certain steps at higher stringency conditions to reduce non-specific binding.

The reactions outlined herein may be accomplished in a variety of ways, as will be appreciated by those in the art. Components of the reaction may be added simultaneously, or sequentially, in any order, with preferred embodiments outlined below. In addition, the reaction may include a variety of other reagents may be included in the assays. These include reagents like salts, buffers, neutral proteins, e.g. albumin, detergents, etc which may be used to facilitate optimal hybridization and detection, and/or reduce non-specific or background interactions. Also reagents that otherwise improve the efficiency of the assay, such as protease inhibitors, nuclease inhibitors, anti-microbial agents, etc., may be used, depending on the sample preparation methods and purity of the target. In addition, either solid phase or solution based (i.e., kinetic PCR) assays may be used.

Once the assay is run, the data is analyzed to determine the expression levels, and changes in expression levels as between states, of individual genes, or individual proteins, forming an expression profile.

In some embodiments, screening is done to alter the biological function of the expression product of the CoAA gene. Again, having identified the importance of a gene in a particular state, screening for agents that bind and/or modulate the biological activity of the gene product can be run as is more fully outlined below.

In some embodiments, screens are designed to first find candidate agents that can bind to CoAA or splice variant proteins, and then these agents may be used in assays that evaluate the ability of the candidate agent to modulate the CoAA or splice variant activity and the cancer phenotype. As will be appreciated by those in the art, there are a number of different assays which may be run; binding assays and activity assays.

In some embodiments, binding assays are done. In general, purified or isolated CoAA or splice variant proteins or nucleic acids are used. The methods comprise combining a CoAA or splice variant protein or nucleic acids and a candidate bioactive agent, and determining the binding of the candidate agent to the CoAA or splice variant protein or nucleic acids. Generally, the CoAA or splice variant protein or nucleic acids or the candidate agent is non-diffusably bound to a solid support having isolated sample receiving areas (e.g. a microtiter plate, an array, etc.). Microtiter plates and arrays are especially convenient because a large number of assays can be carried out simultaneously, using small amounts of reagents and samples. The particular manner of binding of the composition is not crucial so long as it is compatible with the reagents, maintains the activity of the composition and is nondiffusable. Preferred methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the protein or agent, excess unbound material is removed by washing. The sample receiving areas may then be blocked through incubation with bovine serum albumin (BSA), casein or other innocuous protein or other moiety.

In some embodiments, the CoAA or splice variant protein or nucleic acids are bound to the support, and a candidate bioactive agent is added to the assay. Alternatively, the candidate agent is bound to the support and the CoAA or splice variant protein or nucleic acids are added. Novel binding agents include specific antibodies, non-natural binding agents identified in screens of chemical libraries, peptide analogs, etc. Of particular interest are screening assays for agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate bioactive agent to the CoAA or splice variant protein or nucleic acids may be done in a number of ways. In a preferred embodiment, the candidate bioactive agent is labeled, and binding determined directly. For example, this may be done by attaching all or a portion of the CoAA or splice variant protein or nucleic acids to a solid support, adding a labeled candidate agent (for example a fluorescent label), washing off excess reagent, and determining whether the label is present on the solid support. Various blocking and washing steps may be utilized as is known in the art.

In some embodiments, only one of the components is labeled. For example, the proteins (or proteinaceous candidate agents) may be labeled at tyrosine positions using $^{125}$I, or with fluorophores. Alternatively, more than one component may be labeled with different labels; using $^{125}$I for the proteins, for example, and a fluorophor for the candidate agents.

In some embodiments, the binding of the candidate bioactive agent is determined through the use of competitive binding assays. In this embodiment, the competitor is a binding moiety known to bind to the CoAA or splice variant protein or nucleic acid, such as an antibody, peptide, binding partner, ligand, etc. Under certain circumstances, there may be competitive binding as between the bioactive agent and the binding moiety, with the binding moiety displacing the bioactive agent.

In some embodiments, the candidate bioactive agent is labeled. Either the candidate bioactive agent, or the competitor, or both, is added first to the protein for a time sufficient to allow binding, if present. Incubations may be performed at any temperature which facilitates optimal activity, typically between 4 and 40° C. Incubation periods are selected for optimum activity, but may also be optimized to facilitate rapid high through put screening. Typically between 0.1 and 1 hour will be sufficient. Excess reagent is generally removed or washed away. The second component is then added, and the presence or absence of the labeled component is followed, to indicate binding.

In some embodiments, the competitor is added first, followed by the candidate bioactive agent. Displacement of the competitor is an indication that the candidate bioactive agent is binding to the CoAA or splice variant protein or nucleic acid and thus is capable of binding to, and potentially modulating, the activity of CoAA or splice variant protein or nucleic acid. In this embodiment, either component can be labeled. Thus, for example, if the competitor is labeled, the presence of label in the wash solution indicates displacement by the agent. Alternatively, if the candidate bioactive agent is labeled, the presence of the label on the support indicates displacement.

In other embodiments, the candidate bioactive agent is added first, with incubation and washing, followed by the competitor. The absence of binding by the competitor may indicate that the bioactive agent is bound to the CoAA or splice variant protein or nucleic acid with a higher affinity. Thus, if the candidate bioactive agent is labeled, the presence of the label on the support, coupled with a lack of competitor binding, may indicate that the candidate agent is capable of binding to the CoAA or splice variant protein or nucleic acid.

In some embodiments, the methods include differential screening to identify bioactive agents that are capable of modulating the activity of the CoAA or splice variant protein or nucleic acid. In this embodiment, the methods comprise combining a CoAA or splice variant protein or nucleic acid and a competitor in a first sample. A second sample comprises a candidate bioactive agent, a CoAA or splice variant protein or nucleic acid and a competitor. The binding of the competitor is determined for both samples, and a change, or difference in binding between the two samples indicates the presence of an agent capable of binding to the CoAA or splice variant protein or nucleic acid and potentially modulating its activity. That is, if the binding of the competitor is different in the second sample relative to the first sample, the agent is capable of binding to the CoAA or splice variant protein or nucleic acid.

In some embodiments, methods for screening for bioactive agents capable of modulating the activity of a CoAA or splice variant protein or nucleic acid in a cell are provided. The methods include adding a candidate bioactive agent, as defined above, to a cell having CoAA or splice variant protein or nucleic acid. Typically, cells having one or more amplicons of CoAA are used. Methods for culturing cells and for assaying cell scattering, adhesion and migration are described in Russell et al., *J. Cell Sci.*, 116:3543-3556 (2003), the entire contents of which are incorporated herein by reference.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

In one aspect, the assays are evaluated in the presence or absence or previous or subsequent exposure of physiological signals, for example hormones, antibodies, peptides, antigens, cytokines, growth factors, action potentials, pharmacological agents including chemotherapeutics, radiation, carcinogenics, or other cells (i.e. cell-cell contacts). In another example, the determinations are determined at different stages of the cell cycle process.

IV. Pharmaceutical Compositions and Methods of Treatment

A. Pharmaceutical Compositions

Another embodiment provides pharmaceutical compositions containing one or more of the disclosed compositions. By "pharmacological activity" herein is meant that the compounds are able to inhibit or interfere with the activity of CoAA or a splice variant thereof. The compounds having the desired pharmacological activity may be administered in a physiologically acceptable carrier to a subject or patient. A "subject" or "patient" includes both humans and other animals, particularly mammals, and domestic animals. Thus, the methods are applicable to both human therapy and veterinary applications.

In some embodiments, bioactive agents include antibodies that recognize a splice variant such as CoAM and that have been demonstrated to inhibit or modulate CoAM activity or bioavailability. In other embodiments, bioactive agents include antisense compositions. These agents can be delivered directly or in pharmaceutical compositions along with suitable carriers or excipients, as well known in the art. Present methods of treatment include embodiments providing for administration of an effective amount of a compound or agent that inhibits the activity or expression of CoAA or a splice variant thereof to a patient in need of treatment.

An effective amount of such agents can readily be determined by routine experimentation, as can the most effective and convenient route of administration and the most appropriate formulation. Various formulations and drug delivery systems are available in the art.

Suitable routes of administration may, for example, include oral, rectal, transmucosal, transdermal, nasal, or intestinal administration and parenteral delivery, including intramuscular, subcutaneous, intramedullary injections, as well as intrathecal, direct intraventricular, intravenous, intraperitoneal, intranasal, or intraocular injections. The agent or composition thereof may be administered in a local rather than a systemic manner. For example, a suitable agent can be delivered via injection or in a targeted drug delivery system, such as a depot or sustained release formulation.

The pharmaceutical compositions may be manufactured by any of the methods well-known in the art, such as by conventional mixing, dissolving, granulating, dragee-making, levigating, emulsifying, encapsulating, entrapping, or lyophilizing processes. The compositions can include one or more physiologically acceptable carriers such as excipients and auxiliaries that facilitate processing of active molecules into preparations for pharmaceutical use. Proper formulation is dependent upon the route of administration chosen.

For example, for injection, the composition may be formulated in aqueous solutions, preferably in physiologically compatible buffers such as Hanks's solution, Ringer's solution, or physiological saline buffer. For transmucosal or nasal administration, penetrants appropriate to the barrier to be permeated are used in the formulation. Such penetrants are generally known in the art. For oral administration, the agents can be formulated readily by combining the active agents with pharmaceutically acceptable carriers well known in the art. Such carriers enable the agents of the invention to be formulated as tablets, pills, dragees, capsules, liquids, gels, syrups, slurries, suspensions and the like, for oral ingestion by a subject. The agents may also be formulated in rectal compositions such as suppositories or retention enemas, e.g., containing conventional suppository bases such as cocoa butter or other glycerides.

Pharmaceutical preparations for oral use can be obtained as solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agent doses.

Pharmaceutical preparations for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration.

For administration by inhalation, the agents can be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide, or any other suitable gas. In the case of a pressurized aerosol, the appropriate dosage unit may be determined by providing a valve to deliver a metered amount. Capsules and cartridges for use in an inhaler or insufflator may be formulated. These typically contain a powder mix of the agent and a suitable powder base such as lactose or starch.

Compositions formulated for parenteral administration by injection, e.g., by bolus injection or continuous infusion can be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Formulations for parenteral administration include aqueous solutions of the compound or agent to be administered, including in water-soluble form.

Suspensions of the active agents may also be prepared as appropriate oily injection suspensions. Suitable lipophilic solvents or vehicles include fatty oils such as sesame oil and synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the agents to allow for the preparation of highly concentrated solutions. Alternatively, the active ingredient may be in powder form for constitution with a suitable vehicle, e.g., sterile pyrogen-free water, before use.

As mentioned above, the compositions can also be formulated as a depot preparation. Such long acting formulations may be administered by implantation (for example, subcutaneously or intramuscularly) or by intramuscular injection. Thus, for example, the present agents may be formulated with suitable polymeric or hydrophobic materials (for example as an emulsion in an acceptable oil) or ion exchange resins, or as sparingly soluble derivatives, for example, as a sparingly soluble salt.

Suitable carriers for the hydrophobic molecules of the invention are well-known in the art and include co-solvent systems comprising, for example, benzyl alcohol, a nonpolar surfactant, a water-miscible organic polymer, and an aqueous phase. The co-solvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system is effective in dissolving hydrophobic agents and produces low toxicity upon systemic administration. Naturally, the proportions of a co-solvent system may be varied considerably without destroying its solubility and toxicity characteristics. Furthermore, the identity of the co-solvent components may be varied. For example, other low-toxicity nonpolar surfactants may be used instead of polysorbate 80, the fraction size of polyethylene glycol may be varied, other biocompatible polymers may replace polyethylene glycol, e.g. polyvinyl pyrrolidone, and other sugars or polysaccharides may substitute for dextrose.

Alternatively, other delivery systems for hydrophobic molecules may be employed. Liposomes and emulsions are well known examples of delivery vehicles or carriers for hydrophobic drugs. Liposomal delivery systems are discussed above in the context of gene-delivery systems. Certain organic solvents such as dimethylsulfoxide also may be employed, although usually at the cost of greater toxicity. Additionally, the agents may be delivered using sustained-release systems, such as semi-permeable matrices of solid hydrophobic polymers containing the effective amount of the composition to be administered. Various sustained-release materials are established and available to those of skill in the art. Sustained-release capsules may, depending on their chemical nature, release the agents for a few weeks up to over 100 days. Depending on the chemical nature and the biological stability of the therapeutic reagent, additional strategies for protein stabilization may be employed.

For any composition employed herein, a therapeutically effective dose can be estimated initially using a variety of techniques well-known in the art. For example, in a cell culture assay, a dose can be formulated in animal models to achieve a circulating concentration range that includes the $IC_{50}$ as determined in cell culture. Where inhibition of CoAA or a splice variant's activity is desired, the concentration of the test agent that achieves a half-maximal inhibition of CoAA or splice variant activity can be determined. Dosage ranges appropriate for human subjects can be determined, using data obtained from cell culture assays and other animal studies.

A therapeutically effective dose of an agent refers to that amount of the agent that results in amelioration of symptoms or a prolongation of survival in a subject. Toxicity and therapeutic efficacy of such molecules can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio of toxic to therapeutic effects is the therapeutic index, which can be expressed as the ratio $LD_{50}/ED_{50}$. Agents that exhibit high therapeutic indices are preferred.

Dosages preferably fall within a range of circulating concentrations that includes the $ED_{50}$ with little or no toxicity. Dosages may vary within this range depending upon the dosage form employed and the route of administration utilized. The exact formulation, route of administration, and dosage should be chosen, according to methods known in the art, in view of the specifics of a subject's condition.

Dosage amount and interval may be adjusted individually to provide plasma levels or tissue levels of the active moiety which are sufficient to affect the expression or activity of CoAA or a splice variant, as desired, i.e. minimal effective concentration (MEC). The MEC will vary for each agent but can be estimated from, for example, in vitro data, such as the concentration necessary to achieve 50-90% inhibition of CoAA or splice variant activity using the assays described herein. Dosages necessary to achieve the MEC will depend on individual characteristics and route of administration. Agents or compositions thereof should be administered using a regimen which maintains plasma levels above the MEC for about 10-90% of the duration of treatment, preferably about 30-90% of the duration of treatment, and most preferably between 50-90%. In cases of local administration or selective uptake, the effective local concentration of the drug may not be related to plasma concentration.

The amount of agent or composition administered will, of course, be dependent on a variety of factors, including the sex, age, and weight of the subject being treated, the severity of the affliction, the manner of administration, and the judgment of the prescribing physician.

The present compositions may, if desired, be presented in a pack or dispenser device containing one or more unit dosage forms containing the active ingredient. Such a pack or device may, for example, comprise metal or plastic foil, such as a blister pack. The pack or dispenser device may be accompanied by instructions for administration. Compositions comprising a agent of the invention formulated in a compatible pharmaceutical carrier may also be prepared, placed in an appropriate container, and labeled for treatment of an indicated condition. Suitable conditions indicated on the label may include treatment of disorders or diseases, such as squamous cell carcinoma or other cancers and conditions associated with altered expression of CoAA.

B. Methods of Treatment

One embodiment provides a method for treating one or more symptoms of cancer by administering an effective amount of an inhibitory nucleic acid specific for a nucleic acid encoding CoAA or a splice variant thereof including, but not limited to CoAM to alleviate one or more symptoms associated with a cancer. The inhibitory nucleic acid can be a PNA, siRNA, antisense DNA, microRNA or a combination thereof. Symptoms associated with cancer include tumor size and cellular proliferation. Representative cancers that can be treated include, but are not limited to lung, pancreas, melanoma, esophageal, lymphoma, squamous skin cell, stomach, ovary, and breast cancer. The inhibitory nucleic acid can be one or more of the compositions disclosed above.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

Methods and Materials

Immunohistochemistry

Polyclonal anti-CoAA antibody (CoAA-specific, against 307-545 aa) and anti-RRM antibody (against 1-156 aa of CoAM) were prepared in rabbits by immunization with GST fusion proteins (Covance). His-tagged CoAA protein as antigen was cross-linked to the Affi-gel 10 resin according to the manufacturer's protocol (Bio-Rad), and was used for affinity purification of anti-CoAA (21). Sagittal sections of mouse embryonic tissue at E12.5 and E15.5 were stained with affinity purified anti-CoAA at a dilution of 1:250. The P19 embryoid bodies were paraffin-embedded and the sections were stained with anti-CoAA, anti-RRM antibodies at dilution of 1:500, and with anti-active caspase-3 peptide antibody at 1:200 (USBiological, C2087-16A). Antibody binding was detected using biotinylated anti-rabbit or anti-mouse IgG F(ab)$_2$ secondary antibody followed by detecting reagents (DAKO). Sections were counterstained with hematoxylin.

Immunoblotting

Endogenous CoAA and CoAM in P19 cells were detected using whole cell extracts at each differentiating stage and probed with anti-RRM antibody. For antibody evaluation, CoAA and CoAM were overexpressed in CV1 cells under the control of a CMV promoter in pcDNA3 vector (Invitrogen). Immunoblots were probed with anti-CoAA and anti-RRM primary antibodies at a dilution of 1:200 and detected with the ECL system (Amersham Pharmacia).

Polyclonal anti-CoAA was prepared in rabbits by immunization with a glutathione S-transferase (GST)-CoAA (307-545) fusion protein (Covance). Affinity resin Affi-gel 10 (Bio-Rad) was covalently cross-linked to His-tagged CoAA (without GST) as antigen. This resin was then used to affinity purify anti-CoAA according to the manufacturer's protocol (Bio-Rad). Human tumor sections were deparaffinized, treated with xylene and ethanol, and stained with affinity-purified antibody at a dilution of 1:200. Antibody binding was detected using biotinylated anti-rabbit IgG F(ab)$_2$ antibody followed by detecting reagents (DAKO). Sections were counterstained with hematoxylin. Immunoblots were probed with primary antibodies at a dilution of 1:200 and detected with the ECL system (Amersham Pharmacia). For immunofluorescence, NIH3T3 cells were methanol-fixed and stained with mouse monoclonal anti-Flag antibody at 1:500 (Sigma, M2). Anti-mouse Cy3-conjugated secondary antibody (Jackson Immuno-Research Lab) was applied at a dilution of 1:200.

P19 Cell and ES Cell Culture and Differentiation

Mouse embryonal carcinoma P19 cells were maintained in α-modified minimum essential medium supplemented with 7.5% bovine calf serum and 2.5% fetal bovine serum, 100 U/ml penicillin and 0.1 µg/µl streptomycin. Cells were incubated in 5% $CO_2$ at 37° C. Undifferentiated murine embryonal carcinoma P19 cells (EC) were induced by 500 nM all-trans retinoic acid (RA) (Sigma) up to 4 days in suspension culture to form embryoid bodies (EB2-4). The EBs were trypsinized and plated in tissue culture dish. The cells were further differentiated (D3-12) for an additional 12 days in the absence of RA. P19 cells were transfected with the plasmid or siRNA of CoAA (25 nM) (21), when applicable, using Lipofectamine 2000 reagent (Invitrogen) for 24 hours before harvest. Total amounts of DNA for each well were balanced by adding vector DNA. Mouse embryonic stem (ES) cells (D3, 12952/SvPas blastocysts, ATCC) were maintained on gamma-irradiated (30 Gy) mouse embryonic fibroblast feeder layers. The culture and differentiating conditions were as previously described (22). Briefly, neuronal differentiation of ES cell-derived EBs was induced by 1000 nM RA for 6 days to form EBs (EB2-EB6). Undisrupted EBs were differentiated in culture in the absence of RA for an additional 15 days (D3-D15) before harvest.

Luciferase Assay

CV-1 cells were maintained in Dulbecco's modified Eagle's medium, supplemented with 10% fetal bovine serum and 100 U/ml penicillin and 0.1 µg/µl streptomycin, and were incubated in 5% $CO_2$ at 37° C. CV-1 or P19 cells were transfected in triplicate in 24-well plates using Lipofectamine 2000 (Invitrogen). Cells were incubated with ligand dexamethasone (100 nM) to induce MMTV-luciferase reporter, when applicable, for 16 hours before harvest. Total amounts of DNA for each well were balanced by adding vector DNA. Relative luciferase activities were measured by a Dynex luminometer. Data are shown as means of triplicate transfections±standard errors.

RT-PCR and Real-Time Quantitative PCR

Normalized first-strand cDNAs from multiple normal human tissues and cancer cell lines (MTC™ panels, Clontech) were analyzed by PCR using primer pairs common to all CoAA splicing forms. For P19 cells, total RNA was isolated at each differentiation stage using Trizol reagent (Invitrogen), treated with DNase I, and normalized for their concentrations before use. RT-PCR was performed using the one-step RT-PCR kit (Qiagen). In transfection experiments, P19 cells were cotransfected with CoAA minigenes and p54$^{nrb}$ or PSF expression plasmids. Primer pairs used in RT-PCR are as follows: (from 5' to 3') primers common to endogenous CoAA, CoAM, and CoAR splicing forms, atgaagatattcgtgggcaa (SEQ ID NO:6), ctaaacgccggtcggaacc (SEQ ID NO:7); CoAM-specific, tctccaccaagggtatggtt (SEQ ID NO:8), ctacatgcgcgctggta (SEQ ID NO:9); Nanog, agggtctgctactgagatgctctg (SEQ ID NO:10), caaccactg-gttttctgccaccg (SEQ ID NO:11); Oct4, ctgagggccaggcag-gagcacgag (SEQ ID NO:12), ctgtagggagggcttcgggcactt (SEQ ID NO:13); Sox6, cagcggatggagaggaagcaatg (SEQ ID NO:14), cttttctgttcatcatgggctgc (SEQ ID NO:15); MAP2, ggacatcagcctcactcacaga (SEQ ID NO:16), gcagcatgt-tcaaagtcttcacc (SEQ ID NO:17); GFAP, gaatgactcctccactc-cctgc (SEQ ID NO:18), cgctgtgaggtctggcttggc (SEQ ID NO:19); and GAPDH, accacagtccatgccatcac (SEQ ID NO:20), tccaccaccctgttgctgta (SEQ ID NO:21). Primer pairs for detecting transcripts from the CoAA minigene are as follows: F, aatgtgtcggctgcatgc (SEQ ID NO:22); B, ctaaacgccggtcggaacc (SEQ ID NO:23); C, tatgaagagatacgc-cctggttcc (SEQ ID NO:24); V, atggctggcaactagaaggcac (SEQ ID NO:25); J, tctccaccaagggtatggtt (SEQ ID NO:26); and A, gcctggctggccgcggtag (SEQ ID NO:27). Real-time quantitative RT-PCR primers: CoAA, cttcgactaccagcaggctttt (SEQ ID NO:28), ccgtcagaggcgccacataag (SEQ ID NO:29); and CoAM, caaagaagtgaagggcaagc (SEQ ID NO:30), aatc-cagcgaggactttgtc (SEQ ID NO:31). Quantitative RT-PCR was performed on iCycler (BioRad) using SYBR Green I (Invitrogen).

Sequence Analyses and CoAR Accession

Alu repeats within the regulatory sequences of the CoAA gene were identified using Censor Server at Genetic Information Research Institute and the BLAST search at the National Center for Biotechnology Information (NCBI). Transcription factor binding sites within the CoAA basal promoter were predicted by the TFSEARCH program at the Computational Biology Research Center of Japan. Human CoAR sequences have been deposited at GenBank/EBI Data Bank with accession number DQ294957.

EXAMPLES

Example 1

Alternative Splicing of CoAA Gene Transcripts

The human CoAA gene (gene symbol RBM14) contains three exons spanning approximately 11 Kb. The CoAA gene is alternatively spliced and produces CoAA and CoAM transcripts through competitive 5' alternative splicing events between the second and third exons (FIG. 1A) (Iwasaki, T. et al., J Biol Chem, 276:33375-33383 (2001); Sui, Y. et al., Oncogene, 26:822-835 (2007)). The resulting CoAA and CoAM proteins share two N-terminal RRM domains, but only CoAA possesses the C-terminal activation domain containing repeated YxxQ motifs (id.). Consequently, CoAA is a potent transcriptional coactivator, whereas CoAM competes with CoAA via shared RRM domains and represses CoAA activities in both transcription and splicing (Iwasaki, T. et al., J Biol Chem, 276:33375-33383 (2001); Auboeuf, D. et al., Science, 298:416-419 (2002). Using RT-PCR analysis a third splice variant of CoAA, designated here as CoAR (coactivator regulator), was identified in multiple human adult and embryonic tissues, and in cancer cell lines. Sequencing analysis indicated that the CoAR transcript was derived by joining the first and third exons, skipping the entire second exon, and altering the reading frame for the third exon. CoAR contains only one RRM domain encoded by the first exon. The transcriptional activity of CoAR is moderately repressive when expressed in a transient transfection assay (FIG. 1B). This splice variant was previously undetected due to its low abundance in HeLa cells, in which CoAA and CoAM were originally cloned. The nucleotide and amino-acid sequences of CoAR have been deposited at the NCBI with accession number DQ294957.

The CoAA mRNA transcript is expressed in all tissues and cells examined as determined by RT-PCR, a result consistent with previous Northern blot analysis (Iwasaki, T. et al., J Biol Chem, 276:33375-33383 (2001)). Sequence analyses confirmed that the observed three PCR products are the three CoAA splice variants. The CoAA transcript is relatively abundant in both normal tissues and cancer cell lines (data not shown). However, the relative levels of CoAA, CoAM, and CoAR mRNAs vary between samples. In some human fetal tissues and cancer cell lines, CoAM or CoAR expression is below the limits of detection. The variation in the expression ratios of CoAA isoforms, which could partially due to the alternative splicing regulations, represents a possible cell-specific control of CoAA activity through its inhibitory splice variants.

Example 2

Switched Alternative Splicing of CoAA and CoAM During P19 Stem Cell Differentiation CoAA alternative splicing was investigated in a physiological context using a murine embryonal carcinoma (EC)

stem cell line, P19, during neuronal differentiation. P19 is a teratocarcinoma-derived pluripotent stem cell line that can give rise to all three germ layers in mice (van der Heyden, M. A. and Defize, L. H., *Cardiovasc Res*, 58:292-302 (2003)). Undifferentiated P19 EC cells in culture can be induced by retinoic acid (RA) to differentiate to neuronal and glial cells (Chen, X., et al., *Cell Biol Int*, 28:791-799 (2004); Jones-Villeneuve, E. M., et al., *J Cell Biol*, 94:253-262 (1982)) or by DMSO to cardiac and skeletal muscles (Gianakopoulos, P. J. and Skerjanc, I. S., *J Biol Chem*, 280:21022-21028 (2005). Treatment of P19 EC cells with RA for up to 4 days induces non-adhering aggregates called embryoid bodies (EBs) which resemble the inner cell mass of embryos (Coucouvanis, E. and Martin, G. R., *Development*, 126:535-546 (1999); Schratt, G., et al., *Embo J*, 23:1834-1844 (2004)). Prolonged culture in the absence of RA for an additional 12 days induces neuronal differentiation into a mixture of cell types including differentiated neurons and glial cells, as well as a variety of partially differentiated or undifferentiated cells (van der Heyden, M. A. and Defize, L. H., *Cardiovasc Res*, 58:292-302 (2003)).

Figure 2:
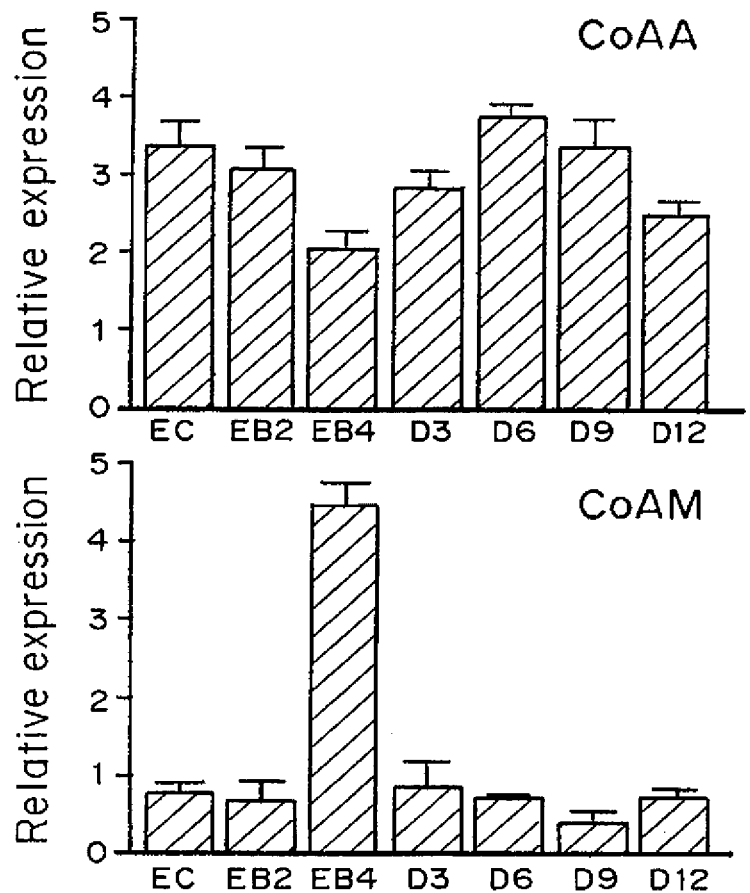
FIG. 2 is a bar graph of relative expression CoAA and CoAM determined by quantitative real-time PCR during stem cell differentiation.

The expression of endogenous CoAA and its splicing variant transcripts was analyzed using RNA isolated at different time points during P19 cell differentiation. Expression of CoAA shows a rapid but transient decrease, reaching the minimum at day 4 corresponding to the EB formation (FIG. 2A). In contrast, the expression of CoAM is drastically increased during EB formation, reaching the maximum level at day 4 and declining rapidly during further differentiation. These data indicate that an alternative splicing switch between CoAA and CoAM occurs during EB formation. The expression of CoAR is very low and without significant change at the EB stag). Subsequent analysis focused on CoAA and CoAM. The switched expression was confirmed using primer pairs common to both CoAA and CoAM, and was quantitatively measured by real-time PCR analysis (FIG. 2). A number of differentiation markers were analyzed simultaneously as controls. The expression of Nanog followed by Oct4, and then by CoAA declines upon RA treatment. Meanwhile, the expression levels of Sox6, a member of the Sox (SRY box) gene family, MAP2 (microtubule-associated protein-2), a neuronal marker, and GFAP (glial fibrillary acidic protein), a glial cell marker, increase sequentially during neuronal differentiation. These data together suggest that a switched expression of CoAA transcripts occurs during the EB stages of P19 cell differentiation.

Mouse embryonic stem (ES) cells were examined and the switch from CoAA to CoAM expression was also found in ES cells during EB formation. Since the EB of ES cells was undisrupted in continued culture condition, the down-regulation of CoAM was delayed, correlating to the presence of EB. In addition to RA-induced neuronal differentiation, the switched expression of CoAA and CoAM was also detected during DMSO-induced muscle differentiation of P19 cells (not shown). These results indicate that the increase of CoAM, which inhibits CoAA transcriptional activity, might be common in different type of stem cell differentiation at the EB stage.

To detect the expression of CoAA and CoAM at the protein level, two CoAA polyclonal antibodies were used. One was raised against the two N-terminal RRM domains (anti-RRM) for detecting both CoAA and CoAM, and the other was raised against the CoAA-specific C-terminal activation domain (anti-CoAA). A CoAM-specific antibody is not feasible due to its overlapping primary sequence with CoAA. The two antibodies detected both endogenous and overexpressed CoAA in 293 cells. The endogenous CoAM protein level is very low in this cell line, which is consistent with its mRNA level.

Since CoAM mRNA is significantly elevated in EBs of P19 cells, the staining pattern of the two antibodies were compared to infer the expression pattern of CoAM. Embryoid bodies are large multi-cell aggregates that form cavities at day 4 of RA induction. CoAA expression, assessed by anti-CoAA, was detected in almost all cells of early-stage EBs, but only in the outer layer of mature EBs. CoAA was not detected in the EB cavity. In contrast, the high-level of expression of CoAM, detected by anti-RRM with the comparison of anti-CoAA, was found predominantly within the EB cavity. The majority of signals within the cavity are unlikely contributed by CoAR when the mRNA level is considered, especially, when further confirmed by Western blot analysis. Most of CoAM protein appears to be in cytoplasm although a low level of nuclear CoAM may also be present. This pattern was also confirmed by overexpression of a Flag-tagged CoAM in P19 cells. A mechanism in regulating the nuclear-cytoplasm shuttle of CoAM at this stage is unclear, however, other splicing regulators have been reported to be shuttled between the nucleus and the cytoplasm. The rapid decline of CoAM expression in later stages of differentiation might be due to the loss of CoAM-containing cells through apoptosis in the cavity, where a high level of cleaved active caspase-3 was present. CoAM mRNA levels appear to decline more rapidly than CoAM protein levels. At the D3 stage, CoAM protein still remains but CoAM mRNA is almost absent. This is possibly due to the longer protein half-life and the shorter mRNA half-life during degradation processes when cells become apoptotic. The data suggest that cells expressing CoAM are located in the EB cavity. Since CoAM potently represses transcription, it may regulate target gene expression and splicing during essential steps of cavitation at the EB stage.

To confirm the involvement of CoAA in neuronal differentiation, endogenous CoAA protein expression patterns were compared in mouse embryonic tissues at gestational stages of E12.5 and E15.5 bp immunohistochemistry. In the developing brain, CoAA is widely expressed in the neocortex at E12.5. The expression is reduced in the ventricular zone at E15.5, but is enriched in neurons migrated to the cortical plate that raises cerebral cortex. Due to the high expression level of CoAA and low expression levels of CoAM and CoAR, the anti-RRM antibody that detects all three CoAA splicing forms was unable to distinguish from anti-CoAA in immunohistochemical staining (data not shown). However, the data did not exclude the possibility that CoAM and CoAR are present in certain tissues, in which their mRNAs were detected by PCR. In addition, high levels of CoAA expression were detected in almost all fetal tissues at E12.5. By contrast, at E15.5, CoAA expression appeared to be restricted to certain cell types during differentiation. These results nonetheless suggest that the CoAA is a predominant form and is expressed in a cell-specific manner during differentiation in multiple tissues including brain.

Example 3

Decreased CoAA and Increased CoAM Induce Sox6 Expression in P19 Cells

The ability of CoAM to antagonize CoAA function, together with the dramatic decrease of CoAA and the increase of CoAM in the EB cavity, raise the possibility that the switch of CoAA and CoAM might be involved in regulating differentiation. To test this hypothesis, CoAA and CoAM levels were increased by overexpressing CoAM or decreased using RNAi specific for CoAM, and monitoring the expression level of differentiation marker genes, including Sox6 and MAP2. Sox6 is a member of a protein family defined by a high mobility group protein domain, called SRY box. Sox family proteins are widely involved in differentiation including sex determination, and in brain, bone, and muscle development. Sox6 is known to be up-regulated during neuronal differentiation in P19 cells and has a function in pre-mRNA splicing. Since the up-regulation of CoAM is immediately followed by that of Sox6, Sox6 was chosen as one of the marker genes for analysis. CoAM was overexpressed or CoAA RNAi was applied to undifferentiated P19 cells in the absence of RA. The siRNA for CoAA was evaluated in P19 cells. While earlier differentiation markers such as Nanog or Oct4 did not change levels in the absence of RA-induction, the expression of Sox6 and the neuronal marker MAP2 was induced by overexpressing CoAM or by the treatment with CoAA siRNA in the absence of RA. The endogenous CoAA level was decreased during both treatments. The data indicate that CoAA and CoAM may be specific in regulating a subset of genes including Sox6, especially in their downstream differentiation pathways. However, the increased Sox6 level was transient in contrast to the effect of RA-induced, which produced a sustained elevation of Sox6. The relapse effect might be due to the transient increase of CoAM or the transient decrease of CoAA. These data nevertheless suggest that CoAA and CoAM are able to directly or indirectly regulate Sox6. It is still unclear whether CoAA and CoAM are necessary or sufficient to maintain the differentiation program in the absence of RA-induction. In summary, the ratio of CoAA and its dominant negative CoAM may be critical during P19 stem cell differentiation, particularly at the EB stage.

Example 4

Construction of CoAA Minigene

Minigene Design

Figure 3A:
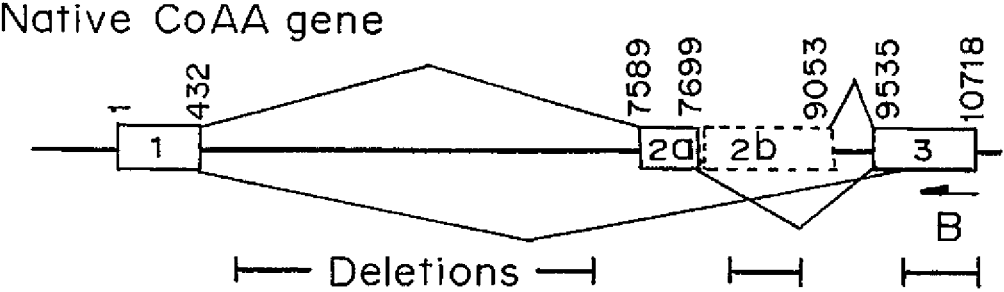
FIG. 3A shows diagrams of the structure of the native CoAA gene and minigene constructions (not to scale). Three CoAA exons are shown as numbered boxes with their alternative splicing events indicated. In the CoAA minigene, the first intron, the second exon (2b) coding the activation domain, and 3' untranslated region within the third exon were shortened. A frame-shift mutation was introduced into the first exon to prevent production of RRM domains. The minigene was linked to a CMV promoter or to its natural 5' sequences (not shown).
Figure 3A:
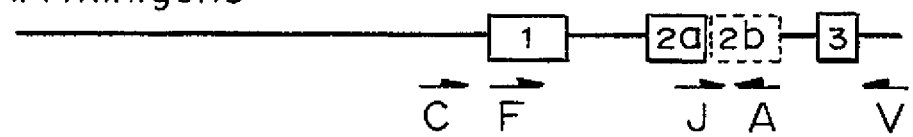

To facilitate promoter analysis, a shortened CoAA minigene was constructed as diagrammed in FIG. 3A. The CoAA minigene was designed to prevent the expression of functional CoAA and CoAM proteins that otherwise might interfere with splicing of its own minigene. Excluding the promoter region, the human CoAA gene spans approximately 11 Kb containing three exons, nt 1-432, 7589-9053, and 9836-10718 (FIG. 3A). Deletions were introduced to the minigene within the first intron (645-7419), within the second exon (7876-8801) that encodes the activation domain, and within the third exon (10044-10718) containing the 3' untranslated region. A one-nucleotide (G) insertion in the first exon disrupted the open reading frame and prevented the production of RRM domains. Expression of CoAA and CoAM transcripts was detected using vector-specific primers that distinguish the minigene and the endogenous gene transcripts. A cassette consisting of the CoAA minigene linked naturally to various fragments of its own promoter was inserted into a promoter-less pcDNA3 vector (BglII to XhoI). As a control, a separate construct was prepared with the CoAA minigene expressed under the control of a CMV promoter in pcDNA3.

Results

Alternative splicing is regulated at multiple levels, particularly when coupled with transcriptional activation. Evidence has suggested that alternative splicing can be regulated through intronic or exonic enhancers and silencers as well as differential usage of promoter and regulatory sequences. The loss of cis-regulatory sequences of amplified CoAA gene has been identified in human cancers, suggesting that this sequence may play an important regulatory role. To investigate if this sequence regulates the alternative splicing of the CoAA gene in P19 cells, a shortened CoAA minigene with intact splicing junctions was constructed. The minigene is under the control of CoAA promoter with or without its native cis-regulating sequences. Thus, the CoAA minigene splicing can be analyzed in P19 cells using transient transfection approach.

Figure 3B:
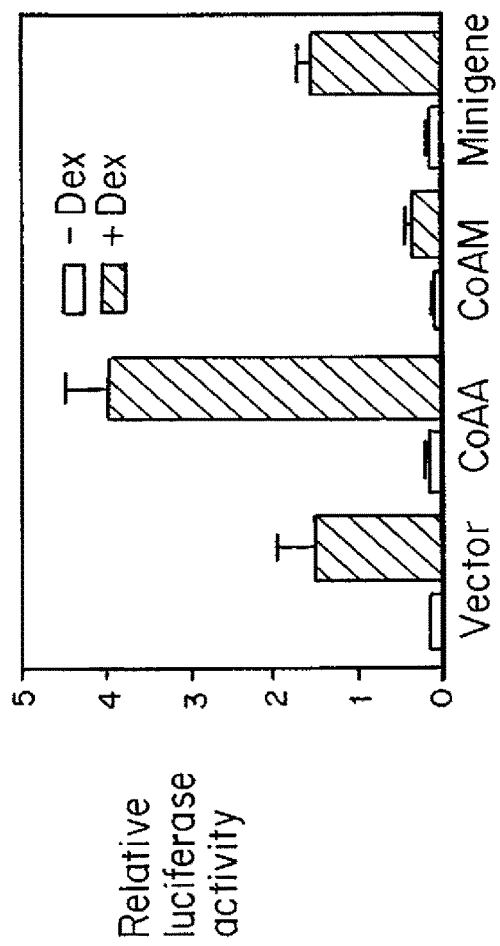
FIG. 3B is a bar graph of showing luciferase activity of the CoAA minigene using CoAA and CoAM as controls.

The design of the minigene ensures that no functional CoAA or CoAM protein is expressed but alternative splicing capability is preserved. The rationale for this design is to eliminate the potential effect of the CoAA protein in regulating its own splicing. The CoAA minigene was constructed with a shortened first large intron, a reading frame-shift mutation in the first exon, and a deletion within the second exon encoding the activation domain (FIG. 3A). A minimum of 160 nucleotides surrounding each splicing site was left intact. The minigene was first evaluated under a CMV promoter by RT-PCR using vector-specific primers to avoid endogenous interference. The results demonstrate that the CoAA minigene was capable of producing both CoAA and CoAM equivalent transcripts, when CoAA and CoAM cDNAs were used as positive controls. The CoAA minigene was also verified to have no coactivator effect on activation of an MMTV-luciferase reporter, which is consistent with the predicted absence of CoAA or CoAM functions (FIG. 3B). Although potential intronic or exonic regulatory elements in the minigene could be affected, the data indicate that the CoAA minigene preserves its splicing capability (FIG. 3B), as well as its switching capacity (see below).

Figure 3C:
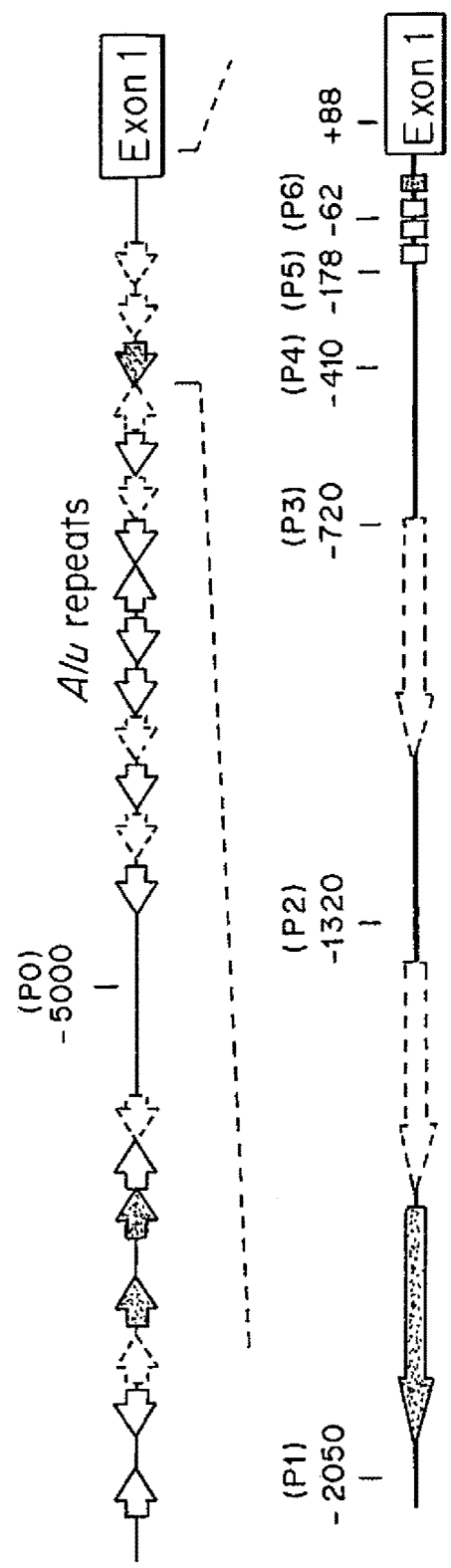
FIG. 3C is a diagram illustrating the CoAA first exon and its upstream regulatory sequences. Orientated arrows depict Alu repeats, Alu-Y in black; Alu-S in gray; and Alu-J in white. Enlarged basal promoter region shows predicted Sp1 and NF-Y binding sites as black or white squares, respectively. Numbers indicate the length of promoter fragments analyzed.
Figure 3D:
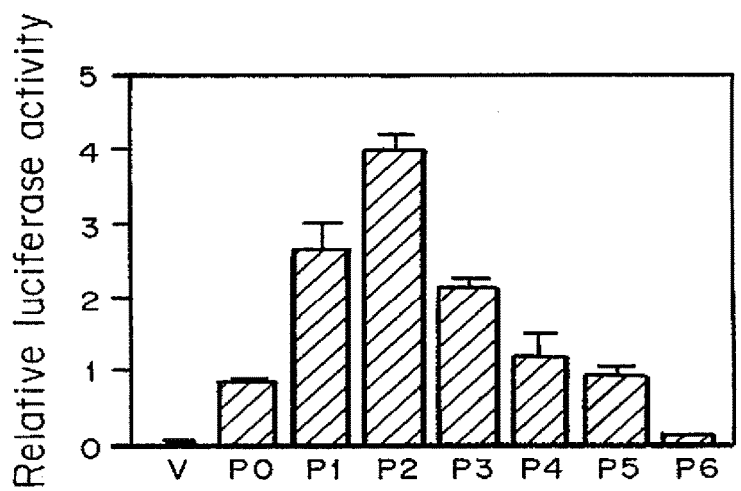
FIG. 3D is a bar graph of luciferase activity due to the CoAA promoter fragments, indicated in FIG. 3C, linked to a luciferase reporter and analyzed by transient transfection assays in P19 stem cells.

The minigene was then constructed under control of the CoAA basal promoter with various lengths of its upstream cis-regulatory sequence to evaluate the regulation of the alternative splicing switch in P19 cells. The human CoAA gene contains a highly GC-rich basal promoter with predicted transcription factor binding sites for Sp1 and NF-Y (FIG. 3C). These transcription factor binding sites and their spacing are highly conserved among human, mouse, and rat species. Within a 10 Kb sequence upstream of the human CoAA gene, there are 21 Alu repeats, which belong to the short interspersed repetitive sequences (SINEs) (FIG. 3C). A similar pattern of SINEs is also present in the mouse CoAA gene. A 5 Kb fragment of the human CoAA upstream sequence has been previously cloned and a series of deletion fragment constructs generated with a luciferase reporter (FIG. 3C-D). Serial deletions of this Alu-rich sequence significantly increased the reporter expression in P19 cells, suggesting that this region contains a cis-acting silencing element in transcription (FIG. 3D). Further deletion of the basal promoter region successively reduced the transcription activity, indicating that an intact basal promoter is essential for gene activation. Together, these data suggest that an Alu-containing cis-regulating element and the CoAA basal promoter are functionally required in P19 cells. The various lengths of the cis-regulating sequences in the CoAA minigene were then compared in subsequent splicing analysis.

Example 5 p54$^{nrb}$ and PSF are Involved in Regulating of the Alternative Splicing of CoAM Chromatin Immunoprecipitation (ChIP)

P19 cells at each stage of differentiation were treated with 1% formaldehyde for 10 min, and the crosslinking was stopped by 125 mM glycine. Cells were lysed and sonicated in the buffer containing 20 mM Tris pH 8.0, 75 mM NaCl, 75 mM KCl, 1 mM EDTA, 1 mM EGTA, 1% Triton X-100, 10% glycerol, 1 mM DTT, and protease inhibitors. Immunoprecipitation was carried out using salmon sperm DNA-blocked protein A/G resin (Upstate), and anti-RNA polymerase II (RNAP II) (8WG16, Covance), or anti-SRp20 (Santa Cruz), or anti-NF-YA (Santa Cruz), or anti-p54$^{nrb}$ (BD biosciences) in the above buffer except with 0.1% Triton at 4° C. overnight. The resin in the absence of antibody was a control. The crosslinking was reversed by eluting with 0.1 M NaHCO$_3$, 1% SDS, 0.3 M NaCl at 65° C. for 4 hours. Purified DNA (Qiagen kit) was subjected to PCR analysis. Input was 1% extract before immunoprecipitation. Primer pairs used are the followings: −80 bp, ggccggaggtagctcttctgac (SEQ ID NO:32), ctccacaggaatggctggcgac (SEQ ID NO:33); −3000 bp, attagaaatgcctttcaagggg (SEQ ID NO:34), cttcggctgatagtggacatac (SEQ ID NO:35); and −8500 bp, caggcggactcggttctttgag (SEQ ID NO:36), caaacctcatatacggagtcgc (SEQ ID NO:37).

Results

The alternative splicing of the CoAA minigene in P19 cells was tested using two well-characterized splicing regulators, polypyrimidine tract binding protein-associated splicing factor (PSF) and p54 nuclear RNA-binding protein (p54$^{nrb}$). PSF and p54$^{nrb}$ are RRM-containing proteins that have been suggested to regulate pre-mRNA splicing and to associate with transcription and splicing complexes. Both endogenous PSF and p54$^{nrb}$ are present in undifferentiated P19 cells (not shown). In the absence of RA induction, overexpression of either PSF or p54$^{nrb}$ in undifferentiated P19 EC cells induced a very significant elevation of endogenous CoAA, but not of CoAA. The stimulation of CoAM expression by PSF and p54$^{nrb}$ was also evident in cells transfected with the P0 minigene, that carries the cis-regulating Alu-containing sequence (−5000 to +88). However, there was much less induction of CoAM transcript when the CoAA P2 minigene was driven only by the CoAA basal promoter (−1320 to +88) under the same condition. In addition, p54$^{nrb}$, but not PSF, significantly induced CoAM expression from the CoAA minigene driven by a CMV promoter. These data suggest that inclusion of the cis-regulating sequence in the minigene promotes CoAM splicing similar to that in the endogenous gene. In contrast, CMV has a different promoter protein complex assembly, which may permit regulation by p54$^{nrb}$ but not by PSF. The p54$^{nrb}$ mRNA is relatively constant while PSF mRNA increased in RA-induced P19 cells as detected by RT-PCR analysis (not shown). There is no apparent correlation between the expression levels of p54$^{nrb}$ and PSF and the switch of CoAA to CoAM during RA-induced differentiation. Thus, the involvement of p54$^{nrb}$ and PSF in regulating alternative splicing of the CoAA gene might be due to their protein modifications at the particular differentiation stage. RA may induce certain signaling pathways that lead to the p54$^{nrb}$/PSF activation in a splicing complex responsible for CoAM expression. The data minimally suggest that the alternative splicing of CoAM can be regulated through PSF and p54$^{nrb}$, although other splicing factors might also be involved. The data also indicate that the promoter and upstream cis-regulating sequences are involved in alternative splicing decisions.

Figure 4:
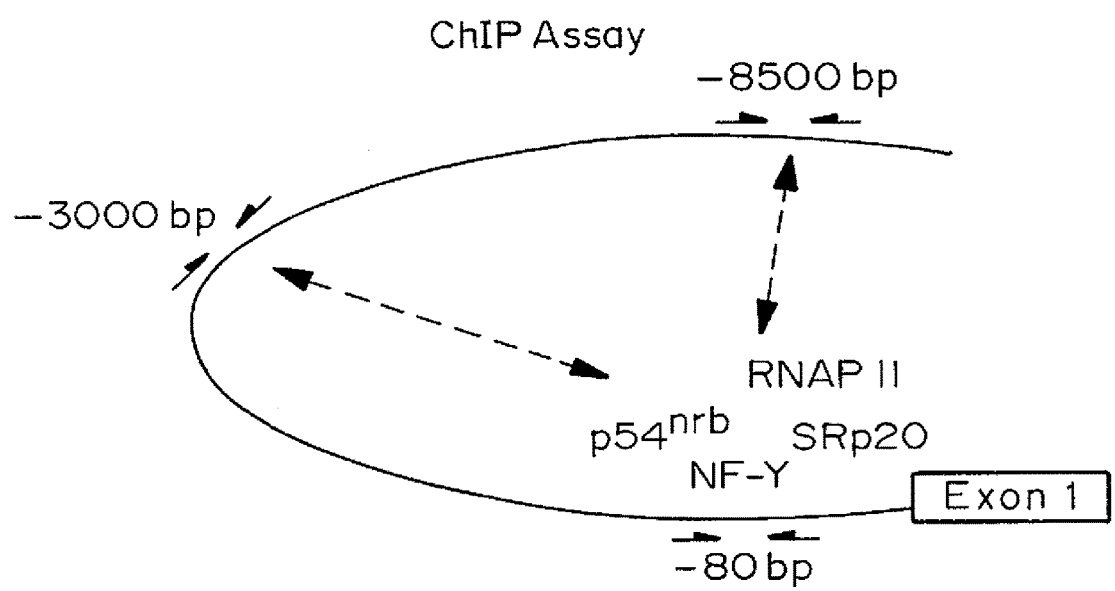
FIG. 4 is a diagram depicting the interactions (dashed arrows) between cis-regulating sequences and potential splicing and promoter complexes containing RNAP II, $p54^{nrb}$, SRp20, and NF-Y. Paired arrows indicate the primer locations.
Figure 5A:
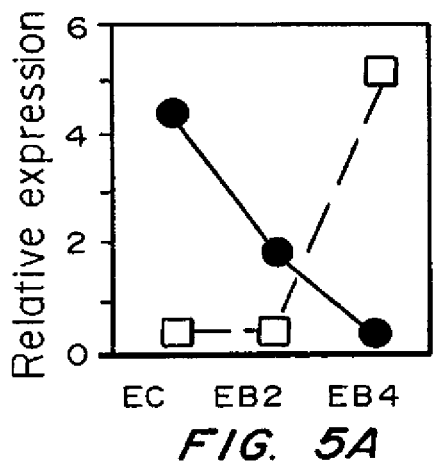
FIGS. 5A-E are graphs showing relative expression of CoAA and CoAM at the indicated stage of development in cells transfected with the native gene (A) with P0-(B), P2-(C), P4-(D), or CMV-minigene (E). GAPDH served as a control. Endogenous CoAA and CoAM transcripts from native CoAA gene were controls.
Figure 5B:
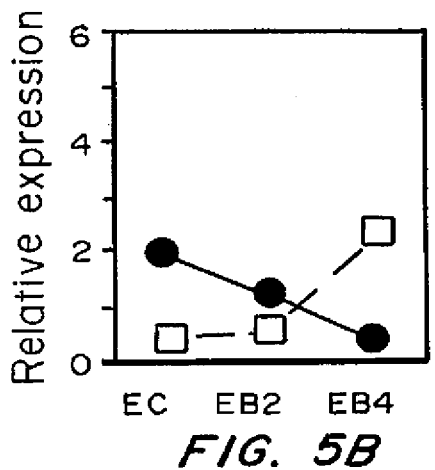
Figure 5C:
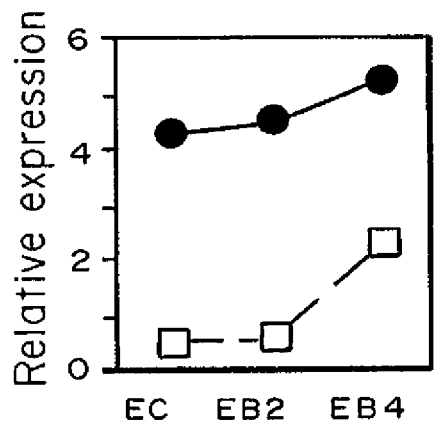
Figure 5D:
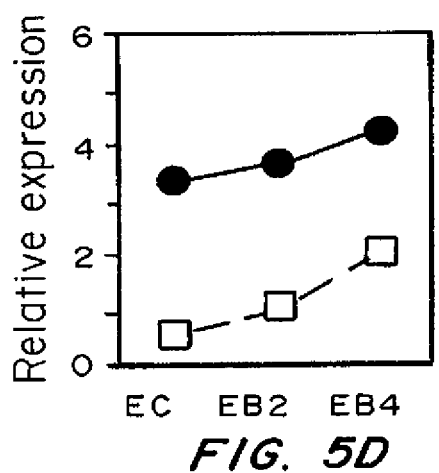
Figure 5E:
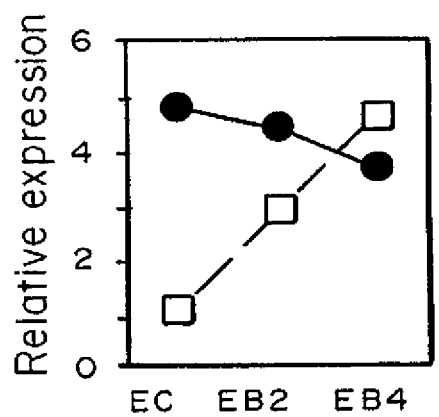
Figure 6:
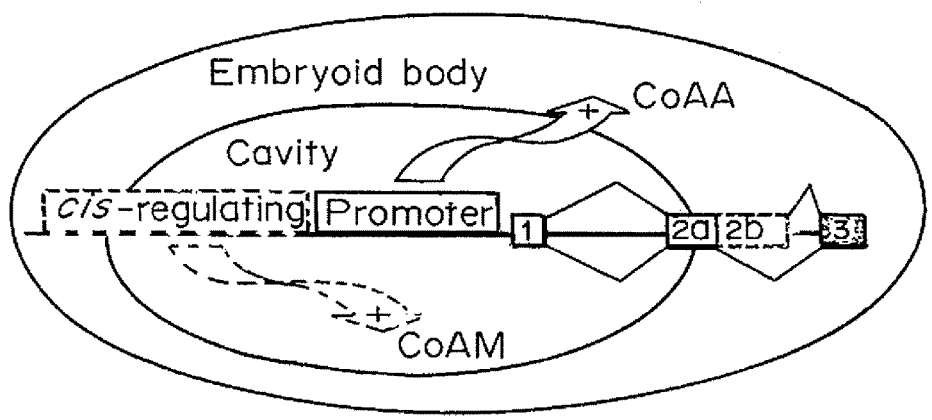
FIG. 6 is a diagram showing a model of CoAA alternative splicing regulation in the embryoid body of stem cells.

To seek potential mechanism for the involvement of CoAA promoter and regulatory sequence in alternative splicing, chromatin immunoprecipitation (ChIP) analysis (FIG. 4) was performed using antibodies against p54$^{nrb}$, RNA polymerase II (RNAP II), one of the SR proteins named SRp20, and transcription factor NF-Y, whose binding sites are present in the CoAA promoter. ChIP analysis suggests that there are physical interactions of protein complexes containing p54$^{nrb}$ RNAP II, SRp20 and NF-Y with the CoAA basal promoter region as well as the Alu-containing cis-regulating sequences. NF-Y, RNAP II, p54$^{nrb}$ and SRp20 all strongly interact with the CoAA basal promoter region (−80 bp) at all time points of RA-induction. However, they have varied interaction strength with the cis-regulating sequences (−3000 bp and −8500 bp) during differentiation. In particular, their interactions are generally increased at the EB2 stage. 54$^{nrb}$ however, has a different interacting pattern, in which the interaction with the −3000 bp region is more constant than the interaction with the −8000 bp region. The alteration of interaction level during RA-induced differentiation is correlated with the early stage of EB formation. Although the details of the interacting pattern during differentiation may be complex, the data minimally suggest that there are interactions among promoter/enhancer complexes and splicing factors including p54$^{nrb}$. These data further support that alternative splicing regulation may require the cis-regulating sequence and the basal promoter of the CoAA gene.

Example 6

The Cis-Regulating Sequence is Responsible for Alternative Splicing Switch from CoAA to CoAM During P19 Cell Differentiation To examine the upstream cis-regulating sequence in regulating alternative splicing of CoAA and CoAM during P19 cell differentiation, the CoAA minigene with different lengths of the cis-regulating sequence were compared. During RA-induced EB formation, the endogenous CoAA gene undergoes a dramatic switch in alternative splicing from CoAA to CoAM (FIGS. 5A-E). The P0 (−5000 to +88) minigene, though at a reduced expression level, undergoes a similar switch, which has similar timing to that of the endogenous CoAA gene at stage EB4. In contrast, the P2 (−1320 to +88) and the P4 (−410 to +88) minigenes containing the basal promoter region have relatively high levels of expression of both CoAA and CoAM but are unable to induce a complete switch after RA induction (FIGS. 5A-E). There was up-regulation of CoAM, but the down-regulation of CoAA was totally absent. Thus, when compared to the endogenous gene or P0 minigene, the expression of CoAM transcript from the P2 and P4 minigene fails to remain dominant at the EB4 stage. In addition, the CMV-driven minigene, in which the CoAA basal promoter was substituted with a CMV promoter, shows an incomplete switch in expression between CoAA and CoAM upon RA-induction. Quantification of the PCR products in the gel is shown in the lower panels of FIGS. 5A-E. The transcriptional level appears to be linked with alternative splicing on the CoAA minigene. The higher transcriptional rates in the P2 or P4 minigene are correlated with inadequate CoAM splicing, whereas a lower transcriptional rate in the P0 minigene shows an almost complete switch from CoAA transcript to CoAM transcript. These data imply a linked transcription rate and alternative splicing regulation, and again suggests that regulatory sequence and promoter context are involved in regulating alternative splicing decisions. As switched expression of CoAA and CoAM is correlated with EB cavitation during stem cell differentiation, the CoAA gene at this stage might be regulated at the alternative splicing level through its promoter and cis-regulating sequence.

Example 7

CoAA C Terminal Repeats are Shared by Multiple Oncoproteins

Pattern Profile and Sequence Analyses

The protein databases of Swiss-Prot (release 44.3; 156998 entries) and TrEMBL (release 27.3; 1379120 entries) were analyzed with ScanProsite program. Prosite syntax scanned for the YxxQ motifs: Y-{P}(1,2)-Q(1,2)-X(1,4)-Y-{P}(1,2)-Q(1,2)-X(1,4)-Y-{P}(1,2)-Q(1,2). The taxonomic species filter was set as Homo sapiens, Mus musculus, Rattus norvegicus and Bos taurus. Sequences identified with more than three hits, i.e., nine copies of the motifs, were selected for analysis. Alu repeats within the regulatory sequences of the CoAA gene were identified using Censor Server at Genetic Information Research Institute and BLAST search at NCBI. Transcription factor binding sites within the CoAA basal promoter were predicted by the TFSEARCH program at Computational Biology Research Center (www.cbrc.jp).

Results

The unique activation domain of CoAA contains 27 copies of repeated tyrosine- and glutamine-rich sequences (termed YxxQ motifs). These sequence motifs possessed robust transcriptional activity. To obtain functional insight into these unique sequence repeats of CoAA, pattern and profile searches we performed with SWISS-PROT/TrEMBL databases to search for additional proteins that might contain similar repeats. The rationale was that even though a large number of proteins might carry a random YxxQ-like sequence, only a few proteins would have the sequence repeated many times. Surprisingly, 44 out of 52 returned entries within the mammalian protein databases matched to six proteins with multiple copies of repeated tyrosine- and glutamine-rich sequences. These matched proteins are the EWS family members EWS, TLS/FUS, and TAFII68; the oncoprotein SYT; the SWI/SNF complex largest subunit BAF250; and CoAA itself. All six YxxQ-rich proteins are known to be involved in transcriptional activation or in regulation of alternative splicing, suggesting that these sequences function in gene regulation. In addition, the oncogenic activity of the EWS family and SYT depend upon the presence of their N-terminal YxxQ-rich sequences, implicating the repeating sequences in oncogenesis. These findings led us to search for CoAA gene alterations in human cancers.

Example 8

CoAA Gene Amplification in Human Cancers

Fluorescent In Situ Hybridization (FISH) Analysis

Tumor tissue paraffin sections including tumor arrays (Medical College of Georgia and InnoGenex) were evaluated histologically by study pathologists before FISH analysis. The paraffin-embedded slides were baked, deparaffinized, treated with tissue pre-treatment reagents (Insitus Biotechnologies), and hybridized using Vysis reagents. A bacterial artificial chromosome (BAC) clone (RP11-527H7, 200 Kb, Children's Hospital Oakland Research Institute) containing the CoAA gene, confirmed by PCR, was labeled with SpectrumRed dUTP (Nick Translation Kit, Vysis) according to the manufacturer's protocol to produce the FISH probe. Chromosome 11 centromeric alpha satellite probe CEP11-D11Z1 (Vysis) was labeled with SpectrumGreen dUTP and applied simultaneously as a control probe for dual-color visualization. Slides were counterstained with DAPI before visualization with fluorescence microscopy.

Results

The human CoAA gene (gene symbol RBM14) is located at chromosome 11q13, a locus that has been shown to be rearranged and amplified in multiple human cancers (Koreth, J., et al., *J Pathol*, 187:28-38 (1999); Lammie, G. A., and Peters, G., *Cancer Cells* 3: 413-420 (1991)). To search for potential aberrations in the CoAA gene, fluorescence in situ hybridization (FISH) was performed on interphase chromosomes of human cancer tissues using the 210 Kb BAC clone RP11-527H7 as probe. The probe was verified for the presence of the entire CoAA gene by PCR. FISH using a normal peripheral lymphocyte metaphase chromosome was also performed to verify that the CoAA probe (red) localized to its expected position near a chromosome 11 centromere control probe (green). FISH analysis of interphase chromosomes from tumors suggested that gene amplification of CoAA was present in a non-small cell lung carcinoma and a lymphoma, note increased red signal relative to green signal, but not in a breast cancer. The data shows a section of a lung carcinoma at increasing magnifications after hybridization with CoAA probe. Although amplification was found in a large number of cancer cells, significant heterogeneity of cell populations was present. The gene copy number increase varied widely. Using multiple tumor assays, CoAA gene amplification was also detected in squamous cell skin cancer (3/4), pancreatic cancer (3/4), ovarian cancer (1/2), and in certain other types of primary cancers (Table 1).

There are several noticeable features of CoAA gene amplification. The copy number increase in a single nucleus can be high, ranging from several to possibly over 100 copies, if considering the high probability of double minute chromosomes in primary tumors. Lung cancers have greater signal intensity as well as the highest incidence of CoAA amplification. Examination of the same section using brightfield microscopy suggested that tumor cells with amplified CoAA are very small in size and are less differentiated with high nucleus-cytoplasmic ratio or scant cytoplasm. These cells were frequently found in stromal regions adjacent to the cancer, although they were also present in the tumor mass. Regardless of the tumor origin, significant heterogeneity of the cell population, small and irregular nuclei, and enriched blood vessels are typical morphologies in tumor areas of CoAA amplification. When multiple tumor, non-small cell lung cancer (NSCLC) and breast cancer arrays were compared by FISH analysis, amplification was found only in 4.5% (2/44) of breast cancers, but in 67.7% (21/31) of lung cancers analyzed (Table 1), suggesting that CoAA amplification preferentially occurs in a subset of human cancers including lung cancer. CoAA amplification was also present in lymphomas, squamous cell skin cancers, pancreatic cancers, and gastric cancers.

TABLE 1

Gene amplification of CoAA in human cancers as determined by fluorescent in situ hybridization analysis using BAC clone RP11-527H7 as probe

| TMA | Tissue type | Positive/total samples | Intensity* |
|---|---|---|---|
| Multiple tumor array | Liver | 0/4 | – |
| | Lung | 3/3 | ++++ |
| | Pancreas | 3/4 | +++ |
| | Melanoma | 1/5 | + |
| | Esophageal | 1/2 | + |
| | Gastric | 1/2 | ++ |
| | Colon | 0/3 | – |
| | Breast | 0/4 | – |
| | Kidney | 0/3 | – |
| | Astrocytoma | 0/4 | – |
| | Lymphoma | 3/7 | +++ |
| | Mesothelioma | 0/5 | – |
| | Squamous skin | 3/4 | ++++ |
| | Basal cell | 1/4 | + |
| | Carcinoids | 0/5 | – |
| | Neuroblastoma | 0/1 | – |
| | Undifferentiated | 2/5 | + |
| | Sarcoma | 0/6 | – |
| | Stomach | 1/2 | + |
| | Prostate | 0/4 | – |
| | Thyroid | 0/2 | – |
| | Ovary | 1/2 | + |
| Breast cancer array | Normal breast | 0/5 | – |
| | Fibroadenoma | 0/5 | – |
| | Carcinoma in situ | 0/2 | – |
| | Medullary carcinoma | 0/2 | – |
| | Lobular carcinoma | 0/5 | – |
| | Ductal carcinoma | 2/25 | + |
| | Paired metastasis | 0/5 | – |
| Lung cancer array | Normal lung | 0/4 | – |
| | Hyperplasia | 2/8 | + |
| | Carcinoma | 5/5 | ++++ |
| | Carcinoma-necrosis | 0/2 | – |
| | Paired adjacent tissue | 6/8 | +++ |
| | Paired carcinoma | 8/8 | ++++ |

*The intensity of amplification is scored as completely negative (–), weakly positive (+) with 3-4 copies per interphase, positive (++) with 5-10 copies per interphase, strongly positive (+++) with the presence of over 10 copies per interphase, and very strongly positive (++++), with the presence of over 20 copies per interphase.

Example 9

Independent CoAA Amplification from CCND1

CCND1 is located 3 Mb distal to the CoAA gene. CCND1 is known to be amplified in lung and skin cancers and contributes to the amplicon selection at 11q13. To determine if CoAA is amplified individually or co-amplifies with CCND1, quantitative real-time PCR analysis was carried out to detect the copy number changes on both CoAA and CCND1 in 20 primary lung cancers, 10 squamous cell skin cancers, 12 lymphomas, and 6 lung cancer cell lines. The data confirmed that the CoAA gene was amplified in the majority of lung cancer and squamous skin cancers, a number of lymphomas, and two lung cancer cell lines NCI-H69 and NCI-H2126 (FIG. 7). However, the amplification patterns showed a clear distinction between CoAA and CCND1. In several cases, CoAA was amplified more than 6-fold, whereas CCND1 was not amplified (FIG. 7). Although in some cases CoAA and CCND1 did co-amplify, the copy number increases from the two genes are not correlated. Thus, the data support that CoAA can independently amplify, and might contribute to the amplicon selection at 11q13 in addition to CCND1. In addition, CoAA amplification detected by FISH was detected by quantitative PCR in stomach cancers, melanomas, and sarcomas (not shown). Since PCR detects the average gene copy changes of an entire sample, the individual positive cells may have a higher copy number increase of CoAA, as suggested by FISH analysis (FIG. 1). In summary, amplification of the CoAA gene at least 2-fold above normal was detected by PCR in 55% (11/20) of lung cancers, 70% (7/10) of skin cancers, and 33% (4/12) of lymphomas.

Example 10

Figure 7A:
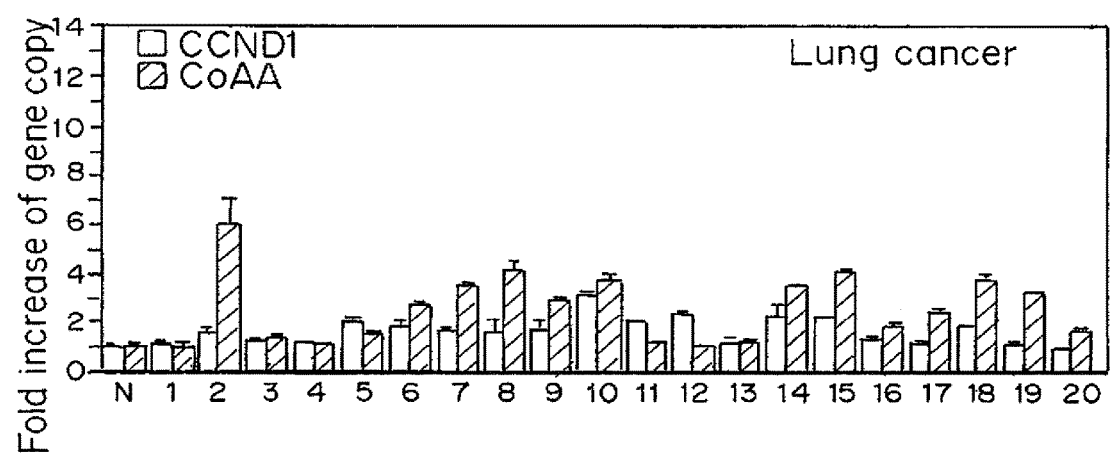
FIGS. 7A-D are bar graphs of fold increase in gene copy number in the indicated lung cancer cells (A), lung cancer cell line (B), skin cancer cells (C), and lymphoma cell line. Normal genomic DNA control is indicated as N. Lung cancers include squamous cell lung carcinoma (1, 2, 3, 5, 6, 17, 18, 19, 20) and adenocarcinoma (4, 7, 8, 9, 10, 11, 12, 13, 14, 15, 16). Lymphomas include follicular lymphoma (1, 2, 3, 4, 5, 6, 7, 8, 9), and large B cell lymphoma (10, 11, 12).
Figure 7B:
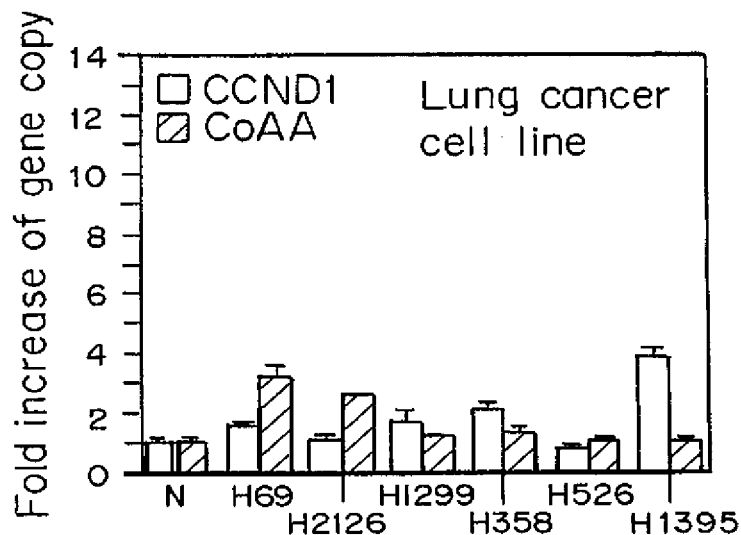
Figure 7C:
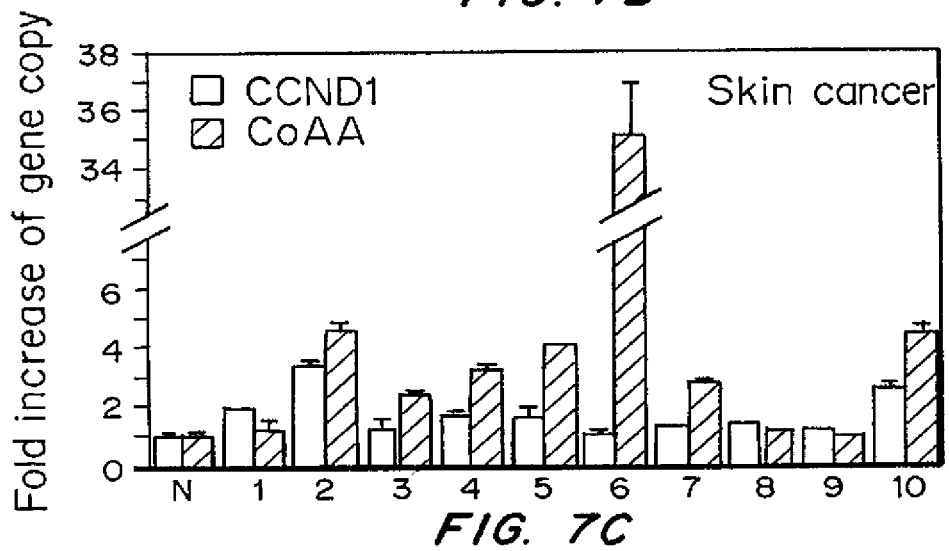
Figure 7D:
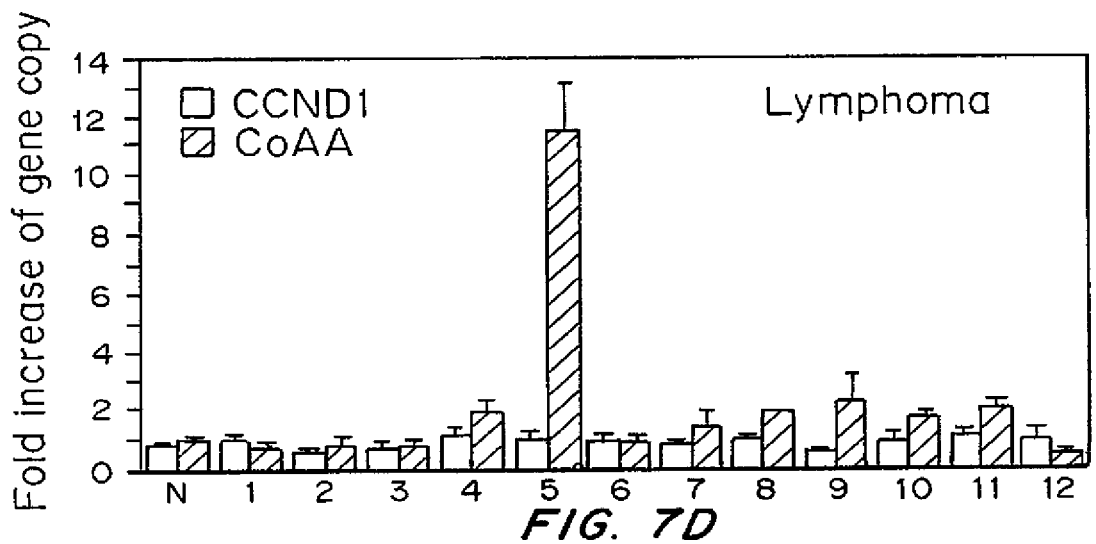
Figure 8:
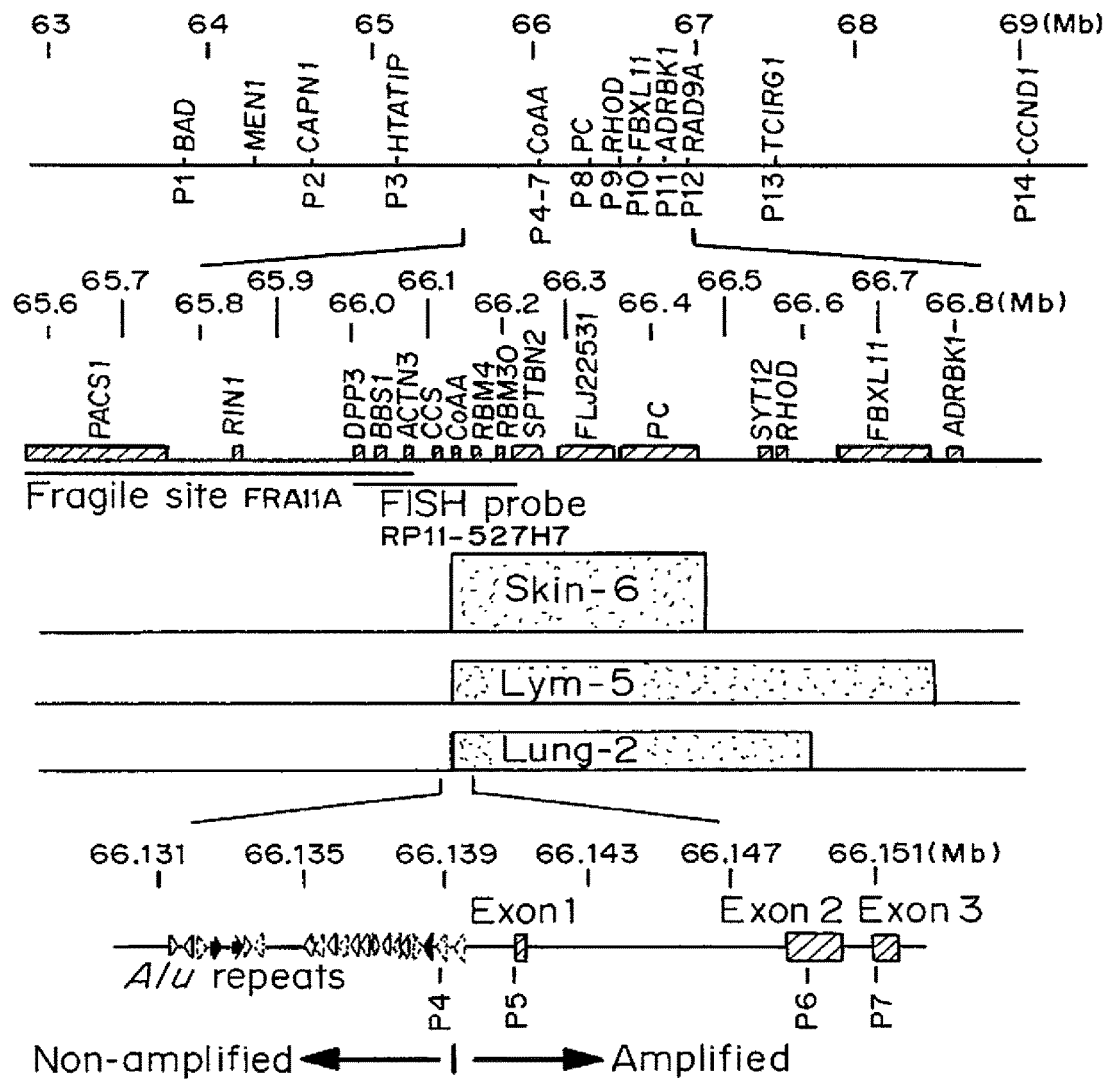
FIG. 8 is a diagram illustrating the human CoAA gene locus at chromosome 11q13 (drawn to three successively larger scales, after NCBI). Genes are shown on the top of each line and labeled in italics. Fourteen pairs of primers used for amplicon mapping are indicated below the lines. The fragile site FRA11A and FISH BAC probe RP11-527H7 are shown with their spanning regions indicated. The locations of the three mapped amplicons (Skin-6, Lym-5 and Lung-2) are depicted as gray boxes. In the enlarged bottom panel, the CoAA gene is shown with three exons and its 5' regulatory sequence is shown with 21 Alu repeats upstream of the basal promoter. Multiple Alu repeats are shown by orientated arrows (Alu-Y, black; Alu-S, gray; Alu-J, white). The boundary between amplified and non-amplified sequences is indicated with a bar.
Figure 9:
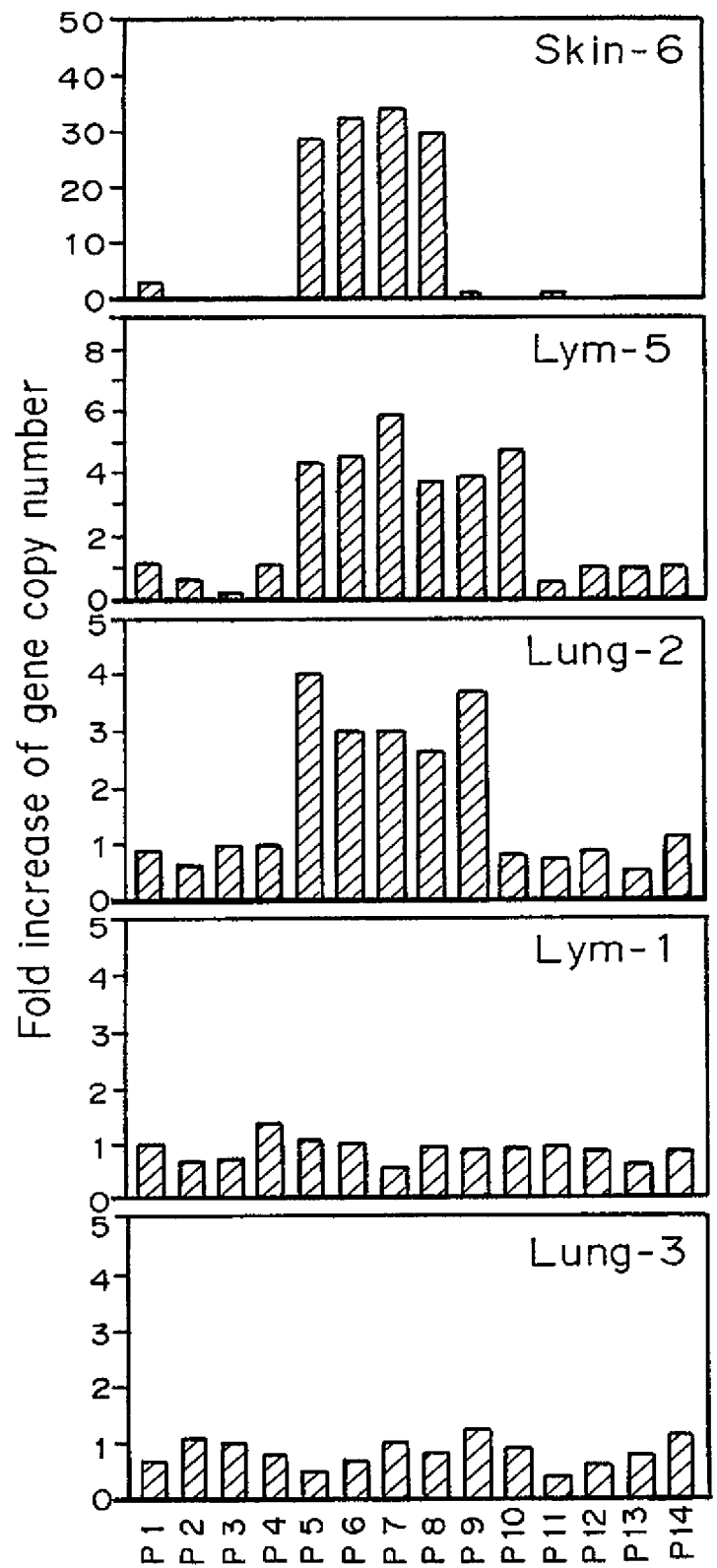
FIG. 9 is a panel of bar graphs quantitative real-time PCR results using DNA from tumors with identifying numbers corresponding to numbers in FIG. 7. The locations of 14 primer pairs (P1-P14) used in the mapping are shown in FIG. 8. Two non-amplified tumors, a lymphoma and a squamous cell lung cancer were used as negative controls. Fold increase of gene copy number was determined as in FIG. 7.

Loss of 5' Regulatory Sequences of the CoAA Gene is Associated with CoAA Amplicons In order to address the molecular mechanism of CoAA amplification, the CoAA amplicon was mapped using primers spanning approximately 5 Mb of sequence surrounding the CoAA gene (FIG. 8). Three tumors identified in FIG. 7 with ≥6-fold of CoAA gene amplification including a skin cancer (Skin-6), a lung cancer (Lung-2), and a lymphoma (Lym-5) were used for amplicon mapping. Fourteen pairs of primers (P1-P14) were verified for efficiency, and for accurate size of PCR products using normal human control DNA before use. The primer locations are indicated in FIG. 8, and quantitative PCR data is shown in FIG. 9. The mapped amplicons in the three cancers overlapped and were approximately 300-650 Kb in size (FIG. 8). These results have been repeated using different control samples including normal genomic DNA and multiple non-amplified tumor DNA. Although the 3' boundaries of these amplicons were different, the 5' boundaries were consistently located immediately upstream of the CoAA coding sequence, between primer pairs P4 and P5 (FIG. 9). Although six genes are located within the region common to the three amplicons, only the CoAA gene had its upstream regulatory sequences invariably lost from all amplicons. Noticeably, a fragile site, FRA11A, is located immediately upstream of all the amplicons (FIG. 8) (Zainabadi, K. et al. Genomics 85:704-714 (2005); Buttel, I. et al., Ann N Y Acad Sci, 1028:14-27 (2004)). Based on the Breakage-Fusion-Bridge theory of gene amplification (Coquelle, A. et al. Cell 89:215-225 (1997), FRA11A together with other downstream fragile sequences may contribute to the establishment of the CoAA amplicon boundaries. Together, the data confirm that CoAA has its own amplicon excluding CCND1. Importantly, the loss of the sequence immediately upstream of the CoAA coding region occurs in three different types of tumors analyzed. The loss of these sequences derepresses CoAA gene expression.

Example 11

CoAA Protein is Overexpressed in CoAA-Amplified Cancers

To determine if gene amplification leads to altered CoAA protein expression, an affinity-purified polyclonal antibody against CoAA was generated. The antibody recognized a single band of the expected size in a Western blot analysis. In addition, the staining had the expected nuclear distribution in an immunofluorescence analysis. Immunohistochemical staining on tumors were identified by FISH. CoAA overexpression at a high level was detected in amplified lung and skin tumors compared to normal lung and skin tissue as controls. In normal tissues, CoAA expression was detected in a subset of cells including the basal layer of skin, suggesting it has function in normal tissues. A high level of CoAA protein expression was also detected in amplified, but not in non-amplified, lung cancers when adjacent tissue sections were compared by FISH and immunohistochemistry analyses. Although CoAA protein expression was also present in some non-amplified tumor cells, a high level of CoAA protein expression correlated with the CoAA gene amplification. Notably, an area with high level of CoAA protein expression showed CoAA gene amplification when adjacent sections were analyzed. In addition, CoAA protein was significantly expressed in the three tumors for which we have mapped amplicons (Skin-6, Lym-5, and Lung-2). Together, these data support the idea that CoAA gene amplification leads to CoAA protein overexpression.

Example 12

CoAA mRNA is Up-Regulated in Human Cancers

Northern Dot Blot Analysis

The Northern dot blot containing 100 paired normal and primary tumor cDNAs was obtained from Clontech (Cancer Profiling Array II, #7847-1). The blot contained normalized mRNA isolated from tumor and corresponding normal tissues from individual cancer patients. The CoAA probe was prepared by random-primed $^{32}$P-DNA synthesis using human CoAA full-length cDNA as template. Northern hybridization was performed according to manufacturer's protocol.

Results

In addition to the protein level, CoAA expression at the mRNA level was examined in human primary tumors. Northern dot blot analysis was performed with 100 paired normal and primary tumor tissues from 10 tumor types. The results suggest that CoAA has elevated mRNA expression in 60-80% of lung, skin, stomach, and testicular cancers, and in 30-50% of thyroid, uterus, cervix, breast, ovarian, and colon cancers. It is currently unclear how many of these samples with mRNA up-regulation contain CoAA gene amplification; however, the relative higher percentage of CoAA mRNA up-regulation in lung and skin cancers was consistent with our analyses by FISH and quantitative PCR (FIG. 7). These data nevertheless indicate that CoAA mRNA expression was increased in a large number of primary cancers.

Example 13

CoAA has Transforming Activity

Mutagenesis of the YxxQ Domain

Tyrosine to alanine substitutions in each of the 27 copies of the YxxQ motifs of CoAA were generated by gene synthesis (MCLab). The synthetic AxxQ-containing region was subcloned into the wild-type CoAA construct replacing the YxxQ sequences. The accuracy of the AxxQ mutant was confirmed by full-length nucleotide sequencing, restriction mapping, and Western blot analyses before use.

Transformation Assay

The CoAA YxxQ domain and the AxxQ domain (aa 307-547) were joined to the Fli-1 DNA-binding domain to create fusion proteins similar to the EWS-Fli-1 fusion protein derived from a sarcoma. Mouse NIH3T3 cells (ATCC, CRL-1658) were stably transfected with Flag-tagged full-length CoAA, full-length AxxQ mutant, YxxQ-Fli-1, AxxQ-Fli-1, or EWS-Fli-1. Empty vector was transfected as control. Stably transfected cells were selected using 400 µg/ml of G418. Positive clones containing stably transfected DNA were identified by PCR with genomic DNA, and the protein expression levels of each transfected clone was monitored by immunofluorescent staining using anti-FLAG antibody. Stable clones were assayed for anchorage-independent growth in soft agar (0.34% low melting point agarose in DMEM containing 15% FCS). The numbers of colonies in duplicated plates were counted. For contact inhibition assay, stably transfected cells were plated onto a 24-well plate with $4 \times 10^3$ cells per well in triplicate, and the cell number was counted after trypsinizing every 24 hrs for 8 days. Cells were fed twice a week. Data are shown as means of triplicate±standard errors.

Transient Transfection and RNA Interference

Monkey kidney CV-1 cells (ATCC, CCL-70) were maintained in Dulbecco's modified Eagle's medium (DMEM) supplemented with 10% fetal bovine serum and 5 µg/ml penicillin/streptomycin in 5% $CO_2$ at 37° C. NIH3T3 cells (ATCC, CRL-1658) were maintained under the same conditions except with 10% donor bovine serum. NCI-H69 lung cancer cells (ATCC, HTB-119) were cultured in RPMI 1640 medium supplemented with 2 mM L-glutamine, 10 mM HEPES, and 10% fetal bovine serum. Cells were transfected in triplicate in 24-well or 96-well plates using Lipofectamine™ (Invitrogen). The target sequence of CoAA siRNA is 5'-GUAACCAGCCAUCCUCUUA-3' (SEQ ID NO:38); the control siRNA is 5'-UAGCGACUAAACA-CAUCAA-3' (SEQ ID NO:39) (Dharmacon). H69 cells were transfected with CoAA or control siRNA at indicated concentrations for 16 hours before adding 10 µM BrdU (Sigma) for 4 hours. Cells were fixed, blocked, treated with monoclonal anti-BrdU antibody (Santa Cruz Biotechnologies, 1:200). The BrdU incorporation was detected with ECL reagents (Amersham Pharmacia) using a Dynex luminometer. Relative light units are shown as means of triplicate±standard errors. For promoter analysis, CoAA promoter fragments were cloned by PCR using BAC clone RP11-527H7 as template. Each promoter fragment was inserted into a promoter-less PXP2 luciferase vector. Full-length human CoAA plasmid was cotransfected with the reporter plasmids, when applicable, for 16 hours before harvest. Relative luciferase activities were measured using a Dynex luminometer and shown as means of triplicate transfections±standard errors.

Results

Figure 10A:
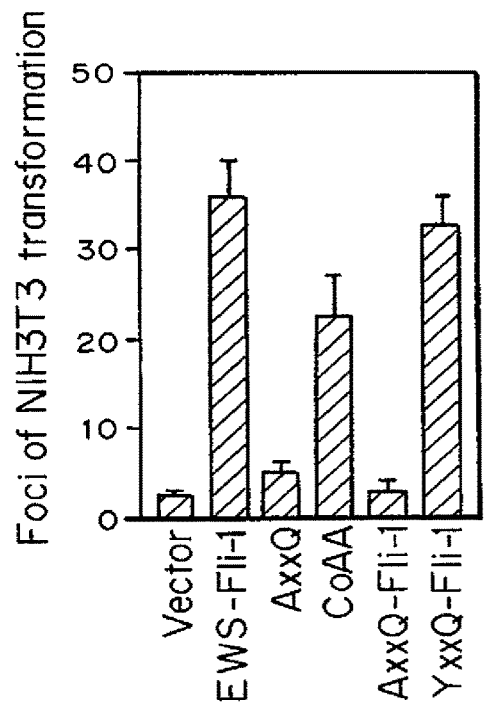
FIG. 10A is a bar graph of fold expression in NIH373 cells transfected with empty vector as control, or with expression plasmids for EWS-Fli-1, wild-type CoAA, AxxQ mutant, YxxQ-Fli-1, and AxxQ-Fli-1.
Figure 10B:
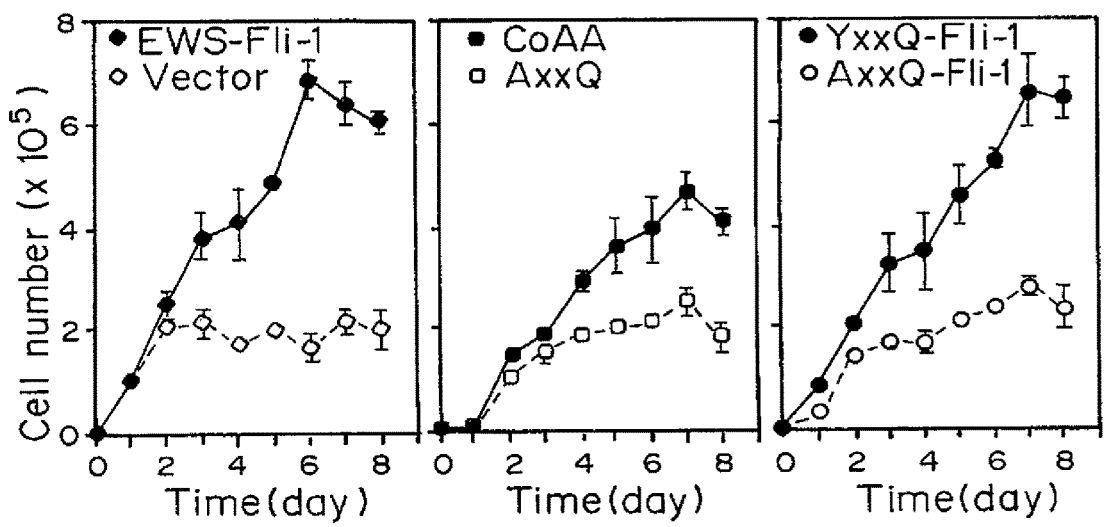
FIG. 10B is a panel of line graphs of cell number ($\times 10^5$) versus time (days) of the transformed cells of FIG. 10A.
Figure 10C:
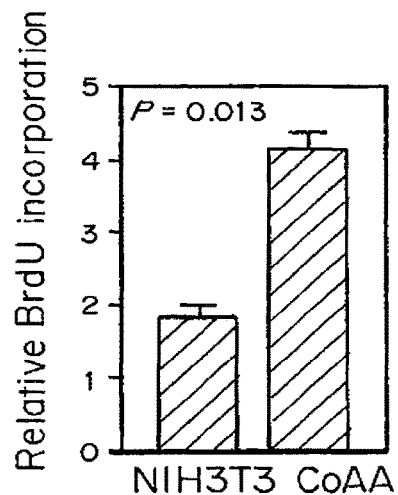
FIG. 10C is a bar graph of relative BrdU incorporation in CoAA-transfected NIH3T3 cells.
Figure 10D:
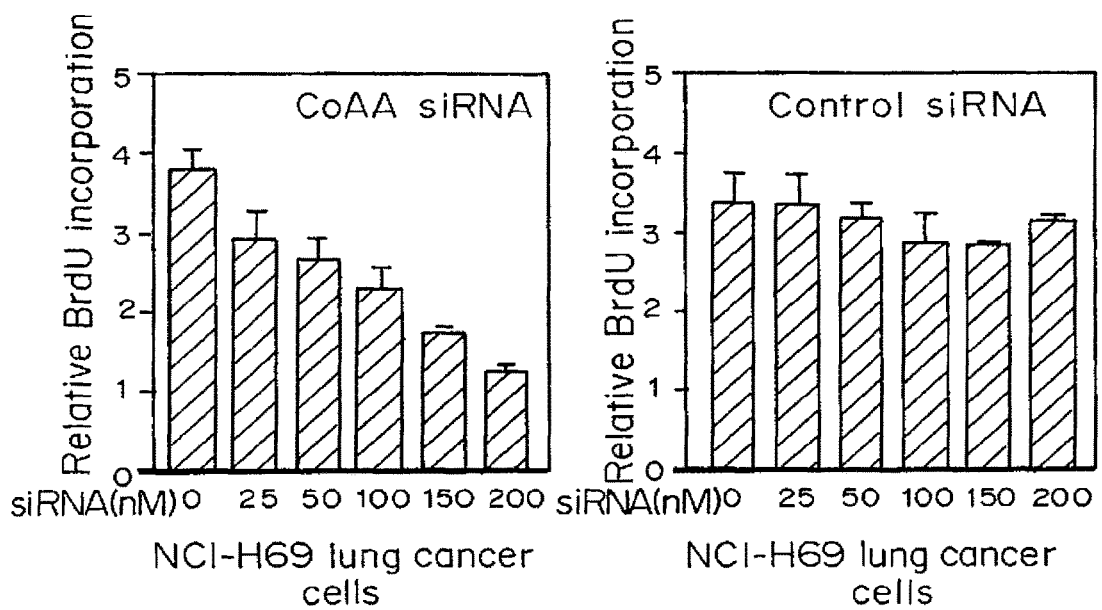
FIG. 10D is a bar graph of relative BrdU incorporation in NCI-H69 lung cancer cells treated with siRNA of CoAA. The increasing amounts of CoAA siRNA (left panel) and control siRNA (right panel) used are as indicated.

To investigate whether increased CoAA expression would directly induce the transformed phenotype, the transforming capability of CoAA protein in NIH3T3 soft agar assays was examined. CoAA contains an activation domain homologous to the EWS N terminus which is known to have transforming activity. An expression plasmid containing full-length CoAA cDNA was constructed as well as an expression plasmid containing a fusion of the CoAA activation domain to transcription factor Fli-1 (YxxQ-Fli-1), mimicking the EWS-Fli-1 fusion that occurs in Ewing's sacroma. This allows one to determine if the CoAA activation domain has comparable transforming activities. Since the CoAA activation domain requires its tyrosine residues for transcriptional activity (not shown), a tyrosine to alanine mutant (AxxQ) was generated in which 27 tyrosines were mutated to alanines. The accuracy of the AxxQ mutant was confirmed through complete nucleotide sequencing. The full-length AxxQ and AxxQ-Fli-1 served as negative controls and EWS-Fli-1 as a positive control in the assays. Stable NIH3T3 cell lines transfected with each expression plasmid were selected. The protein expression level in each stable cell clone was comparable when analyzed by immunofluorescence using anti-FLAG tag antibody. The results of transformation assays showed that wild-type CoAA, but not the AxxQ mutant, promoted formation of colonies in soft agar. The YxxQ-Fli-1 construct showed transformation activity comparable to EWS-Fli-1, suggesting that the activation domain of CoAA can substitute for that of EWS. Quantification of the results is shown in FIG. 10A. Consistent with the above observation, the contact inhibition in transformed cells was also reduced, such as in wild-type CoAA-transfected cells but not in its AxxQ mutant-transfected cells (FIG. 10A). These data indicate that the overexpression of wild-type CoAA is sufficient for transformation in the soft agar assay, and the CoAA activation domain and EWS oncogenic domain are functional similar. Furthermore, the wild-type CoAA-transfected cells showed a higher proliferation rate than the control NIH3T3 cells as measured by BrdU incorporation assay (P=0.013), when 3-5 fold more CoAA protein above the endogenous level was detected by Western blotting (FIG. 10C-D). In addition, knockdown of CoAA with siRNA inhibited proliferation in a dose-dependent manner in the lung cancer cell line H69 that we previously identified with CoAA gene amplification (FIG. 7D). Collectively, these results support the conclusion that overexpression of CoAA promotes cell proliferation and induces transformation.

Example 14

Gene Amplification Leads to Stimulated CoAA Promoter Activity

Figure 11A:
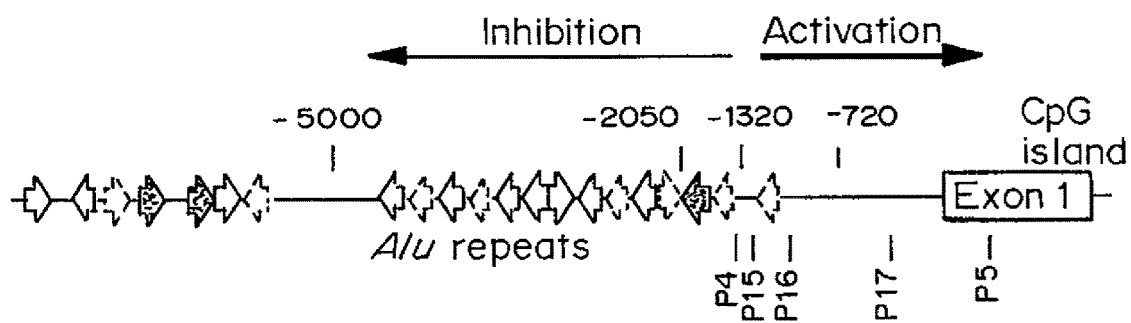
FIG. 11A is a schematic diagram of the regulatory region of the CoAA gene. Alu repeats are shown by orientated arrows. Numbers above the diagram indicate the promoter fragments used for reporter assays. A potential CpG island predicted by the NCBI is indicated.

Loss of sequences upstream of the CoAA gene reoccurred in three mapped amplicons. To understand the potential significance of this loss, the activities of these sequences were characterized in transcriptional regulation. The CoAA 5' region contains 21 tandemly arranged Alu repeats upstream of the basal promoter (FIG. 11A). The basal promoter, located immediately upstream of exon 1, is highly GC-rich and contains predicted transcription factor sites for NF-Y and Sp1 (not shown). Further semi-quantitative PCR analysis around the 5' boundaries of amplicons showed that Alu-rich sequences were invariably lost and the GC-rich basal promoter region co-amplified with the coding sequences. The PCR data indicated a significant unbalance of gene dosage between primers P15 and P16, within a region near the Alu-rich sequences (FIG. 11A). The PCR products at the upstream position (P15) were detectable by further nested PCR, indicating a lower gene copy number rather than a complete deletion of this DNA in primary tumors (not shown). In summary, the Alu-rich sequence, but not CoAA basal promoter, was lost from the amplicons.

Figure 11B:
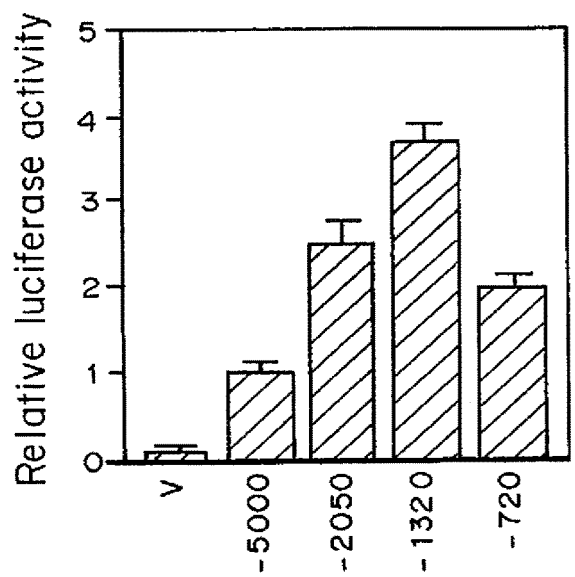
FIG. 11B is bar graph showing luciferase activity of the CoAA promoter. The length of the promoter fragments are from number as indicated to +1. The positions of these deletions are shown in FIG. 11A.
Figure 11C:
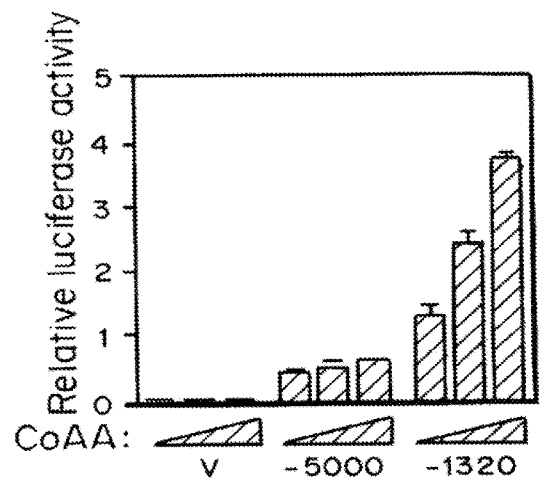
FIG. 11C is a bar graph of relative luciferase activity in cell having increasing amounts of CoAA expression plasmids (0, 0.2, 0.4 µg). Relative luciferase activities were measured and shown as means of triplicate transfections±standard errors.
Figure 11D:
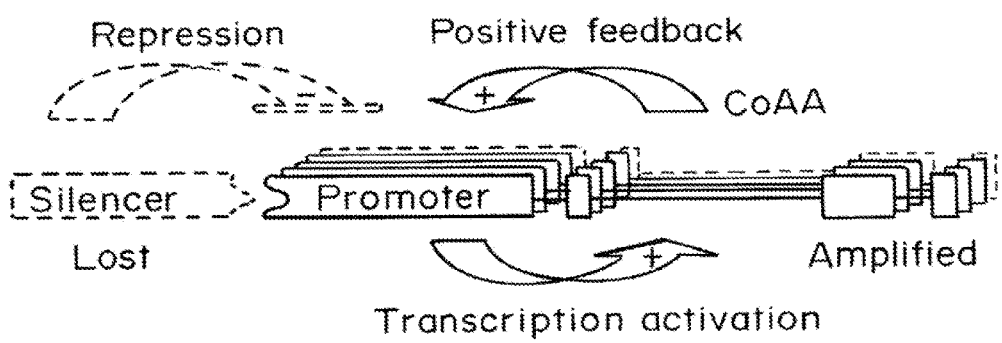
FIG. 11D is a diagram of CoAA activation in cancer. CoAA gene is activated through its basal promoter (in black) and inhibited by its upstream silencer (in grey). Overexpressed CoAA, produced by the amplified CoAA genes, stimulates its own promoter via a positive feedback loop. Loss of silencer leads to constitutive cycling of CoAA overexpression.
Figure 12A:
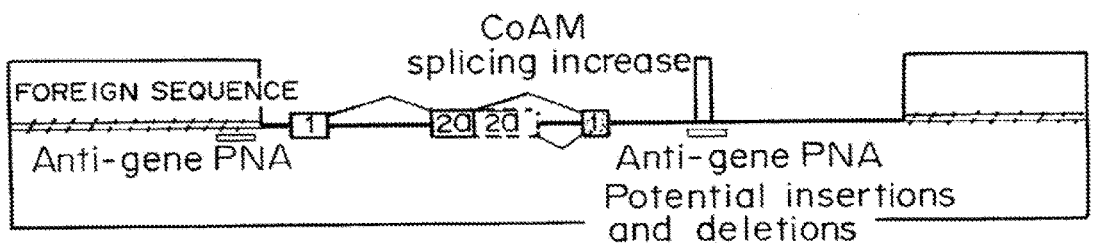
FIG. 12A is a diagram showing exemplary peptide nucleic acids designed to hybridize to specific genomic sequences of the CoAA gene.
Figure 12B:
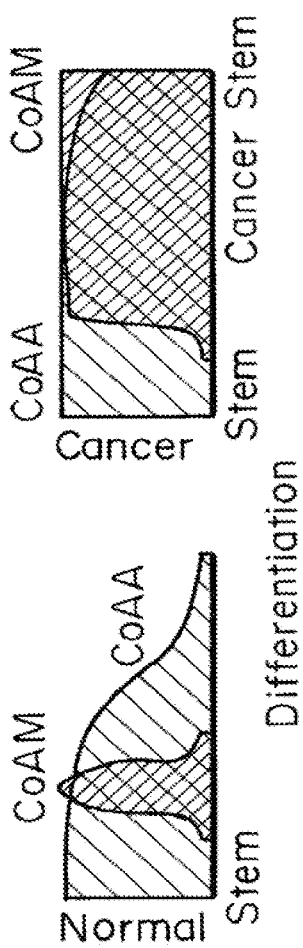
FIG. 12B provides exemplary peptide nucleic acid sequences that hybridize to mRNA encoding CoAA, CoAM, or both.
Figure 12B:
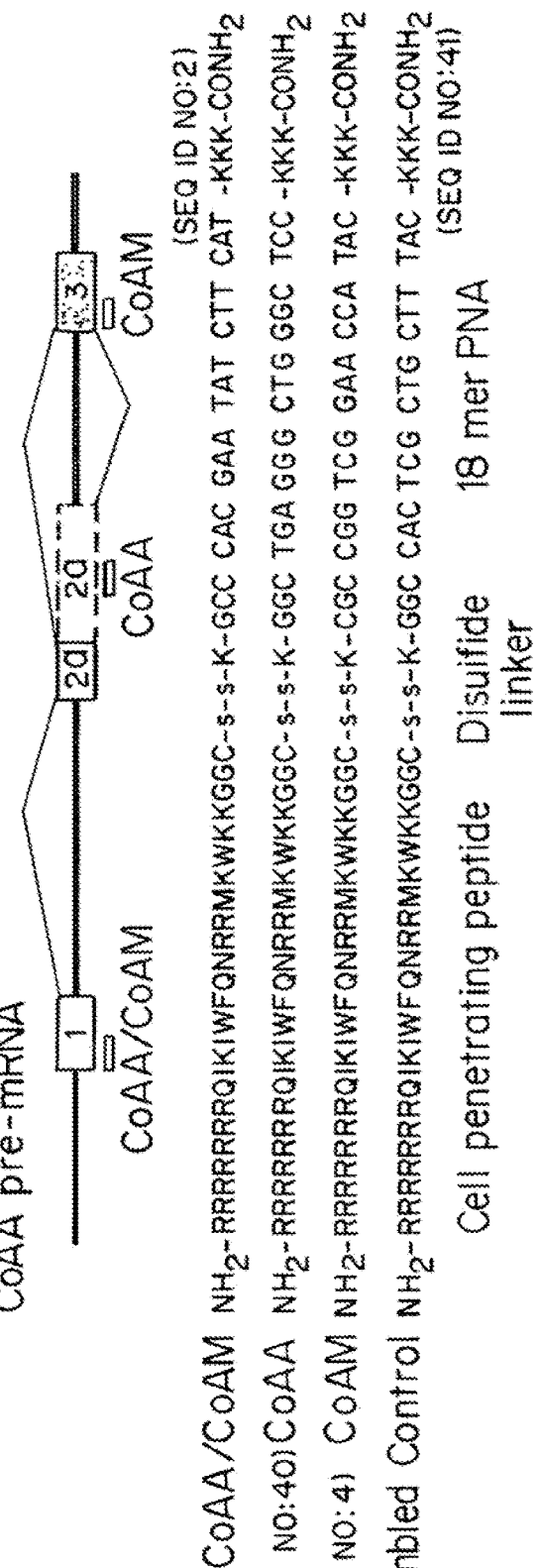

To evaluate the consequence of the sequence loss for transcriptional regulation, a serial deletion of CoAA upstream sequences was constructed. Each fragment was linked to a luciferase reporter. The results showed that the basal promoter region alone (−1320 to +1) has potent transcriptional activity while the inclusion of upstream Alu-rich sequences (−5000 to +1) drastically reduced the activity (FIG. 11B). The data confirm the positive regulatory role of the basal promoter and also suggest the presence of a silencing or negative regulatory element within the Alu-containing sequences (−5000 to −1320). Since CoAA is a potent transcriptional coactivator itself, we also examined if overexpression of CoAA protein would regulate its own regulatory sequences. The data indicated that CoAA significantly stimulated its own basal promoter activity in a dose-dependent manner (FIG. 11C). These data collectively point to a potential model for CoAA deregulation in cancer. As shown in FIG. 11D, the expression of the CoAA gene is normally activated through its basal promoter and inhibited by the upstream silencing sequences. This balance is disrupted in cancer when the CoAA gene is amplified together with its basal promoter but without its Alu-rich silencer. The overexpressed CoAA gene then further activates its own expression via a positive feedback loop. In the absence of the silencer, continued cycles of CoAA overexpression are established. The model provides a mechanistic explanation for the observed overexpression of CoAA in gene amplified tumors.

We claim:

1. A method for detecting or assisting in the diagnosis of cancer comprising:
   detecting the presence of one or more coactivator activator (CoAA) amplicons in a biological sample obtained from a subject, wherein the presence of one or more CoAA amplicons in the biological sample is indicative of cancer, and wherein the detection uses the nucleic acid sequence probe, RP11-527H7.

2. The method of claim 1, further comprising the step of detecting the presence of the CoAA amplicon by performing fluorescent in situ hybridization (FISH) analysis using the nucleic acid sequence probe, RP11-527H7.

3. The method of claim 1, further comprising the step of detecting the presence of the CoAA amplicon by performing quantitative polymerase chain reaction (qPCR) and polymerase chain reaction-based analyses using nucleic acid sequence primers comprising sequences of RP11-527H7.

4. The method of claim 1, wherein the biological sample is selected from the group consisting of blood, tissue, and cells.

5. A method of detecting or assisting in the diagnosis of cancer comprising: detecting the presence of one or more CoAA amplicons in a biological sample obtained from a subject, by performing fluorescent in situ hybridization (FISH) analysis using a diagnostic kit comprising the labeled nucleic acid sequence probe, RP11-527H7, wherein the presence of one or more CoAA amplicons in the biological sample is indicative of cancer.

* * * * *

SEQUENCE LISTING

<160> NUMBER OF SEQ ID NOS: 41

<210> SEQ ID NO 1
<211> LENGTH: 12900
<212> TYPE: DNA
<213> ORGANISM: Artificial Sequence
<220> FEATURE:
<223> OTHER INFORMATION: Synthetic peptide nuclei acid target

<400> SEQUENCE: 1

```
cgcggcaacc cccaggcgcg ggtttggaca gggcttccag aatgggagga gccctgactt      60
ccaattgtac aaagttttcc tgggagcccg ccggtcccag ccccacccgg gccagagacc     120
gccttacaga ctaggcctct ctgccgccgg cgccgctcgc gcgcgttctc ctctcttcag     180
ccctccctct tcttcccaac ccctctccc gccacgggct gtggcggttg gtcgtccctt      240
tcccaccccc tcagctaacg agcgggctct aggccctctg ggattggctg tgcctgagca     300
catcttccct cagcgtttct gattggtcgc tggacgcgcg ggatgcgagt ccccattggc     360
taggccaggg cgcctgcgcg gcggggttct cggtcgccag ccattcctga ggaggactgc     420
cggtcgttcg gacgtcttgc ctgtcgctgg aggagaggtc cgggctctcc aggaaggtgg     480
```

```
ctgcggcgac aaaatgaaga tattcgtggg caacgtcgac ggggcggata cgactccgga    540
ggagctggca gccctctttg cgccctacgg cacggtcatg agctgcgccg tcatgaaaca    600
gttcgccttc gtgcacatgc gcgagaacgc gggcgcgctg cgcgccatcg aagccctgca    660
cggccacgag ctgcggccgg ggcgcgcgct cgtggtggag atgtcgcgcc caaggcctct    720
taatacttgg aagattttcg tgggcaatgt gtcggctgca tgcacgagcc aggaactgcg    780
cagcctcttc gagcgccgcg gacgcgtcat cgagtgtgac gtggtgaaag gtaacgcgga    840
ggcgcgctcg ggggcggggg cgcgctcggg gcactctgcc tgttagccac gcccttacc    900 cggggtcgg tcactgcgcg gttgggaggg gtggggaagt gcgcgggagc aggtcggagg    960 tgttggggc gcgttgggta gagccaccct cctcccctgc ggtccaggaa ccgtccacca   1020
agtaggagga agcggctctg ggtggtgcg gcggccactg cgagccaagc tacggggccg   1080
gggacgcgcc tgagagcctt gcgagtgttc cggggcgcg ccttctcctg gtctcctggg   1140
cctggcaccc agcggaaatt gggaagtgac gggcacaagc cggatcatga agcggggaag   1200
atttctccac ttccccactt cctctccaga cgtcggtcag agcaagggaa gagggaaaag   1260 gtggggctg acgccccaag gccgccctcc tgttccctcc cgatgaatgt gctcaagcgg   1320
aaggtaacgg ggcccttgga cgtttctcgg gctgggtct tttagtcttg tctggcatgg   1380
gtctactcat gggcacagtt acacgtgggt acgagagggg cccttccga atcactttgg   1440 cctttcaata ttaggtaggt taggcgtggc agctctgtgc ttttctcctc cctcaaactt   1500 ggggttttc tttgggctcg attttacatc tgtcaactgg aaacccccagc cttttgcatg   1560 tgcaagaaag cttgttttat gaagtcccct tctgcgtagt cttttacatgc caagccagtg   1620 ccctagggca gtgtcattct tttataagct tggtgacttt gcagggggc atactctggc   1680 tgaggggtc ctggggaggg gtctgtgaga gctcttcatt aaacagtggc taaacacggt   1740
ttactgaatc agtagtagtc attgcttgag tagtctgatt ctcagggcag atcccggtgc   1800
cttttcttcg agaaaaatgt gtcaccataa tttaagcctg actagggacc cagttgactt   1860
tttcatagct tgagttttta tcccttaagc tctttatctt ttacattggc aagatttggt   1920
gggacagccg ttgtgtatgt ggccagtctc tgctccactt gggaacagat cagagttaac   1980
tttgccctgt cattttggaa gatgcagcct gggagtatct gatgccctac tcctggtggg   2040
ttcatacctg ctcataccct gtgtgagaag tttcagggat aggaaataaa tgtgggtgca   2100
agtgcttatt tatcccacca agatatttca tttgctgtcc tggaaaggca catgtttggg   2160
gccattccta gtcctttaag tgggggaaat ataagggtc atagtgtcca ctactaggaa   2220
caagtccttg ttctgcatta atactgcatt ctattttcct caactcaggt tatacaagtc   2280
cacgactatc cggaatcggg cttttcctgct gggtgctctg aggcaggctg tatggtgcat   2340 ggattttgc ttttgtttag agtaaaagag tggtgggga gggtctcaga ttgggtactt   2400
gtccagcaaa agggtgggt atatgagtct catttgtgag agttttgtgt ttaattgact   2460
taccaagttt cttttgtggt tgttaggtag agtggctact aggttgagag tctagagtca   2520
aacatctgaa gggacagtct ccctggaact caggcttctt gctggctttc aggtggtaga   2580
gaaagtcaaa aatttgcctg aaatttgctt gggacccaac accaagtgac gatgcgggtg   2640
aagtgcataa ctgcacatga attttagaa ctcctggctg actccttgtg agagttagac   2700
ggagttttgt gcatcttgtt cctttgtaaa catttgatta gcaaaaatgc attgacttac   2760
tccgggagtg gtggtcaact atttgcagtt acattgttgt gtaacagagc tcctgacata   2820
cttcgatgta agagactggg aaagatttga acatcatatc ctccactgat gtcttttat   2880
```

```
ctgtttgtga tgacggaaag tgagggttga agttgggag tgtagtagaa gcgactggct    2940
ctctaaagag cgtactcatt tcttatgctg ggaatggtca tttgattgag tctccttgtg    3000
ttggctgaca gggctttgaa aagcacagaa gcttggtgtt gcaccagaca accagctctg    3060
ttttatttca caggaaaaaa aaacaacata gttgcttggt tactccagga gcttagatag    3120
gatttgtaga acagaaatct caatagcaac agtggattgt aaccactcca cagcttcctc    3180
ctattgggtg ttcaaagatg aacagcttcc ggaaacatgt acagacttgt ggggagatct    3240
gaaagacaaa agaggaaaat atcttctctt cattttgtg agtgactgtt tcttcttcct    3300
atacagagct ctgtagtttc aagtttaaga ttttttcttt ttcttttttt tttttttag    3360 acggagtctg ctctgtcgc ccaggctgga gtgcactggc gccatctcgg ctcactgcaa    3420
gctccgcctc ctgggttcac gccattctcc tgcctcagcc tcccgagtag ctgggactac    3480
aggcgcccgc caccacaccc agctaatttt ttgtattttt agtagagacg gggtttcact    3540
gtgttagcca ggatggtctc gatctcctga ccttgtgatc cgcctgcctc agcctcccaa    3600
agtgctggga ttacaggcgc aagccaccgc gcctagccct caagtttaag attttagtc    3660 ttaagatagg agaacttgtt tttctggatt cacttaactt tgttactgga ggacttgtga    3720
tgccaccaga ccatttggag atctctgtaa acattactt gatagtccca atgcagtgat    3780
ttccttcaga gtttccttga attagatctg tgggcaagaa ggttcctgga attttcaga    3840 tctctggttt taatggtctt aggagtactt gggtgttagg gcatctttaa tctagctagg    3900
tctgtgcttt gcacttactg tgatgggct tatcactaca ggatgcagtt gagttagctg    3960
ggcaacctat tcacactttt cccctccagt gtcaggctta gaaacttcct gatacaattt    4020
ggttataatt gtatcagatg gattttaaa ttttgtattt attttatgt tatttatata    4080 tttattattt ttttttatga gacagagtct cattctgttg cccaggctgg agtgcagtgg    4140
tgagatcttg gctcactgca acctccgtct cctgggttca gcaattctc tgcctcagc    4200 ctctcaagta gctgggtcta caggccacca cacctggcta attttttgaat ttttagtaga    4260 gacagggttt cactatgttg gccaggctgg tcttgaactc ctgacctcag gtgatcttcc    4320
tgcctcggcc tcccaaagtg ttgggattac aggtgtgagc caccatgccc ggcttggatt    4380
tttaaatttt ttgatcagtt ataaaactca tttgggtagt catttgaatc atacatgtga    4440
aatctcaatt ttcagatttc accacttggt ctgaataaaa ctcactaagg agggaaacag    4500
acagtgggat gtccaaatgc tcttgtaagc ccatggaagt ttttgtctca ttctagtgtc    4560
aggaagttgt ggatagaata atcaggactg ttagaattgt tccttaatat tccctcagaa    4620
tgtctggagg cccctcctg caacaagtgc ctatgagctc cagcaactct gcttcccctt    4680
cactttgggc ctttctgctt gccatctcca ggtggttttg ctattcccga ggattacctc    4740
agcctctggt tttatttta tttttatt aaagattttt taaaatattt attcattctt    4800
tagggtctcg ctttgttgct caggccagag tgcagtggcg tgattgtggc tcactgtagt    4860
cttgacctcc tgagctcaag ccatccttcc acctcagtct cccaaagtat taggattaca    4920
ggagggagcc accattcctg gcccagcctc tgctttaaa gggctcttag gccacatgct    4980
ggttttttgt gttttttttt taagcttact ctattcaaag tggagatgaa ggatcacagg    5040
acaactttag tgccttatgc ctaggccaaa ggaaacacgt agcttttcac aggtggtaga    5100
taaggctctg gccatgggag tgttgaggac agagttgtga taattcattt tgttctttt    5160 ttttttgag agggagtttc atccttttg cccaggctgg agtacagtgg cacgatcttg    5220
```

```
gctcactgca acctccgcct cccgggttaa agtgattctc ctgcctcggc ttcttgagta      5280
gctgggatta caggcacatg ccaccacagc cggctaattt aatatttta gtaaagacgg       5340 cgtttcacct tgttggtcag gctggtcttg aactcctgac ctcaggtggt ccgcctgcct      5400
cggcctcccc aaagtgctgg gattatggtg tgagtcattg cgcctggtct cattgtgttc      5460
ttttatcgtc tgtgccagct tctaagtttg catggcattg tgttttgctt gagatgaaag      5520
ataatattct atagggaaat aaatctctgg ttatttctag gtttgaataa tcataattcc      5580
ttattctgta gctgttcata tcttacaagg cacttttgtc ttttctcttg aacctcttaa      5640
ctttgaggta ggtaggatag atgtgtcgga ggaaatacat ggtaagtttc tttttatttt      5700
ttttgagacg gagttttgcg cttgtcaccc aggctggagt gcagtgatct tggctcactg      5760
cagcctcctt cttttcttc cgggttcaag tgattctcct ccctcagcct ctggagtagc       5820
tgggattaca ggtgccagcc accacgccct ggtaatttt gtattttag tagagacgtg        5880 gtttcaccat gttggccagg ctggtctgga attcctgacc tcaggtgatc cacccacctg      5940
ggcttcctaa agtgttggga ttacatgcgt gagccaccgt gcttggctag tttcttttct      6000
ttttttcttt ttttttttt ttgaaatgga gtcttgctgt gtcacccaga ctggagtacg       6060
gtggtgccat ttcggctcac tgcaacttcc acctcccagg ttcaagtgat tctcctgccc      6120
cagagcctcc tgagtagctg gaattatagg tgtgcaccac cacacctagc taattttgt       6180 atttttagta gagacagggt ttcaccatgt tggtcaggct gatcttgaac tcctgatctc      6240
aggtgatctg cctgccttgg cctcccaaag ccctggcatg agccctgta cctgcctaaa       6300 tggtaagttt cctaagatct tataacaagt cagtgatacc tgggtctgga actgagacca     6360
ttgaatttct aattaaggat cccttttgtg ctatgccaca cttctgactt ctacttattg      6420
attgcatttt ttccccatta tccttagtct tgtgtcattg tcttcaaatc cagggaaatg      6480
acttgttctg taggagcagc tagataaggc atcccagtac gaaagtttct aaaaatgagg     6540
acccttgttt ggaggttatt aagaatgttt cttatcttag tattgtcatc tgggtagctc     6600
tttgtttctt aagctgatgt gacagatagc atcctggtac ttggatgcta tctaagagta    6660
gccacaggtc gagaatggag ctaagcttag agccttattt cctaggggca ggattctctc     6720
cttcagattc tgcctgtgct ttgtgagtgt ggacatgaga atttctttcc attccttcat     6780
tccctgaagt tttctccttc tgtgtagtag ataagtatag ctttgagacc ggcatcctgt     6840
cttctcctac cacagcttat tcaggtcata atgagagctg caggggtaac ctggttagca    6900
gagcctgtta gctgcagtaa ttgcagcttc ataccttata ggtgagaaac cagatctttc     6960
tggtaagcag tctgctctgt gaacagaagc ccaaggtgta aggtatacct ctgtccctta     7020
aagaggaaac agtggaggat gcagtgtggt ctgggacagg gggattgggc atgaactcag     7080
ccagtgggct tagtttctat tcccatacct cattggctta cacagggtcc atcttctctg    7140
cttctaagcc taaattttta gtcatattac acagtcctgc cttataccttt gacttctcag    7200 ggatagatta tgtagcaaag gggcattgga agagctgtga ttctggtcct gactctaaca     7260
cactttgagt ggggcaagcc atataaaaac tcttgagcat gtatgtccac ctgttaaatg     7320
gaggtaatga ttcttcttgccc tgcctacctc acaggattgt gaggcccaaa tgaggtcctc  7380
ctgtacctaa gagtgctttg aaaacttggg aagtactgtg aaaagcggga gagatcatat     7440
tggaatgttg tgaactgctt gcttgttgca gtctatctct cttgccttaa ttggacatgg     7500
gctgagagat gggtcatacc aaaacgtgag tggtcatttc cagtgtttga gagttaggcc     7560
tcaaaagtga gctaggcctc aaaggtgttt ggtgagtttg ggttgagaac actgaagaac      7620
```

```
tgagtgatct aggaacgctt tctgcatttt gttctgctgg tttgtactta caggagatgt   7680
gaagattttt atcctgtgtt gcagttcatc tttgctcctt cttctctcac caggaagttg   7740
ggtgagatgg cagggtttgt aaaggggaga atgggaagaa ggctgtaggc aaagatgact   7800
gcttgggaca gtcagaagct tgttatatg ggagctacat tttatgacat actcctggag    7860
aggagggttt ggaggccttg gaggtagctg caacagctg ggtgctgttg tgtgtccaat    7920
ttgggaccca tcaggtagca tgccctgccc ccctaattgc taaccctctg tctgctgctt   7980
tatcagacta cgcgtttgtt cacatggaga aggaagcaga tgccaaagcc gcaatcgcgc   8040
agctcaacgg caaagaagtg aagggcaagc gcatcaacgt ggaactctcc accaagggtc   8100
agaagaaggg gcctggcctg gctgtccagt ctggggacaa gaccaagaaa ccaggggctg   8160
gggatacggc cttccctgga actggtggct tctctgccac cttcgactac cagcaggctt   8220
ttggcaacag cactggtggc tttgatgggc aagcccgtca gcccacacca cccttctttg   8280
gtcgcgaccg cagccctctg cgccgttcac ctccccgagc ctcttatgtg gctcctctga   8340
cggcccagcc agctacctac cgggcccagc cgtccgtgtc actgggagct gcctacaggg   8400
cccagccttc tgcctctttg ggtgttggct atcggactca gcccatgaca gcccaggcag   8460
cctcttaccg cgctcagccc tctgtctccc ttggggcacc atacaggggc cagctggcta   8520
gtcctagctc ccagtctgct gcagcttctt cactcggccc atatggtgga gcccagccct   8580
cagcctcggc cctttcctcc tatggggtc aggcagctgc agcttcttcg ctcaactcct    8640
atggggctca gggttcctcc cttgcctcct atggtaacca gccatcctct tacgcgcccc   8700
aggctgcctc ttcctatggg gttcgtgcag ctgcttcttc ctacaacacc cagggagcag   8760
cttcctcctt aggctcctac ggggctcagg cagcctccta tggggcccag tctgcagcct   8820
cctcactagc ttatggagcc caggcagctt catataatgc ccagccctcg gcctcttaca   8880
atgcccagtc tgccccatat gctgcacagc aggctgcttc ctactcttcc caacctgctg   8940
cctatgtggc acagccagcc acagctgctg cctatgccag ccagccagca gcctacgccg   9000
cacaagccac taccccaatg gctggctcct atggggccca gccggttgtg cagacccagc   9060
tgaatagtta cggggcccaa gcatcaatgg gcctttcagg ctcctatggg gctcagtcgg   9120
ctgctgcggc cactggctcc tatggtgccg cagcagccta cggggcccaa ccttctgcca   9180
ccctggcagc tccttaccgc actcagtcat cagcctcatt ggctgcttcc tatgctgccc   9240
agcagcatcc ccaggctgct gcctcctacc gcggccagcc aggcaatgcc tacgatgggg   9300
caggtcagcc gtctgcagcc tacctgtcca tgtcccaggg ggccgttgcc aacgccaaca   9360
gcaccccgcc gccctatgag cgtacccgcc tctccccacc ccgggccagc tacgacgatc   9420
cctacaaaaa ggctgtcgcc atgtcgaaaa ggtactgtat gccccccgc ctctgccccc    9480 agctggggct tagggcaagg ggctgaggtt ggcatgggag ggaaactgga ggcatcggcc   9540
cctccctcgg tcttctcttc tctattttg tgggatgtcc agaggccgag gggagcagtg    9600
tctatgaact ttcctggtca ccagggttca ggtggagcat agtgctcagc ctgggtggt    9660 acctgctagt caggccaggc acagtgtcac ctgtctaggc tagcccaagt gtcattggag   9720
ctactgcctg caggactgtg gcccatatcc tttcccactg tctcaaggat ccttaagcct   9780
attacgtggt tgtcctggct ttggcaggga tgtgggttaa agagtagtcc ctttggcatt   9840
cactggctaa aggcaagttt acgaggtgcg tccactctgg gaagttgggg acctcgcttt   9900
catccgccgt tctgttgata aacaaccaag gtctttctct gcagggccca ggggcggaga   9960
```

```
tagtttgctg tggtgtggga atgtagacca aaatccacct tggctagttc agaggggagg   10020
acttcagtgg agggtttgat ttcccactga gttgaagcca ggcttgattt ttttggcctg   10080
gataggtga tgagccttct gacaaaagga gaccaatctc ttggagacca ctgtgatcac    10140
accctccctg tccccattgg catctcccca atgcccacct ggagtcctcc cctcaattgt   10200
ctcattcacc aactgtcttc ttctctcgac taggtatggt tccgaccggc gtttagccga   10260
gctctctgat taccgccgtt tatcagagtc gcagctttcg ttccgccgct cgccgacaaa   10320
gtcctcgctg gattaccgtc gcctgcccga tgcccattcc gattacgcac gctattcggg   10380
ctcctataat gattacctgc gggcggctca gatgcactct ggctaccagc gccgcatgta   10440
gggccatcct gggatggggc accacaggga gggagggaga aaagaggtgg gtagggttac   10500
agatccaggt tataactact ctggcccata cctttcctgg ttgtggtttt tcatgccctc   10560
taccatgtgg gccttcccca ggagatgatc ctgttaagtg ttcggcagta acctactttg   10620
ttccttcgcc tcagcagcaa atcttgctac tggctctaga tctgcggttt cccctctacc   10680
ctgcctcccg tctcccaga atgggaattt cttttatgtt tttattttt tcctggctcc      10740
cttttatttt tgtgcgcgat atttaaggtc gtctggatgg ggaagcaacc tgcagctgag   10800
gtcgccggcg ccttttcctt tttagatggg aaggaggcca ggaaagggtc agcttaacca   10860
tttcctatgt gccaagctgt gccagcagtc cagggtaccc tgactgtccc tctgtagact   10920
gttgagactg agttcctgtt gggacagtca gttggtatgt atccaagtcc ctgctgacca   10980
ctaatgttct agctgatggt gagcggcaca gtcccacttc cccatctccc caagtaggtg   11040
gtgttagaaa accttaattt tttttccctt ttgtatggac tacaaataaa acttgggca    11100
atttgcagtt tggaaacctg gttgtcattg tcttgattgc attcagtgtc aaaggagcca   11160
atttgacatc caggaagaca tgatagctaa agggaaggca gtcagagaac ccaggactgg   11220
tgaggaaagg ggtttgaatg tcggaattag aaggattgcc ctgtggccca aaggattta    11280
gctcatcgtc gtcctgctag cctgccatct ttcagacttt ccagggcagg tggcctggtc   11340
ctcagccctc aacttgagtt agtcacacca aaatgcagta aatgatgccc atttttcctct  11400
gcctgtgctt gaccattttc actgactttt ctccagttca ggaataacct gtgttccaat   11460
gggatggttc tgggggtttgg cctcttagga agtgggaat gggctgctgt ggtatttaca   11520
ggctagtaga tccttaggc agtaggctgg aatgagtgct ggggctggga cccgaaaagg    11580
aaccagtagt ggagtgggg taatggcgtt gcctgatact gccctatggt tggaataagg    11640
aagggcagag aaaacttgaa gcaggtatgg ggcattctgg ccatagagct cgtatttgc    11700
ctgttgagct gtaccatgga gcatcctcct gtgtcctgcc aaccctgcc attatagtca    11760
ccggagactc ctttacctat ccctatctgt tagggttttc agatgtcctc tcgctgggtt   11820
tatatttgaa ggtatagaat ctgggaaagg gtggggtgca agctaaccaa ataggatgc    11880
tagggttggg tggggaattg aggactcttc tgtgcttta ttgtagggct ggggatcgag    11940
gatctgggca aaaatatga catttccaac caggacaaa atgaggctt gggcttagtg      12000
atgggtaaat ggaagactgg ttgagtggga tgataatggg agaacttact gatgctcttt   12060
tgggaaaagg tgctttaaag actcgatttg ggagcctact ggggcaaggc gactggggag   12120
gtgtacgtgt tagtcaagtg gaggtcaggt gggttatctt ctgcctcctt cactggcttc   12180
atgtgaactt gcctgtgaca gaatatcttc cctagatgt cctcttccct cttgccatcg    12240
tgcaaaagca ttcgatctta tgaccgtgag ttccttatttg tggatgctaa ctgggtaat   12300
ctcagggagt actggggcca tggctctttc ccttgcttct ctttctgctc actgcttgc    12360
```

-continued

```
tttcaggtgc ttagctgctc cttttttattt ctttgcagga ctgggaaagc atgggaggag   12420
gattttgata agtttcttgt tctctgcgtg gtgatggggt ggtctgaggg ccaagttaat   12480
aagcctacct ttggttatta ccctggaaaa ttgagggttg atggtagggt tatgattgtg   12540
gcctgtgtat ttgcaatttt tctttgtcag tgtggctttc tgtcatcttc cttttctcc    12600
agtgagggtt ctgccactgt ctcaatccct tggttcctgc aaaaaacagc taaatgtgct   12660
ctcagggcca gtggtgatgt tctgtgttgc agccccagct cttgaaagtg acctggccca   12720
gatgagctct gcctgcttgt catctttagg tcctgctgcc cctgctgcct cagccctcag   12780
gctcctaact gctcaagcca gaaggagcta caaagccaaa tcatttgtca tttttctctg   12840
gcagattgtt ttaaaatctc cctcccctct tttattttaa ttatgccacc tgtgttaatc   12900
```

<210> SEQ ID NO 2
<211> LENGTH: 18
<212> TYPE: DNA
<213> ORGANISM: Artificial Sequence
<220> FEATURE:
<223> OTHER INFORMATION: Synthetic peptide nucleic acid
<220> FEATURE:
<221> NAME/KEY: misc_feature
<222> LOCATION: (1)..(1)
<223> OTHER INFORMATION: Linked to cell penetrating peptide
      RRRRRRRQIKIWFQNRRMKWKKGGC-s-s-K
<220> FEATURE:
<221> NAME/KEY: misc_feature
<222> LOCATION: (1)..(18)
<223> OTHER INFORMATION: deoxyribose backbone replaced with a backbone
      having peptide linkages
<220> FEATURE:
<221> NAME/KEY: misc_feature
<222> LOCATION: (18)..(18)
<223> OTHER INFORMATION: Linked to peptide sequence KKK-CONH2

<400> SEQUENCE: 2
gcccacgaat atcttcat                                                  18

<210> SEQ ID NO 3
<211> LENGTH: 2781
<212> TYPE: DNA
<213> ORGANISM: Artificial Sequence
<220> FEATURE:
<223> OTHER INFORMATION: Synthetic Antisense Hybridization target

<400> SEQUENCE: 3

```
agccattcct gaggaggact gccggtcgtt cggacgtctt gcctgtcgct ggaggagagg     60
tccgggctct ccaggaaggt ggctgcggcg acaaaatgaa gatattcgtg ggcaacgtcg    120
acggggcgga tacgactccg gaggagctgg cagccctctt tgcgccctac ggcacggtca    180
tgagctgcgc cgtcatgaaa cagttcgcct tcgtgcacat gcgcgagaac gcgggcgcgc    240
tgcgcgccat cgaagccctg cacggccacg agctgcggcc ggggcgcgcg ctcgtggtgg    300
agatgtcgcg cccaaggcct cttaatactt ggaagatttt cgtgggcaat gtgtcggctg    360
catgcacgag ccaggaactg cgcagcctct tcgagcgccg cggacgcgtc atcgagtgtg    420
acgtggtgaa agactacgcg tttgttcaca tggagaagga agcagatgcc aaagccgcaa    480
tcgcgcagct caacggcaaa gaagtgaagg gcaagcgcat caacgtggaa ctctccacca    540
agggtcagaa gaaggggcct ggcctggctg tccagtctgg ggacaagacc aagaaaccag    600
gggctgggga tacggccttc cctgaactg gtggcttctc tgccaccttc gactaccagc    660
aggcttttgg caacagcact ggtggctttg atgggcaagc ccgtcagccc acaccaccct    720
```

```
tctttggtcg cgaccgcagc cctctgcgcc gttcacctcc ccgagcctct tatgtggctc    780
ctctgacggc ccagccagct acctaccggg cccagccgtc cgtgtcactg ggagctgcct    840
acagggccca gccttctgcc tctttgggtg ttggctatcg gactcagccc atgacagccc    900
aggcagcctc ttaccgcgct cagccctctg tctcccttgg ggcaccatac aggggccagc    960
tggctagtcc tagctcccag tctgctgcag cttcttcact cggcccatat ggtggagccc   1020
agccctcagc ctcggccctt tcctcctatg ggggtcaggc agctgcagct tcttcgctca   1080
actcctatgg ggctcagggt tcctcccttg cctcctatgg taaccagcca tcctcttacg   1140
gcgcccaggc tgcctcttcc tatggggttc gtgcagctgc ttcttcctac aacacccagg   1200
gagcagcttc ctccttaggc tcctacgggg ctcaggcagc ctcctatggg cccagtctg    1260
cagcctcctc actagcttat ggagcccagg cagcttcata taatgcccag ccctcggcct   1320
cttacaatgc ccagtctgcc ccatatgctg cacagcaggt tgcttcctac tcttcccaac   1380
ctgctgccta tgtggcacag ccagccacag ctgctgccta tgccagccag ccagcagcct   1440
acgccgcaca agccactacc ccaatggctg gctcctatgg ggcccagccg ttgtgcaga    1500
cccagctgaa tagttacggg gcccaagcat caatgggcct ttcaggctcc tatgggcc    1560
agtcggctgc tgcggccact ggctcctatg gtgccgcagc agcctacggg gcccaacctt   1620
ctgccaccct ggcagctcct taccgcactc agtcatcagc ctcattggct gcttcctatg   1680
ctgcccagca gcatcccag gctgctgcct cctaccgcgg ccagccaggc aatgcctacg   1740
atggggcagg tcagccgtct gcagcctacc tgaccatgtc ccaggggcc gttgccaacg   1800
ccaacagcac cccgccgccc tatgagcgta cccgcctctc cccaccccgg ccagctacg    1860
acgatcccta caaaaaggct gtcgccatgt cgaaaggta tggttccgac cggcgtttag    1920
ccgagctctc tgattaccgc cgtttatcag agtcgcagct ttcgttccgc cgctcgccga   1980
caaagtcctc gctggattac cgtcgcctgc ccgatgccca ttccgattac gcacgctatt   2040
cgggctccta taatgattac ctgcgggcgg ctcagatgca ctctggctac cagccgcca   2100
tgtagggcca tcctgggatg gggcaccaca gggagggagg gagaaaagag gtgggtaggg   2160
ttacagatcc aggttataac tactctggcc catacctttc ctggttgtgg tttttcatgc   2220
cctctaccat gtgggccttc cccaggagat gatcctgtta agtgttcggc agtaacctac   2280
tttgttcctt cgcctcagca gcaaatcttg ctactggctc tagatctgcg gttttccctc   2340
tacctgcct cccgtctccc cagaatggga atttcttta tgttttatt tttttcctgg     2400
ctcccttta ttttgtgcg cgatatttaa ggtcgtctgg atgggaagc aacctgcagc     2460
tgaggtcgcc ggcgccttt tcttttaga tgggaaggag gccaggaaag ggtcagctta    2520
accattcct atgtgccaag ctgtgccagc agtccaggt accctgactg tccctctgta    2580
gactgttgag actgagttcc tgttgggaca gtcagttggt atgtatccaa gtccctgctg   2640
accactaatg ttctagctga tgtgagcgg cacagtccca cttcccatc tccccaagta    2700
ggtggtgtta gaaaaccta attttttttc ccttttgtat ggactacaaa taaaacttgg   2760
ggcaatttgc agtttggaaa a                                           2781
```

<210> SEQ ID NO 4
<211> LENGTH: 18
<212> TYPE: DNA
<213> ORGANISM: Artificial Sequence
<220> FEATURE:
<223> OTHER INFORMATION: Synthetic Peptide nucleic acid
<220> FEATURE:
<221> NAME/KEY: misc_feature

```
<222> LOCATION: (1)..(1)
<223> OTHER INFORMATION: Linked to penetrating peptide sequence
      NH2-RRRRRRRQIKIWFQNRRMKWKKGGC-s-s-K
<220> FEATURE:
<221> NAME/KEY: misc_feature
<222> LOCATION: (1)..(18)
<223> OTHER INFORMATION: deoxyribose backbone replaced with a backbone
      having peptide linkages
<220> FEATURE:
<221> NAME/KEY: misc_feature
<222> LOCATION: (18)..(18)
<223> OTHER INFORMATION: Linked peptide sequence KKK-CONH2

<400> SEQUENCE: 4
cgccggtcgg aaccatac                                                 18

<210> SEQ ID NO 5
<211> LENGTH: 6
<212> TYPE: PRT
<213> ORGANISM: Artificial Sequence
<220> FEATURE:
<223> OTHER INFORMATION: Synthetic CoAM epitope

<400> SEQUENCE: 5

Met Val Pro Thr Gly Val
1               5

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
atgaagatat tcgtgggcaa                                               20

<210> SEQ ID NO 7
<211> LENGTH: 19
<212> TYPE: PRT
<213> ORGANISM: Artificial Sequence
<220> FEATURE:
<223> OTHER INFORMATION: Synthetic primer

<400> SEQUENCE: 7

Cys Thr Ala Ala Ala Cys Gly Cys Cys Gly Gly Thr Cys Gly Gly Ala
1               5                   10                  15

Ala Cys Cys

<210> SEQ ID NO 8
<211> LENGTH: 20
<212> TYPE: PRT
<213> ORGANISM: Artificial Sequence
<220> FEATURE:
<223> OTHER INFORMATION: Synthetic CoAM-specific primer

<400> SEQUENCE: 8

Thr Cys Thr Cys Cys Ala Cys Cys Ala Ala Gly Gly Gly Thr Ala Thr
1               5                   10                  15

Gly Gly Thr Thr
            20

<210> SEQ ID NO 9
<211> LENGTH: 18
<212> TYPE: PRT
<213> ORGANISM: Artificial Sequence
<220> FEATURE:
```

<223> OTHER INFORMATION: Syntetic CoAM-specific primer

<400> SEQUENCE: 9

Cys Thr Ala Cys Ala Thr Gly Cys Gly Gly Cys Gly Cys Thr Gly Gly
1               5                   10                  15

Thr Ala

<210> SEQ ID NO 10
<211> LENGTH: 24
<212> TYPE: DNA
<213> ORGANISM: Artificial Sequence
<220> FEATURE:
<223> OTHER INFORMATION: Synthetic Nanog primer

<400> SEQUENCE: 10
agggtctgct actgagatgc tctg                                          24

<210> SEQ ID NO 11
<211> LENGTH: 24
<212> TYPE: DNA
<213> ORGANISM: Artificial Sequence
<220> FEATURE:
<223> OTHER INFORMATION: Synthetic Nanog primer

<400> SEQUENCE: 11
caaccactgg tttttctgcc accg                                          24

<210> SEQ ID NO 12
<211> LENGTH: 24
<212> TYPE: DNA
<213> ORGANISM: Artificial Sequence
<220> FEATURE:
<223> OTHER INFORMATION: Synthetic Oct4 primer

<400> SEQUENCE: 12
ctgagggcca ggcaggagca cgag                                          24

<210> SEQ ID NO 13
<211> LENGTH: 24
<212> TYPE: DNA
<213> ORGANISM: Artificial Sequence
<220> FEATURE:
<223> OTHER INFORMATION: Synthetic Oct4 primer

<400> SEQUENCE: 13
ctgtagggag ggcttcgggc actt                                          24

<210> SEQ ID NO 14
<211> LENGTH: 23
<212> TYPE: PRT
<213> ORGANISM: Artificial Sequence
<220> FEATURE:
<223> OTHER INFORMATION: Synthetic Sox6 primer

<400> SEQUENCE: 14

Cys Ala Gly Cys Gly Gly Ala Thr Gly Gly Ala Gly Ala Gly Gly Ala
1               5                   10                  15

Ala Gly Cys Ala Ala Thr Gly
            20

<210> SEQ ID NO 15
<211> LENGTH: 24
<212> TYPE: DNA
<213> ORGANISM: Artificial Sequence
<220> FEATURE:

<223> OTHER INFORMATION: Synthetic Sox6 primer

<400> SEQUENCE: 15 cttttctgt tcatcatggg ctgc                                        24

<210> SEQ ID NO 16
<211> LENGTH: 22
<212> TYPE: DNA
<213> ORGANISM: Artificial Sequence
<220> FEATURE:
<223> OTHER INFORMATION: Synthetic MAP2 primer

<400> SEQUENCE: 16
ggacatcagc ctcactcaca ga                                         22

<210> SEQ ID NO 17
<211> LENGTH: 23
<212> TYPE: DNA
<213> ORGANISM: Artificial Sequence
<220> FEATURE:
<223> OTHER INFORMATION: Synthetic MAP2 primer

<400> SEQUENCE: 17
gcagcatgtt caaagtcttc acc                                        23

<210> SEQ ID NO 18
<211> LENGTH: 22
<212> TYPE: DNA
<213> ORGANISM: Artificial Sequence
<220> FEATURE:
<223> OTHER INFORMATION: Synthetic GAFP primer

<400> SEQUENCE: 18
gaatgactcc tccactccct gc                                         22

<210> SEQ ID NO 19
<211> LENGTH: 21
<212> TYPE: DNA
<213> ORGANISM: Artificial Sequence
<220> FEATURE:
<223> OTHER INFORMATION: Synthetic GFAP primer

<400> SEQUENCE: 19
cgctgtgagg tctggcttgg c                                          21

<210> SEQ ID NO 20
<211> LENGTH: 20
<212> TYPE: DNA
<213> ORGANISM: Artificial Sequence
<220> FEATURE:
<223> OTHER INFORMATION: Synthetic GAPDH primer

<400> SEQUENCE: 20
accacagtcc atgccatcac                                            20

<210> SEQ ID NO 21
<211> LENGTH: 20
<212> TYPE: DNA
<213> ORGANISM: Artificial Sequence
<220> FEATURE:
<223> OTHER INFORMATION: Synthetic GAPDH primer

<400> SEQUENCE: 21
tccaccaccc tgttgctgta                                            20

```
<210> SEQ ID NO 22
<211> LENGTH: 18
<212> TYPE: DNA
<213> ORGANISM: Artificial Sequence
<220> FEATURE:
<223> OTHER INFORMATION: Synthetic primer

<400> SEQUENCE: 22
aatgtgtcgg ctgcatgc                                                 18

<210> SEQ ID NO 23
<211> LENGTH: 19
<212> TYPE: DNA
<213> ORGANISM: Artificial Sequence
<220> FEATURE:
<223> OTHER INFORMATION: Synthetic primer

<400> SEQUENCE: 23
ctaaacgccg gtcggaacc                                                19

<210> SEQ ID NO 24
<211> LENGTH: 24
<212> TYPE: DNA
<213> ORGANISM: Artificial Sequence
<220> FEATURE:
<223> OTHER INFORMATION: Synthetic primer

<400> SEQUENCE: 24
tatgaagaga tacgccctgg ttcc                                          24

<210> SEQ ID NO 25
<211> LENGTH: 22
<212> TYPE: DNA
<213> ORGANISM: Artificial Sequence
<220> FEATURE:
<223> OTHER INFORMATION: Synthetic primer

<400> SEQUENCE: 25
atggctggca actagaaggc ac                                            22

<210> SEQ ID NO 26
<211> LENGTH: 20
<212> TYPE: DNA
<213> ORGANISM: Artificial Sequence
<220> FEATURE:
<223> OTHER INFORMATION: Synthetic primer

<400> SEQUENCE: 26
tctccaccaa gggtatggtt                                               20

<210> SEQ ID NO 27
<211> LENGTH: 19
<212> TYPE: DNA
<213> ORGANISM: Artificial Sequence
<220> FEATURE:
<223> OTHER INFORMATION: Synthetic primer

<400> SEQUENCE: 27
gcctggctgg ccgcggtag                                                19

<210> SEQ ID NO 28
<211> LENGTH: 22
<212> TYPE: DNA
<213> ORGANISM: Artificial Sequence
<220> FEATURE:
<223> OTHER INFORMATION: RTPCR CoAA Synthetic primer
```

```
<400> SEQUENCE: 28
cttcgactac cagcaggctt tt                                              22

<210> SEQ ID NO 29
<211> LENGTH: 21
<212> TYPE: DNA
<213> ORGANISM: Artificial Sequence
<220> FEATURE:
<223> OTHER INFORMATION: Synthetic RT-PCR CoAA Synthetic primer

<400> SEQUENCE: 29
ccgtcagagg cgccacataa g                                               21

<210> SEQ ID NO 30
<211> LENGTH: 20
<212> TYPE: DNA
<213> ORGANISM: Artificial Sequence
<220> FEATURE:
<223> OTHER INFORMATION: Synthetic RT-PCR CoAM primer

<400> SEQUENCE: 30
caaagaagtg aagggcaagc                                                 20

<210> SEQ ID NO 31
<211> LENGTH: 20
<212> TYPE: DNA
<213> ORGANISM: Artificial Sequence
<220> FEATURE:
<223> OTHER INFORMATION: Syntheti RT-PCR CoAM primer

<400> SEQUENCE: 31
aatccagcga ggactttgtc                                                 20

<210> SEQ ID NO 32
<211> LENGTH: 22
<212> TYPE: DNA
<213> ORGANISM: Artificial Sequence
<220> FEATURE:
<223> OTHER INFORMATION: Synthetic primer

<400> SEQUENCE: 32
ggccggaggt agctcttctg ac                                              22

<210> SEQ ID NO 33
<211> LENGTH: 22
<212> TYPE: DNA
<213> ORGANISM: Artificial Sequence
<220> FEATURE:
<223> OTHER INFORMATION: Synthetic primer

<400> SEQUENCE: 33
ctccacagga atggctggcg ac                                              22

<210> SEQ ID NO 34
<211> LENGTH: 22
<212> TYPE: DNA
<213> ORGANISM: Artificial Sequence
<220> FEATURE:
<223> OTHER INFORMATION: Synthetic primer

<400> SEQUENCE: 34
attagaaatg cctttcaagg gg                                              22

<210> SEQ ID NO 35
<211> LENGTH: 22
```

```
<212> TYPE: DNA
<213> ORGANISM: Artificial Sequence
<220> FEATURE:
<223> OTHER INFORMATION: Synthetic primer

<400> SEQUENCE: 35
cttcggctga tagtggacat ac                                              22

<210> SEQ ID NO 36
<211> LENGTH: 22
<212> TYPE: DNA
<213> ORGANISM: Artificial Sequence
<220> FEATURE:
<223> OTHER INFORMATION: Synthetic primer

<400> SEQUENCE: 36
caggcggact cggttctttg ag                                              22

<210> SEQ ID NO 37
<211> LENGTH: 22
<212> TYPE: DNA
<213> ORGANISM: Artificial Sequence
<220> FEATURE:
<223> OTHER INFORMATION: Synthetic primer

<400> SEQUENCE: 37
caaacctcat atacggagtc gc                                              22

<210> SEQ ID NO 38
<211> LENGTH: 19
<212> TYPE: RNA
<213> ORGANISM: Artificial Sequence
<220> FEATURE:
<223> OTHER INFORMATION: Synthetic target sequence of CoAA siRNA

<400> SEQUENCE: 38
guaaccagcc auccucuua                                                  19

<210> SEQ ID NO 39
<211> LENGTH: 19
<212> TYPE: RNA
<213> ORGANISM: Artificial Sequence
<220> FEATURE:
<223> OTHER INFORMATION: Synthetic target sequence of CoAA siRNA

<400> SEQUENCE: 39
uagcgacuaa acacaucaa                                                  19

<210> SEQ ID NO 40
<211> LENGTH: 18
<212> TYPE: DNA
<213> ORGANISM: Artificial Sequence
<220> FEATURE:
<223> OTHER INFORMATION: Synthetic Peptide nucleic acid
<220> FEATURE:
<221> NAME/KEY: misc_feature
<222> LOCATION: (1)..(1)
<223> OTHER INFORMATION: Linked to cell penetrating peptide sequence
      NH2-RRRRRRRQIKIWFQNRRMKWKKGGC-s-s-K
<220> FEATURE:
<221> NAME/KEY: misc_feature
<222> LOCATION: (1)..(18)
<223> OTHER INFORMATION: deoxyribose backbone replaced with a backbone
      having peptide linkages
<220> FEATURE:
<221> NAME/KEY: misc_feature
<222> LOCATION: (18)..(18)
<223> OTHER INFORMATION: Linked to  peptide sequence KKK-CONH
```

```
<400> SEQUENCE: 40
ggctgagggc tgggctcc                                                  18

<210> SEQ ID NO 41
<211> LENGTH: 18
<212> TYPE: DNA
<213> ORGANISM: Artificial Sequence
<220> FEATURE:
<223> OTHER INFORMATION: Synthetic peptide nucleic acid
<220> FEATURE:
<221> NAME/KEY: misc_feature
<222> LOCATION: (1)..(1)
<223> OTHER INFORMATION: Linked to cell penetrating peptide sequence
      NH2-RRRRRRRQIKIWFQNRRMKWKKGGC-s-s-K
<220> FEATURE:
<221> NAME/KEY: misc_feature
<222> LOCATION: (1)..(18)
<223> OTHER INFORMATION: deoxyribose backbone replaced with a backbone
      having peptide linkages
<220> FEATURE:
<221> NAME/KEY: misc_feature
<222> LOCATION: (18)..(18)
<223> OTHER INFORMATION: Linked to  peptide sequence KKK-CONH2

<400> SEQUENCE: 41
ggccactcgc tgctttac                                                  18
```